United States Patent
Anderson et al.

(10) Patent No.: US 7,425,447 B2
(45) Date of Patent: *Sep. 16, 2008

(54) HOST CELLS EXPRESSING 7C10 AND 16C10 CD80-SPECIFIC ANTIBODIES

(75) Inventors: Darrell R. Anderson, Escondido, CA (US); Nabil Hanna, Rancho Santa Fe, CA (US); Peter Brams, Campbell, CA (US)

(73) Assignee: Biogen Idec Inc., Cambridge, MA (US)

( * ) Notice: Subject to any disclaimer, the term of this patent is extended or adjusted under 35 U.S.C. 154(b) by 190 days.

This patent is subject to a terminal disclaimer.

(21) Appl. No.: 11/464,133

(22) Filed: Aug. 11, 2006

(65) Prior Publication Data

US 2006/0275291 A1 Dec. 7, 2006

Related U.S. Application Data

(63) Continuation of application No. 09/576,424, filed on May 22, 2000, now Pat. No. 7,175,847, which is a continuation-in-part of application No. 08/746,361, filed on Nov. 8, 1996, now abandoned, which is a continuation-in-part of application No. 08/487,550, filed on Jun. 7, 1995, now Pat. No. 6,113,898.

(51) Int. Cl.
*C12N 5/10* (2006.01)
*C12N 5/12* (2006.01)
*C12N 15/13* (2006.01)
*C07K 16/28* (2006.01)

(52) U.S. Cl. .................. 435/343.1; 435/326; 435/332; 435/334; 435/346; 530/387.3; 530/388.22; 530/388.7; 530/388.73; 536/23.1; 536/23.53

(58) Field of Classification Search .................. None
See application file for complete search history.

(56) References Cited

U.S. PATENT DOCUMENTS

| | | | |
|---|---|---|---|
| 4,816,397 A | 3/1989 | Boss | |
| 4,816,567 A | 3/1989 | Cabilly | |
| 5,116,964 A | 5/1992 | Capon | |
| 5,304,635 A | 4/1994 | Imam | |
| 5,434,131 A | 7/1995 | Linsley | |
| 5,521,288 A | 5/1996 | Linsley | |
| 5,580,756 A | 12/1996 | Linsley | |
| 5,747,034 A | 5/1998 | De Boer | |
| 5,770,197 A | 6/1998 | Linsley | |
| 5,844,095 A | 12/1998 | Linsley | |
| 5,885,579 A | 3/1999 | Linsley | |
| 6,051,228 A | 4/2000 | Aruffo | |
| 6,113,898 A | 9/2000 | Anderson | |
| 6,162,432 A | 12/2000 | Wallner | |
| 6,709,654 B1 | 3/2004 | Anderson | |
| 6,893,638 B2 | 5/2005 | Anderson | |
| 7,153,508 B2 | 12/2006 | Anderson | |
| 7,175,847 B1 * | 2/2007 | Anderson et al. | 424/153.1 |
| 7,192,585 B2 | 3/2007 | Anderson | |

FOREIGN PATENT DOCUMENTS

| | | |
|---|---|---|
| EP | 0 173 494 | 3/1986 |
| EP | 0 194 276 | 3/1986 |
| EP | 0 451 216 | 10/1991 |
| EP | 0 171 496 | 5/1993 |
| EP | 0 555 880 | 8/1993 |
| EP | 0 239 400 | 8/1994 |
| EP | 0 682 040 | 11/1995 |
| GB | 2 177 096 | 3/1986 |
| WO | WO 87/01131 | 2/1987 |
| WO | WO 90/07861 | 7/1990 |
| WO | WO 92/06193 | 4/1992 |
| WO | WO 93/02108 | 2/1993 |
| WO | WO 93/09812 | 5/1993 |
| WO | WO 93/20210 | 10/1993 |

(Continued)

OTHER PUBLICATIONS

Alegre M., et al, "Effect of single amino acid mutation on the activating and immunosuppressive properties of a "Humanized" OKT3 monoclonal antibody," J. Immunol., 1992, 148:3461-3468.

(Continued)

*Primary Examiner*—Phillip Gambel
(74) *Attorney, Agent, or Firm*—Pillsbury Winthrop Shaw Pittman LLP

(57) ABSTRACT

The present invention relates to the identification of antibodies which are specific to human B7.1 antigen (CD80) and which are capable of inhibiting the binding of B7.1 to a CD28 receptor and which are not capable of inhibiting the binding of B7.1 to a CTLA-4 receptor. Two of these antibodies, 16C10 and 7C10, significantly inhibit the production of IL-2, in spite of the existence of a second activating ligand B7.2 (CD86). Blocking of the primary activation signal between CD28 and B7.1 (CD80) with these antibodies while allowing the unimpaired or coincident interaction of CTLA-4 and B7.1 and/or B7.2 represents a combined antagonistic effect on positive co-stimulation with an agonistic effect on negative signalling. These antibodies may be used as specific immunosuppressants, e.g., for the treatment of autoimmune diseases and to prevent organ transplant rejection.

44 Claims, 20 Drawing Sheets

FOREIGN PATENT DOCUMENTS

| | | |
|---|---|---|
| WO | WO 94/01547 | 1/1994 |
| WO | WO 94/28912 | 12/1994 |
| WO | WO 95/06481 | 3/1995 |
| WO | WO 95/06666 | 3/1995 |
| WO | WO 95/22619 | 8/1995 |
| WO | WO 95/33770 | 12/1995 |
| WO | WO 96/40878 | 12/1996 |
| WO | WO 98/19706 | 5/1998 |

OTHER PUBLICATIONS

Armitage R.J., et al., "Molecular and biological characterization of a murine ligand for CD40," Nature, 1992, 357:80-82.

Azuma M., et al., "CD28 Interaction with B7 costimulates primary allogeneic proliferative responses and cytotoxicity mediated by small resting T lymphocytes," J. Exp. Med., 1992, 175:353-360.

Azuma M., et al., "Functional expression of B7/BB1 on activated T lymphocytes," J. Exp. Med., 1993, 177:845-850.

Azuma M.D., et al., "B7 antigen is a second ligand for CTLA-4 and CD28," Nature, 1993, 366:76-79.

Barbas III, et al. "Human monoclonal Fab frgments derived from a combinatorial library bind to respiratory syncytial virus F glycoprotein and neutralize infectivity," Proc. Natl. Acad. Sci. U.S.A., 1992, 89: 10164-10168.

Ben-Nun A., et al., "The rapid isolation of clonable antigen-specific T lymphocyte lines capable of mediating autoimmune encephalomyelitis," Eur J. Immunol., 1981, 11:195-199.

Blazar B.R., et al., "Infusion of anti-B7.1 (CD80) and anti-B7.2 (CD86) monoclonal antibodies inhibits murine graft-versus-host disease lethality in part via direct effects on CD4+ and CD8+ T cells," J Immunol., 1996, 157:3250-3259.

Boussiotis V.A., et al., "Activated human B lymphocytes express three CTLA-4 counter-receptors that co-stimulate T-Cell activation," Proc. Natl. Acad. Sci., USA, 1993, 90:11059-11063.

Capon D.J., et al., "Designing CD4 immunoadhesins for AIDS therapy," Nature, 1989, 337, 525-531.

Chen et al. "Monoclonal antibody 2D10 recognizes a novel T cell costimulatory molecule on activated murine B lymphocytes." J. Immunol. 1994 152 (5):2105-2114.

Cohen J., "Mounting a targeted strike on unwanted immune responses," (news; comment), Science, 1992, 257:751.

Cohen, J., "New protein steals the show as 'costimulator' of T cells," Science, 1993, 262:844-845.

Daikh et al., "The CD28-B7 costimulatory pathway and its role in autoimmune disease," J. Leukos. Biol., 1997, 62(2):156-162.

Dautigny A., et al., "Molecular cloning and nucleotide sequence of a cDNA clone coding for rat brain myelin proteolipid," FEBS Lett., 1985, 188(1):33-36.

Davila-Bloom et al., "Monoclonal antibody studies of the antigenic determinants of human plasma retinol-binding protein." 1990, J. Nutr. Biochem, 1(5):262-271 (abstract only).

De Boer M., et al., "Functional characterization of a novel Anti-B7 monoclonal antibody," Eur. Journal of Immunology, 1992, 22:3071-3075.

Delabie J., et al., "The B7/BB1 antigen is expressed by Reed-Sternberg cells of Hodgkin's disease and contributes to the stimulating capacity of Hodgkin's disease-derived cell lines," Blood, 1993, 82:2845-52.

Dermer G.B., et al., "Another anniversary for the war on cancer," Biotechnology, 1994, 12:320.

Dillman R.O., et al., "Antibodies as cytotoxic therapy," J Clin Oncol., 1994, 12:1497-1515.

Durie F.H., et al., "Prevention of collagen-induced arthritis with an antibody to gp39, the ligand for CD40," Science, 1993, 261:1328-1330.

Durie F.H., et al., "The role of CD40 and its ligand (gp39) in peripheral and central tolerance and its contribution to autoimmune disease," Research in Immunology, 1994, 145(3), 200-205 & 244-249.

Engel et al, "The B7-2 (B70) costimulatory molecule expressed by monocytes and activated B lymphocytes is the CD86 differentiation antigen," Blood, 1994, 84:1402-1407.

Falini B., et al., "Response of refractory Hodgkin's disease to monoclonal anti-CD30 immunotoxin," The Lancet, 1992, 339:1195-1196.

Freeman G.J., et al., "Cloning of B7.2: a CTLA-4 counter-receptor that costimulates human T cell proliferation," Science, 1993, 262:909-911.

Freeman G.J., et al., "CTLA-4 and CD28 mRNA are coexpressed in most T cells after activation," The Journal of Immunology, 1992, 149:3795-3801.

Freeman G.J., et al., "Structure, expression, and T cell costimulatory activity of the murine homologue of the human B lymphocyte activation antigen B7," J. Exp. Med., 1991, 174:625-631.

Freeman G.J., et al., "Uncovering of functional alternative CTLA-4 counter-receptor in B7-deficient mice," Science, 1993, 262:907-909.

Geenen V. and G. Kroemer, "Multiple ways to cellular immune tolerance," Immunology Today, 1993, 14:573.

Gerritse K., et al., "CD40-CD40 ligand interactions in experimental allergic encephalomyelitis and multiple sclerosis," Proc. Natl. Acad. Sci. USA, 1996, 93:2499-2504.

Gimmi C.D., et al., "Human T-cell clonal anergy is induced by antigen presentation in the absence of B7 costimulation," Proc. Natl. Acad. Sci., 1993, 90:6586-6590.

Gottlieb A., et al., "Clinical and histologic response to single-dose treatment of moderate to severe psoriasis with an anti-CD80 monoclonal antibody," J Am Acad Dermatol., 2002, 47:692-700.

Gottlieb A., et al., "Results of a single-dose, dose-escalating trial of an anti-B7.1 monoclonal antibody (IDEC-114) in patients with psoriasis," J Invest Dermatol., 2000, 114:840, Abstract No. 546.

Gottlieb A.B. et al. "Evaluation of safety and clinical activity of multiple doses of the anti-CD80 monoclonal Antibody, galiximab in patients with moderate to severe plaque psoriasis," 2004, 111:28-37.

Gribben J.G., et al., "CTLA-4 mediates antigen specific apoptosis of human T cells." Proc. Natl. Acad. Sci. USA, 1995, 92:811-815.

Grumet F.C., et al., "Soluble form of an HLA-B7 class I antigen specifically suppresses humoral alloimmunization." Human Immunology, 1995, 40:228-234.

Guinan E.C., et al., "Pivotal role of the B7:CD28 pathway in transplantation tolerance and tumor immunity," Blood, 1994, 84:3261-3282.

Guo J. "Mutational analysis and and alternatively spliced product of B7 defines Its CD28/CTLA4-binding site on immunoglobulin C-like domain." Exp. Med. 1995 181(4)1345-1355.

Hafler D.A., et al., "The potential of restricted T cell recognition of myelin basis protein epitopes in the therapy of multiple sclerosis," Ann. NY Acad. Sci., 1991, 636:251-265.

Harding F.A., et al., "CD28 mediated signalling co-stimulates murine T cells and prevents induction of anergy in T cell clones." Nature, 1992, 356:607-609.

Hariharan K., et al., "Therapeutic activity of IDEC-114 (anti-CD80) and rituximab (Rituxan®) in B-cell lymphoma," Blood, 2001, 98(11 part 1):608a, Abstract No. 2549.

Hart D.N.J., et al., "B7/BB-1 is a leucocyte differentiation antigen on human dendritic cells induced by activation." Immunology, 1993, 79:616-620.

Haspot et al., "Differential effect of CD28 versus B7 blockade on direct pathway of allorecognition and self-restricted responses" Blood, 2002, 99(6):2228-2234.

Hathcock et al., "Comparative analysis of B7-1 and B7-2 costimulatory ligands: expression and function," J. Exp. Med., 1994, 180(2):631-640.

Hathcock K.S., et al., "Identification of an alternative CTLA-4 ligand costimulatory for T cell activation," Science, 1993, 262:905-907.

Hollenbaugh D., et al., "The human T cell antigen gp39, a member of the TNF gene family, is a ligand for the CD40 receptor: expression of a soluble form of gp39 with B cell co-stimulatory activity," The EMBO J., 1992, 11(12):4313-4321.

Inaba et al., "The tissue distribution of the B7-2 co-stimulator in mice: abundant expression on dendritic cells in situ and during maturation in vitro," J. Exp. Med., 1994, vol. 180, No. 5, pp. 1849-1860.

Ionescu-Tirgoviste, et al, "Correlations between insulin antibodies and the HLA system in a group of Type I diabetic patients in Bucharest," Med. Interre, 1986, 24(1), 11-17.

Janeway C.A., Jr. and K. Bottomly, "Signals and Signs for Lymphocyte Responses," Cell, 1994, 76:275-285.

Jemmerson et al., "Crystallization of two monoclonal Fab fragments of similar amino-acid sequence bound to the same area of horse cytochrome c and interacting by potentially distinct mechanisms." Acta Crytallogr. D. Biol. Crystallogr., 1994; 50 (pt. 1): 64-70 (abstract only).

Jenkins M.K., "The role of cell division in the induction of clonal anergy." Immunology Today, 1992, 13:69.

June C.H., et al., "The B7 and CD28 receptor families," Immunol Today, 1994, 15:321-331.

Kahan B.D., Immunosuppressive therapy, curr opin immunol., 1992, 4:553-560.

Karpus,W.J., et al., "CD4+ suppressor cells differentially affect the production of IFN-α by effector cells of experimental autoimmune encephalomyelitis," J. Immunol., 1989, 143:3492-3497.

Krummel M., et al., "CD28 and CTLA-4 have opposing effects on the response of T cells to stimulation," J. Exp. Med., 1995, 182:459-466.

Kuchroo et al., "B7-1 and B7-2 costimulatory molecules activate differentially the Th1/Th2 developmental pathways: application to autoimmune disease therapy," 1995, Cell, 80:707-718.

Kuntz, "Structure-based strategies for drug design and discovery," Science, 1992, 257(5073):1078-1082.

Laman J., et al., "The role of gp39 (CD40 ligand) in EAE and MS," Journal of Neuroimmunology, 1994, 54(1-2):175, Abstract No. P01.06.

LaSalle J.M., et al., "Early signaling defects in human T cells anergized by T cell presentation of autoantigen," J. Exp. Med., 1992, 176:177-186.

Lederman S., et al., "Identification of a novel surface protein on activated CD4+ T cells that induces contact-dependent B cell differentiation (Help)," J. Exp. Med., 1992, 175:1091-1101.

Lehtinen et al., "Evaluation of serum antibody response to a newly identified B-cell epitope in the minor nucleocapsid protein L2 of human papillomavirus type 16." 1993, Clin. Diag. Virol., 1(3):153-65 (abstract only).

Lenschow D.J., et al., "Differential effects of anti-B7.1 and anti-B7.2 monoclonal antibody treatment on the development of diabetes in the Nonobese Diabetic Mouse," 1995, J. Exp. Med., 181:, 1145-1155.

Lenschow D.J., et al., "Expression and functional significance of an additional ligand for CTLA-4," Proc. Natl. Acad. Sci., USA,1993, 90:11054-11058.

Lenschow D.J., et al., "Inhibition of transplant rejection following treatment with anti-B7-2 and anti-B7.1 antibodies," 1995,Transplantation, 60:1171-1178.

Lenschow D.J., et al., "Long-term survival of xenogeneic pancreatic islet grafts induced by CTLA 4Ig," Science, 1992, 257:789-795.

Lider O., et al., "Suppression of experimental autoimmune encephalomyelitis by oral administration of myelin basic protein," J. Immunol., 1989, 142:748-752.

Lin H., et al., "Long-term acceptance of major histocompatibility complex mismatched cardiac allografts induced by CTLA-4-Ig plus donor specific transfusion," J. Exp. Med., 1993, 178:1801.

Lincumpao et al. "Intracellular localization and epitope mapping of feline herpesvirus type 1 glycoproteins." Nippon Juigaku Zasshi, 1990, 52(2) 351-9 (abstract).

Linsley P.S., et. al., "Coexpression and functional cooperation of CTLA-4 and CD28 on activated T lymphocytes." J. Exp. Med., 1992, 176:1595-1604.

Linsley P.S., et. al., "T-Cell Antigen CD28 mediates adhesion with B Cells by interacting with activation antigen B7/BB-1." Proc. Natl. Acad. Sci., 1990, 87:5031-5035.

Linsley, et al, "CD28 engagement by B7/BB-1 induces transient down-regulation of CD28 synthesis and prolonged unresponsiveness to CD28 signaling," The Journal of Immunology, 1993, 150:3161-3169.

Linsley, et al., "Binding of the B cell activation antigen B7 to CD28 costimulates T cell proliferation and interleukin 2 mRNA accumulation," J. Exp. Med., 1991, 173:721-730.

Linsley, P.S. et al., "The role of the CD28 receptor during T cell responses to antigen," Annu Rev Immunol., 1993, 11:191-212.

Linsley, P.S., et al., "CTLA-4 is a second receptor for the B Cell activation antigen B7," J. Exp. Med., 1991, 174:561.

Liu et al., "Co-stimulation of murine CD4-T cell growth cooperation between B7 and heat-stable antigen," Eur. J. Immunol., 1992, vol. 22, No. 11, pp. 2855-2859.

Liu, et al., "Blockade of CD28/CTLA-4-B7 co-stimulatory pathway in colitic SCID mice," Gastroenterology, 2000, Part 1 of 2, 118(4 Suppl 2):AGA-A575, Abstract No. 3000.

Liu et al. "B7 interactions with CD28 and CTLA-4 control tolerance or induction of mucosal inflammation in chronic experimental colitis." J. Immunol., 2001; 167 (3): 1830-1838.

McCafferty J., et al., "Phage antibodies: filamentous phage displaying antibody variable domains," Nature, 1990, 348:552-554.

Mehta et al., "The role of N-linked carbohydrate residues in lymphokine-activated killer cell-mediated cytolysis," Cellular Immunology, 1994, 155(1):95-110.

Miller A., et al., "Antigen-driven bystander suppression after oral administration of antigens," J. Exp. Med., 1991, 174:791-798.

Mokhtarion F., et al., "Adoptive transfer of myelin basic protein-sensitized T cells produces chronic relapsing demyelinating disease in mice," Nature, 1984, 309:356-358.

Morrison S., et al., "Chimeric human antibody molecules: mouse antigen-binding domains with human constant region domains," Proc. Natl. Acad, Sci. U.S.A., 1984, 81:6851-6855.

Morton P.A., et al., "Differential effects of CTLA-4 substitutions on the binding of human CD80 (B7-1) and CD86 (B7-2)," J. Immunol., 1996,156:1047-1054.

Munro J.M., et al., "In vivo expression of the B7 costimulatory molecule by subsets of antigen-presenting cells and the malignant cells of Hodgkin's disease," Blood, 1994, 83:793-798.

Nakajima et al., "Preferential dependence of autoantibody production in murine lupus on CD86 costimulatory molecule," European Journal of Immunology, 1995, 25(11):3060-3069.

Nestle F.O., et al, "Characterization of dermal dendritic cells in psoriasis," J. Clin. Invest., 1994, 94: 202-209.

Newman et al., "Primatization of recombinant antibodies for iimmunotherapy of human diseases: a macaque/human chimeric antibody against human CD4," Biotechnology, 1992, vol. 10, No. 11, pp. 1455-1460.

Ngo et al., In the protein folding problem and tertiary structure prediction, Merz et al. (Ed.), Birkhauser, Boston MA., 1994, pp. 433, 492-495.

Nickoloff B.J. et al., "T lymphocytes in skin lesions of psoriasis and mycosis fungoides express B7-1: a ligand for CD28," Blood, 1994, 83(9):2580-2586.

Noelle R.J., et al., "A 39-kDa protein on activated helper T cells binds CD40 and transducers the signal for cognate activation of B cells," Proc. Natl. Acad. Sci. USA, 1992, 89:6550-6554.

Olsson L., et al., "Human-human monoclonal antibody-producing hybridomas: technical aspects," Meth, Enzymol., 1983, 92:3-17.

Ossevoort et al. "Prolonged skin graft survival by administration of anti-CD80 monoclonal antibody wit cyclosporine A." J. Immunother., 1999 22 (5):381-389 (abstract only).

Paul (ed), Fundamental Immunology, Raven Press (1993) p. 242.

Peach et al "Both extracellular immunoglobin-like domains of CD80 contain residues critical for binding T cell surface receptors CTLA-4 and CD28," J. Biol. Chem, 1995, 270(36):21181-21187.

Perrin P.J. et al., "Opposing effects of CTLA4-Ig and anti-CD80 (B7-1) plus anti-CD86 (B7-2) on experimental allergic encephalomyelitis," J Neuroimmunol., 1996, 65:31-39.

Pesoa S.A., et al., "Regulation of experimental allergic encephalomyelitis. Part 5. role of the recipient in suppressor cell induction," J. Neuroimmunol, 1984, 7:131-135.

Pettinelli C.B., et al., "Adoptive transfer of experimental allergic encephalomyelitis in SJL/J mice after in vitro activation of lymph node cells by myelin basic protein: requirement for Lyt 1+2-T lymphocytes," J. Immunol., 1981, 127:1420-1423.

Powers et al. "Expresion and functional analysis of murine B7 dlineated by a novel monoclonal antibody." Cell Immunol., 1994, 153(2)298-311.

Razi-Wolf et al., "Expression and function of the murine B7 antigen, the major costimulatory molecule expressed by peritoneal exudate cells," PNAS, 1992, 89:4210-4214.

Schopf "IDEC-114," Curr Opin Investig Drugs, 2001, 2:635-638.

Schwartz R.H., "A cell culture model for T lymphocyte clonal anergy," Science, 1990, 248:1349-1356.

Schwartz R.H., "Co-stimulation of T lymphocytes: The role of CD28, CTLA-4, and B7/BB1 in interleukin-2 production and immunotherapy," Cell, 1992, 71:1065-1068.

Selvakumar,A., et al., "Genomic organization and chromosomal location of the human gene encoding the B-lymphocyte activation antigen B7," Immunogenetics, 1992, 36:175-181.

Skolnick et al., "From genes to protein structure and function: novel applications of computational approaches in the genomic era," Trends Biotechnology, 2000, 18(1):34-39.

Sobel R.A., et al., "Acute experimental allergic encephalomyelitis in SJL/J mice induced by a synthetic peptide of myelin proteolipid protein," J. Neuropathol. Exp. Neurol., 1990, 49(5):468-479.

Stamenkovic I., et al., "A B-lymphocyte activation molecule related to the nerve growth factor receptor and induced by cytokines in carcinomas," The EMBO J., 1989, 8(5),1403-1410.

Suvas S., et al., "Distinct role of CD80 and CD86 in the regulation of the activation of B cell and B cell lymphoma," J Biol Chem., 2002, 277(10):7766-7775.

Takeda S., et al., "Construction of chimaeric processed immunoglobulin genes containing mouse variable and human constant region sequences," Nature, 1985, 314(4):452-454.

Tan P., et al., "Induction of alloantigen-specific hyporesponsiveness in human T lymphocytes by blocking interaction of CD28 with its Natural Ligand B7/BB1," J. Exp. Med., 1993, 177:165-173.

Teng N. H. et al., "Construction and testing of mouse-human heteromyelomas for human monoclonal antibody production," Proc. Natl. Acad. Sci. U.S. A., 1983, 80:7308-7312.

Tivol E.A., et al., "Loss of CTLA-4 leads to massive lymphoproliferation and fatal multiorgan tissue destruction, revealing a critical negative regulatory role of CTLA-4," Immunity, 1995, 3:541-547.

Toubert A., et al., "Epitope mapping of an HLA-B27 monoclonal antibody that also reacts with a 35-kD bacterial out-membrane protein," Clin. Exp. Immunol., 1990, 82(1), 16-20.

Toubert A., et al., "Epitope mapping of HLA-B27 and HLA-B7 antigens by using intradomain recombinants," J. Immunol., 1988, 141(7), 2503-2509.

Tuohy V.K., et al., "Identification of an encephalitogenic determinant of myelin proteolipid protein for SJL mice," J. Immunol., 1989, 142:1523-1527.

Turka L.A., et al., "T-cell activation by the CD28 ligand B7 is required for cardiac allograft rejection in vivo," Proc. Natl. Acad. Sci., USA, 1992, 89:11102-11105.

Valle et al., "mAb 104, a new monoclonal antibody, recognizes the B7 antigen that is expressed on activated cells and HTLV-1-transformed T cells," Immunol., 1990, 69(4), 531-535.

van der Merwe, et al., "CD80 (B7-1) binds both CD28 and CTLA-4 with a low affinity and very fast kinetics," J. Exp. Med., 1997,185: 393-403.

Van der Veen R. C., et al., "The adoptive transfer of chronic relapsing experimental allergic encephalomyelitis with lymph node cells sensitized to myelin proteolipid protein," J. Neuroimmunol., 1989, 21:183-191.

Van Gool et al., "Synergy between Cyclosporin A and a monoclonal antibody to B7 in blocking alloantigen-induced T-cell activation," Blood, 1994, 83(1):176-183.

Vandenberghe P., et al.. "Antibody and B7/BB1-mediated ligation of the CD28 receptor induces tyrosine phosphorylation in human T cells," J. Exp. Med., 1992, 175:951 960.

Vanderlugt et al. "Pathologic role and temporal appearance of newly emerging autoepitopes in relapsing Experimental Autoimmune Encephalomyelitis" J. Immunology., 2000, 164:670-678.

Ward E.S., et al., "Binding activities of a repertoire of single immunoglobulin variable domains secreted from *Escherichia coli*," Nature, 1989, 341:544-546.

Ward P.A., et al., "Blocking of adhesion molecules in vivo as anti-inflammatory therapy," Ther Immunol., 1994, 1:165-171.

Webster's II New Riverside University Dictionary, The Riverside Publishing Company, 1988, pp. 435 and 762.

Weiner et al., "Monoclonal antibody therapy of B cell lymphoma," Expert Opin. Biol. Ther., 2004, 4(3):375-385.

Wettendorff et al., "Generation of humanized Fab fragments of B7-24 mAb, an antibody with potential use in prevention of graft rejection and development of graft-versus-host-disease," Med Fac Landbouww. Univ. Gent., 1995, 60(4):2057-2063.

Weyl D., et al., "Epitope mapping of human monoclonal antibodies to HLA-B27 by using natural and mutated antigenic variants," Hum. Immunol., 1991, 31(4), 271-276.

Yi-qun Z. et al., Differential requirements for co-stimulatory signals from B7 family members by resting versus recently activated memory T cells towards soluble recall antigens, Int Immunol., 1996, 8:37-44.

Zavazava N., et al., et al, "Inhibition of anti-HLA-B7 alloreactive CTL by affinity-purified soluble HLA," Transplantation, 1991, 51(4):838-842.

* cited by examiner

```
Frame 1  M   R   V   P   A   Q   L   L   G   L   L   L   L   W   L   P   G   A   R
         ATG AGG GTC CCC GCT CAG CTC CTG GGG CTC CTG CTG CTC TGG CTC CCA GGT GCA CGA
                     9           18          27          36          45          54

C   A   Y   E   L   T   Q   P   P   S   V   S   V   S   P   G   Q   T   A   R   I
         TGT GCC TAT GAA CTG ACT CAG CCA CCC TCG GTG TCA GTG TCC CCA GGA CAG ACG GCC AGG ATC
                 63          72          81          90          99          108         117

T   C   G   G   D   N   S   R   N   E   Y   V   H   W   Y   Q   Q   K   P   A   R
         ACC TGT GGG GGA GAC AAC AGT AGA AAT GAA TAT GTC CAC TGG TAC CAG CAG AAG CCA GCG CGG
                 126         135         144         153         162         171         180

A   P   I   L   V   I   Y   D   D   S   D   R   P   S   G   I   P   E   R   F   S
         GCC CCT ATA CTG GTC ATC TAT GAT GAT AGT GAC CGG CCC TCA GGG ATC CCT GAG CGA TTC TCT
                 189         198         207         216         225         234         243

G   S   K   S   G   N   T   A   T   L   T   I   N   G   V   E   A   G   D   E   A
         GGC TCC AAA TCA GGG AAC ACC GCC ACC CTG ACC ATC AAC GGG GTC GAG GCC GGG GAT GAG GCT
                 252         261         270         279         288         297         306

D   Y   Y   C   Q   V   W   D   R   A   S   D   H   P   V   F   G   G   G   T   R
         GAC TAT TAC TGT CAG GTG TGG GAC AGG GCT AGT GAT CAT CCG GTC TTC GGA GGA GGG ACC CGG
                 315         324         333         342         351         360         369

V   T   V   L   G   Q   P   K   A   A   P   S   V   T   L   F   P   P   S   S   E
         GTG ACC GTC CTA GGT CAG CCC AAG GCT GCC CCC TCG GTC ACT CTG TTC CCG CCC TCC TCT GAG
                 378         387         396         405         414         423         432

E   L   Q   A   N   K   A   T   L   V   C   L   I   S   D   F   Y   P   G   A   V
         GAG CTT CAA GCC AAC AAG GCC ACA CTG GTG TGT CTC ATA AGT GAC TTC TAC CCG GGA GCC GTG
                 441         450         459         468         477         486         495

T   V   A   W   K   A   D   S   S   P   V   K   A   G   V   E   T   T   T   P   S
         ACA GTG GCC TGG AAG GCA GAT AGC AGC CCC GTC AAG GCG GGA GTG GAG ACC ACC ACA CCC TCC
                 504         513         522         531         540         549         558

K   Q   S   N   N   K   Y   A   A   S   S   Y   L   S   L   T   P   E   Q   W   K
         AAA CAA AGC AAC AAC AAG TAC GCG GCC AGC AGC TAC CTG AGC CTG ACG CCT GAG CAG TGG AAG
                 567         576         585         594         603         612         621

S   H   R   S   Y   S   C   Q   V   T   H   E   G   S   T   V   E   K   T   V   A
         TCC CAC AGA AGC TAC AGC TGC CAG GTC ACG CAT GAA GGG AGC ACC GTG GAG AAG ACA GTG GCC
                 630         639         648         657         666         675         684

P   T   E   C   S
         CCT ACA GAA TGT TCA TGA
                 693         702
```

FIG. 3A

```
Frame 1  M   K   H   L   W   F   F   L   L   L   V   A   A   P   R   W   V   L   S
         ATG AAA CAC CTG TGG TTC TTC CTC CTC CTG GTG GCA GCT CCC AGA TGG GTC CTG TCC
                     9              18              27              36              45              54

Q   V   K   L   Q   Q   W   G   E   G   L   L   Q   P   S   E   T   L   S   R   T
         CAG GTG AAG CTG CAG CAG TGG GGC GAA GGA CTT CTG CAG CCT TCG GAG ACC CTG TCC CGC ACC
                     63              72              81              90              99              108             117

C   V   V   S   G   G   S   I   S   G   Y   Y   Y   W   T   W   I   R   Q   T   P
         TGC GTT GTC TCT GGT GGC TCC ATC AGC GGT TAC TAC TAC TGG ACC TGG ATC CGC CAG ACC CCA
                     126             135             144             153             162             171             180

G   R   G   L   E   W   I   G   H   I   Y   G   N   G   A   T   T   N   Y   N   P
         GGG AGG GGA CTG GAG TGG ATT GGC CAT ATT TAT GGT AAT GGT GCG ACC ACC AAC TAC AAT CCC
                     189             198             207             216             225             234             243

S   L   K   S   R   V   T   I   S   K   D   T   S   K   N   Q   F   F   L   N   L
         TCC CTC AAG AGT CGA GTC ACC ATT TCA AAA GAC ACG TCC AAG AAC CAG TTC TTC CTG AAC TTG
                     252             261             270             279             288             297             306

N   S   V   T   D   A   D   T   A   V   Y   Y   C   A   R   G   P   R   P   D   C
         AAT TCT GTG ACC GAC GCG GAC ACG GCC GTC TAT TAC TGT GCG AGA GGC CCT CGC CCT GAT TGC
                     315             324             333             342             351             360             369

T   T   I   C   Y   G   G   W   V   D   V   W   G   P   G   D   L   V   T   V   S
         ACA ACC ATT TGT TAT GGC GGC TGG GTC GAT GTC TGG GGC CCG GGA GAC CTG GTC ACC GTC TCC
                     378             387             396             405             414             423             432

S   A   S   T   K   G   P   S   V   F   P   L   A   P   S   S   K   S   T   S   G
         TCA GCT AGC ACC AAG GGC CCA TCG GTC TTC CCC CTG GCA CCC TCC TCC AAG AGC ACC TCT GGG
                     441             450             459             468             477             486             495

G   T   A   A   L   G   C   L   V   K   D   Y   F   P   E   P   V   T   V   S   W
         GGC ACA GCG GCC CTG GGC TGC CTG GTC AAG GAC TAC TTC CCC GAA CCG GTG ACG GTG TCG TGG
                     504             513             522             531             540             549             558

N   S   G   A   L   T   S   G   V   H   T   F   P   A   V   L   Q   S   S   G   L
         AAC TCA GGC GCC CTG ACC AGC GGC GTG CAC ACC TTC CCG GCT GTC CTA CAG TCC TCA GGA CTC
                     567             576             585             594             603             612             621

Y   S   L   S   S   V   V   T   V   P   S   S   S   L   G   T   Q   T   Y   I   C
         TAC TCC CTC AGC AGC GTG GTG ACC GTG CCC TCC AGC AGC TTG GGC ACC CAG ACC TAC ATC TGC
                     630             639             648             657             666             675             684

N   V   N   H   K   P   S   N   T   K   V   D   K   K   A   E   P   K   S   C   D
         AAC GTG AAT CAC AAG CCC AGC AAC ACC AAG GTG GAC AAG AAA GCA GAG CCC AAA TCT TGT GAC
                     693             702             711             720             729             738             747

K   T   H   T   C   P   P   C   P   A   P   E   L   L   G   G   P   S   V   F   L
         AAA ACT CAC ACA TGC CCA CCG TGC CCA GCA CCT GAA CTC CTG GGG GGA CCG TCA GTC TTC CTC
                     756             765             774             783             792             801             810

F   P   P   K   P   K   D   T   L   M   I   S   R   T   P   E   V   T   C   V   V
         TTC CCC CCA AAA CCC AAG GAC ACC CTC ATG ATC TCC CGG ACC CCT GAG GTC ACA TGC GTG GTG
                     819             828             837             846             855             864             873

V   D   V   S   H   E   D   P   E   V   K   F   N   W   Y   V   D   G   V   E   V
         GTG GAC GTG AGC CAC GAA GAC CCT GAG GTC AAG TTC AAC TGG TAC GTG GAC GGC GTG GAG GTG
                     882             891             900             909             918             927             936
```

FIG. 3B

```
 H   N   A   K   T   K   P   R   E   E   Q   Y   N   S   T   Y   R   V   V   S   V
CAT AAT GCC AAG ACA AAG CCG CGG GAG GAG CAG TAC AAC AGC ACG TAC CGT CTG GTC AGC GTC
    945         954         963         972         981         990         999

L   T   V   L   H   Q   D   W   L   N   G   K   E   Y   K   C   K   V   S   N   K
CTC ACC GTC CTG CAC CAG GAC TGG CTG AAT GGC AAG GAG TAC AAG TGC AAG GTC TCC AAC AAA
    1008        1017        1026        1035        1044        1053        1062

A   L   P   A   P   I   E   K   T   I   S   K   A   K   G   Q   P   R   E   P   Q
GCC CTC CCA GCC CCC ATC GAG AAA ACC ATC TCC AAA GCC AAA GGG CAG CCC CGA GAA CCA CAG
    1071        1080        1089        1098        1107        1116        1125

V   Y   T   L   P   P   S   R   D   E   L   T   K   N   Q   V   S   L   T   C   L
GTG TAC ACC CTG CCC CCA TCC CGG GAT GAG CTG ACC AAG AAC CAG GTC AGC CTG ACC TGC CTG
    1134        1143        1152        1161        1170        1179        1188

V   K   G   F   Y   P   S   D   I   A   V   E   W   E   S   N   G   Q   P   E   N
GTC AAA GGC TTC TAT CCC AGC GAC ATC GCC GTG GAG TGG GAG AGC AAT GGG CAG CCG GAG AAC
    1197        1206        1215        1224        1233        1242        1251

N   Y   K   T   T   P   P   V   L   D   S   D   G   S   F   F   L   Y   S   K   L
AAC TAC AAG ACC ACG CCT CCC GTG CTG GAC TCC GAC GGC TCC TTC TTC CTC TAC AGC AAG CTC
    1260        1269        1278        1287        1296        1305        1314

T   V   D   K   S   R   W   Q   Q   G   N   V   F   S   C   S   V   M   H   E   A
ACC GTG GAC AAG AGC AGG TGG CAG CAG GGG AAC GTC TTC TCA TGC TCC GTG ATG CAT GAG GCT
    1323        1332        1341        1350        1359        1368        1377

L   H   N   H   Y   T   Q   K   S   L   S   L   S   P   G   K   .
CTG CAC AAC CAC TAC ACG CAG AAG AGC CTC TCC CTG TCT CCG GGT AAA TGA
    1386        1395        1404        1413        1422        1431
```

FIG. 3C

```
Frame 1  M   S   L   P   A   Q   L   L   G   L   L   L   L   C   V   P   G   S   S
         ATG AGC CTC CCT GCT CAG CTC CTC GGG CTG CTA TTG CTC TGC GTC CCC GGG TCC AGT
                 9           18          27          36          45          54

G   E   V   V   M   T   Q   S   P   L   S   L   P   I   T   P   G   E   P   A   S
GGG GAA GTT GTG ATG ACT CAG TCT CCA CTG TCC CTT CCC ATC ACA CCT GGA GAG CCG GCC TCC
        63          72          81          90          99          108         117

I   S   C   R   S   S   Q   S   L   K   H   S   N   G   D   T   F   L   S   W   Y
ATC TCC TGT AGG TCT AGT CAA AGC CTT AAA CAC AGT AAT GGA GAC ACC TTC CTG AGT TGG TAT
    126         135         144         153         162         171         180

Q   Q   K   P   G   Q   P   P   R   L   L   I   Y   K   V   S   N   R   D   S   G
CAG CAG AAG CCA GGC CAA CCT CCA AGG CTC CTG ATT TAT AAG GTT TCT AAC CGG GAC TCT GGG
    189         198         207         216         225         234         243

V   P   D   R   F   S   G   S   G   A   G   T   D   F   T   L   K   I   S   A   V
GTC CCA GAC AGA TTC AGC GGC AGT GGG GCA GGG ACA GAT TTC ACA CTG AAA ATC AGC GCA GTG
    252         261         270         279         288         297         306

E   A   E   D   V   G   V   Y   F   C   G   Q   G   T   R   T   P   P   T   F   G
GAG GCT GAA GAT GTT GGG GTT TAT TTC TGC GGG CAA GGT ACA AGG ACT CCT CCC ACT TTC GGC
    315         324         333         342         351         360         369

G   G   T   K   V   E   I   K   R   T   V   A   A   P   S   V   F   I   F   P   P
GGA GGG ACC AAG GTG GAA ATC AAA CGT ACG GTG GCT GCA CCA TCT GTC TTC ATC TTC CCG CCA
    378         387         396         405         414         423         432

S   D   E   Q   L   K   S   G   T   A   S   V   V   C   L   L   N   N   F   Y   P
TCT GAT GAG CAG TTG AAA TCT GGA ACT GCC TCT GTT GTG TGC CTG CTG AAT AAC TTC TAT CCC
    441         450         459         468         477         486         495

R   E   A   K   V   Q   W   K   V   D   N   A   L   Q   S   G   N   S   Q   E   S
AGA GAG GCC AAA GTA CAG TGG AAG GTG GAT AAC GCC CTC CAA TCG GGT AAC TCC CAG GAG AGT
    504         513         522         531         540         549         558

V   T   E   Q   D   S   K   D   S   T   Y   S   L   S   S   T   L   T   L   S   K
GTC ACA GAG CAG GAC AGC AAG GAC AGC ACC TAC AGC CTC AGC AGC ACC CTG ACG CTG AGC AAA
    567         576         585         594         603         612         621

A   D   Y   E   K   H   K   V   Y   A   C   E   V   T   H   Q   G   L   S   S   P
GCA GAC TAC GAG AAA CAC AAA GTC TAC GCC TGC GAA GTC ACC CAT CAG GGC CTG AGC TCG CCC
    630         639         648         657         666         675         684

V   T   K   S   F   N   R   G   E   C
GTC ACA AAG AGC TTC AAC AGG GGA GAG TGT TGA
    693         702         711         720
```

FIG. 4A

```
Frame 1  M   G   W   S   L   I   L   L   F   L   V   A   V   A   T   R   V   Q   C
         ATG GGT TGG AGC CTC ATC TTG CTC TTC CTT GTC GCT GTT GCT ACG CGT GTC CAG TGT
                 9           18          27          36          45          54
         E   V   Q   L   V   E   S   G   G   G   L   V   Q   P   G   G   S   L   R   V   S
         GAG GTG CAA CTG GTG GAG TCT GGG GGA GGC TTG GTC CAG CCT GGC GGG TCC CTG AGA GTC TCC
             63          72          81          90          99          108         117
         C   A   V   S   G   F   T   F   S   D   H   Y   M   Y   W   F   R   Q   A   P   G
         TGT GCA GTC TCT GGA TTC ACC TTC AGT GAC CAC TAC ATG TAT TGG TTC CGC CAG GCT CCA GGG
             126         135         144         153         162         171         180
         K   G   P   E   W   V   G   F   I   R   N   K   P   N   G   G   T   T   E   Y   A
         AAG GGG CCG GAA TGG GTA GGT TTC ATT AGA AAC AAA CCG AAC GGT GGG ACA ACA GAA TAC GCC
             189         198         207         216         225         234         243
         A   S   V   K   D   R   F   T   I   S   R   D   D   S   K   S   I   A   Y   L   Q
         GCG TCT GTG AAA GAC AGA TTC ACC ATC TCC AGA GAT GAT TCC AAA AGC ATC GCC TAT CTG CAA
             252         261         270         279         288         297         306
         M   S   S   L   K   I   E   D   T   A   V   Y   Y   C   T   T   S   Y   I   S   H
         ATG AGC AGC CTG AAA ATC GAG GAC ACG GCC GTC TAT TAC TGT ACT ACA TCC TAC ATT TCA CAT
             315         324         333         342         351         360         369
         C   R   G   G   V   C   Y   G   G   Y   F   E   F   W   G   Q   G   A   L   V   T
         TGT CGG GGT GGT GTC TGC TAT GGA GGT TAC TTC GAA TTC TGG GGC CAG GGC GCC CTG GTC ACC
             378         387         396         405         414         423         432
         V   S   S   A   S   T   K   G   P   S   V   F   P   L   A   P   S   S   K   S   T
         GTC TCC TCA GCT AGC ACC AAG GGC CCA TCG GTC TTC CCC CTG GCA CCC TCC TCC AAG AGC ACC
             441         450         459         468         477         486         495
         S   G   G   T   A   A   L   G   C   L   V   K   D   Y   F   P   E   P   V   T   V
         TCT GGG GGC ACA GCG GCC CTG GGC TGC CTG GTC AAG GAC TAC TTC CCC GAA CCG GTG ACG GTG
             504         513         522         531         540         549         558
         S   W   N   S   G   A   L   T   S   G   V   H   T   F   P   A   V   L   Q   S   S
         TCG TGG AAC TCA GGC GCC CTG ACC AGC GGC GTG CAC ACC TTC CCG GCT GTC CTA CAG TCC TCA
             567         576         585         594         603         612         621
         G   L   Y   S   L   S   S   V   V   T   V   P   S   S   S   L   G   T   Q   T   Y
         GGA CTC TAC TCC CTC AGC AGC GTG GTG ACC GTG CCC TCC AGC AGC TTG GGC ACC CAG ACC TAC
             630         639         648         657         666         675         684
         I   C   N   V   N   H   K   P   S   N   T   K   V   D   K   K   A   E   P   K   S
         ATC TGC AAC GTG AAT CAC AAG CCC AGC AAC ACC AAG GTG GAC AAG AAA GCA GAG CCC AAA TCT
             693         702         711         720         729         738         747
         C   D   K   T   H   T   C   P   P   C   P   A   P   E   L   L   G   G   P   S   V
         TGT GAC AAA ACT CAC ACA TGC CCA CCG TGC CCA GCA CCT GAA CTC CTG GGG GGA CCG TCA GTC
             756         765         774         783         792         801         810
         F   L   F   P   P   K   P   K   D   T   L   M   I   S   R   T   P   E   V   T   C
         TTC CTC TTC CCC CCA AAA CCC AAG GAC ACC CTC ATG ATC TCC CGG ACC CCT GAG GTC ACA TGC
             819         828         837         846         855         864         873
         V   V   V   D   V   S   H   E   D   P   E   V   K   F   N   W   Y   V   D   G   V
         GTG GTG GTG GAC GTG AGC CAC GAA GAC CCT GAG GTC AAG TTC AAC TGG TAC GTG GAC GGC GTG
             882         891         900         909         918         927         936
```

FIG. 4B

```
E   V   H   N   A   K   T   K   P   R   E   E   Q   Y   N   S   T   Y   R   V   V
GAG GTG CAT AAT GCC AAG ACA AAG CCG CGG GAG GAG CAG TAC AAC AGC ACG TAC CGT GTG GTC
    945         954         963         972         981         990         999

S   V   L   T   V   L   H   Q   D   W   L   N   G   K   E   Y   K   C   K   V   S
AGC GTC CTC ACC GTC CTG CAC CAG GAC TGG CTG AAT GGC AAG GAG TAC AAG TGC AAG GTC TCC
    1008        1017        1026        1035        1044        1053        1062

N   K   A   L   P   A   P   I   E   K   T   I   S   K   A   K   G   Q   P   R   E
AAC AAA GCC CTC CCA GCC CCC ATC GAG AAA ACC ATC TCC AAA GCC AAA GGG CAG CCC CGA GAA
    1071        1080        1089        1098        1107        1116        1125

P   Q   V   Y   T   L   P   P   S   R   D   E   L   T   K   N   Q   V   S   L   T
CCA CAG GTG TAC ACC CTG CCC CCA TCC CGG GAT GAG CTG ACC AAG AAC CAG GTC AGC CTG ACC
    1134        1143        1152        1161        1170        1179        1188

C   L   V   K   G   F   Y   P   S   D   I   A   V   E   W   E   S   N   G   Q   P
TGC CTG GTC AAA GGC TTC TAT CCC AGC GAC ATC GCC GTG GAG TGG GAG AGC AAT GGG CAG CCG
    1197        1206        1215        1224        1233        1242        1251

E   N   N   Y   K   T   T   P   P   V   L   D   S   D   G   S   F   F   L   Y   S
GAG AAC AAC TAC AAG ACC ACG CCT CCC GTG CTG GAC TCC GAC GGC TCC TTC TTC CTC TAC AGC
    1260        1269        1278        1287        1296        1305        1314

K   L   T   V   D   K   S   R   W   Q   Q   G   N   V   F   S   C   S   V   M   H
AAG CTC ACC GTG GAC AAG AGC AGG TGG CAG CAG GGG AAC GTC TTC TCA TGC TCC GTG ATG CAT
    1323        1332        1341        1350        1359        1368        1377

E   A   L   H   N   H   Y   T   Q   K   S   L   S   L   S   P   G   K
GAG GCT CTG CAC AAC CAC TAC ACG CAG AAG AGC CTC TCC CTG TCT CCG GGT AAA TGA
    1386        1395        1404        1413        1422        1431
```

FIG. 4C

```
Frame 1  M.  R   V   P   A   Q   L   L   G   L   L   L   L   W   L   P   G   A   R
         ATG AGG GTC CCC GCT CAG CTC CTG GGG CTC CTG CTG CTC TGG CTC CCA GGT GCA CGA
                 9       18          27          36          45          54

C   E   S   A   L   T   Q   P   P   S   V   S   G   A   P   G   Q   K   V   T   I
         TGT GAG TCT GCC CTG ACA CAG CCG CCC TCA GTG TCT GGG GCC CCA GGG CAG AAG GTC ACC ATC
             63          72          81          90          99          108         117

S   C   T   G   S   T   S   N   I   G   G   Y   D   L   H   W   Y   Q   Q   L   P
         TCG TGC ACT GGG AGC ACC TCC AAC ATT GGA GGT TAT GAT CTA CAT TGG TAC CAG CAG CTC CCA
             126         135         144         153         162         171         180

G   T   A   P   K   L   L   I   Y   D   I   N   K   R   P   S   G   I   S   D   R
         GGA ACG GCC CCC AAA CTC CTC ATC TAT GAC ATT AAC AAG CGA CCC TCA GGA ATT TCT GAC CGA
             189         198         207         216         225         234         243

F   S   G   S   K   S   G   T   A   A   S   L   A   I   T   G   L   Q   T   E   D
         TTC TCT GGC TCC AAG TCT GGT ACC GCG GCC TCC CTG GCC ATC ACT GGG CTC CAG ACT GAG GAT
             252         261         270         279         288         297         306

E   A   D   Y   Y   C   Q   S   Y   D   S   S   L   N   A   Q   V   F   G   G   G
         GAG GCT GAT TAT TAC TGC CAG TCC TAT GAC AGC AGC CTG AAT GCT CAG GTA TTC GGA GGA GGG
             315         324         333         342         351         360         369

T   R   L   T   V   L   G   Q   P   K   A   A   P   T   V   T   L   F   P   P   S
         ACC CGG CTG ACC GTC CTA GGT CAG CCC AAG GCT GCC CCC ACG GTC ACT CTG TTC CCG CCC TCC
             378         387         396         405         414         423         432

S   E   E   L   Q   A   N   K   A   T   L   V   C   L   I   S   D   F   Y   P   G
         TCT GAG GAG CTT CAA GCC AAC AAG GCC ACA CTG GTG TGT CTC ATA AGT GAC TTC TAC CCG GGA
             441         450         459         468         477         486         495

A   V   T   V   A   W   K   A   D   S   S   P   V   K   A   G   V   E   T   T   T
         GCC GTG ACA GTG GCC TGG AAG GCA GAT AGC AGC CCC GTC AAG GCG GGA GTG GAG ACC ACC ACA
             504         513         522         531         540         549         558

P   S   K   Q   S   N   N   K   Y   A   A   S   S   Y   L   S   L   T   P   E   Q
         CCC TCC AAA CAA AGC AAC AAC AAG TAC GCG GCC AGC AGC TAC CTG AGC CTG ACG CCT GAG CAG
             567         576         585         594         603         612         621

W   K   S   H   R   S   Y   S   C   Q   V   T   H   E   G   S   T   V   E   K   T
         TGG AAG TCC CAC AGA AGC TAC AGC TGC CAG GTC ACG CAT GAA GGG AGC ACC GTG GAG AAG ACA
             630         639         648         657         666         675         684

V   A   P   T   E   C   S   .
         GTG GCC CCT ACA GAA TGT TCA TGA
             693         702         711
```

FIG. 5A

```
Frame 1  M   K   H   L   W   F   F   L   L   L   V   A   A   P   R   W   V   L   S
         ATG AAA CAC CTG TGG TTC TTC CTC CTC CTG GTG GCA GCT CCC AGA TGG GTC CTG TCC
             9           18          27          36          45          54

Q   V   Q   L   Q   E   S   G   P   G   L   V   K   P   S   E   T   L   S   L   T
         CAG GTG CAG CTG CAG GAG TCG GGC CCA GGA CTG GTG AAG CCT TCG GAG ACC CTG TCC CTC ACC
             63          72          81          90          99          108         117

C   A   V   S   G   G   S   I   S   G   G   Y   G   W   G   W   I   R   Q   P   P
         TGC GCT GTC TCT GGT GGC TCC ATC AGC GGT GGT TAT GGC TGG GGC TGG ATC CGC CAG CCC CCA
             126         135         144         153         162         171         180

G   K   G   L   E   W   I   G   S   F   Y   S   S   S   G   N   T   Y   Y   N   P
         GGG AAG GGG CTG GAG TGG ATT GGG AGT TTC TAT AGT AGT AGT GGG AAC ACC TAC TAC AAC CCC
             189         198         207         216         225         234         243

S   L   K   S   Q   V   T   I   S   T   D   T   S   K   N   Q   F   S   L   K   L
         TCC CTC AAG AGT CAA GTC ACC ATT TCA ACA GAC ACG TCC AAG AAC CAG TTC TCC CTG AAG CTG
             252         261         270         279         288         297         306

N   S   M   T   A   A   D   T   A   V   Y   Y   C   V   R   D   R   L   F   S   V
         AAC TCT ATG ACC GCC GCG GAC ACG GCC GTG TAT TAC TGT GTG AGA GAT CGT CTT TTT TCA GTT
             315         324         333         342         351         360         369

V   G   M   V   Y   N   N   W   F   D   V   W   G   P   G   V   L   V   T   V   S
         GTT GGA ATG GTT TAC AAC AAC TGG TTC GAT GTC TGG GGC CCG GGA GTC CTG GTC ACC GTC TCC
             378         387         396         405         414         423         432

S   A   S   T   K   G   P   S   V   F   P   L   A   P   S   S   K   S   T   S   G
         TCA GCT AGC ACC AAG GGC CCA TCG GTC TTC CCC CTG GCA CCC TCC TCC AAG AGC ACC TCT GGG
             441         450         459         468         477         486         495

G   T   A   A   L   G   C   L   V   K   D   Y   F   P   E   P   V   T   V   S   W
         GGC ACA GCG GCC CTG GGC TGC CTG GTC AAG GAC TAC TTC CCC GAA CCG GTG ACG GTG TCG TGG
             504         513         522         531         540         549         558

N   S   G   A   L   T   S   G   V   H   T   F   P   A   V   L   Q   S   S   G   L
         AAC TCA GGC GCC CTG ACC AGC GGC GTG CAC ACC TTC CCG GCT GTC CTA CAG TCC TCA GGA CTC
             567         576         585         594         603         612         621

Y   S   L   S   S   V   V   T   V   P   S   S   S   L   G   T   Q   T   Y   I   C
         TAC TCC CTC AGC AGC GTG GTG ACC GTG CCC TCC AGC AGC TTG GGC ACC CAG ACC TAC ATC TGC
             630         639         648         657         666         675         684

N   V   N   H   K   P   S   N   T   K   V   D   K   K   A   E   P   K   S   C   D
         AAC GTG AAT CAC AAG CCC AGC AAC ACC AAG GTG GAC AAG AAA GCA GAG CCC AAA TCT TGT GAC
             693         702         711         720         729         738         747

K   T   H   T   C   P   P   C   P   A   P   E   L   L   G   G   P   S   V   F   L
         AAA ACT CAC ACA TGC CCA CCG TGC CCA GCA CCT GAA CTC CTG GGG GGA CCG TCA GTC TTC CTC
             756         765         774         783         792         801         810

F   P   P   K   P   K   D   T   L   M   I   S   R   T   P   E   V   T   C   V   V
         TTC CCC CCA AAA CCC AAG GAC ACC CTC ATG ATC TCC CGG ACC CCT GAG GTC ACA TGC GTG GTG
             819         828         837         846         855         864         873

V   D   V   S   H   E   D   P   E   V   K   F   N   W   Y   V   D   G   V   E   V
         GTG GAC GTG AGC CAC GAA GAC CCT GAG GTC AAG TTC AAC TGG TAC GTG GAC GGC GTG GAG GTG
             882         891         900         909         918         927         936
```

FIG. 5B

```
 H   N   A   K   T   K   P   R   E   E   Q   Y   N   S   T   Y   R   V   V   S   V
CAT AAT GCC AAG ACA AAG CCG CGG GAG GAG CAG TAC AAC AGC ACG TAC CGT GTG GTC AGC GTC
    945         954         963         972         981         990         999

L   T   V   L   H   Q   D   W   L   N   G   K   E   Y   K   C   K   V   S   N   K
CTC ACC GTC CTG CAC CAG GAC TGG CTG AAT GGC AAG GAG TAC AAG TGC AAG GTC TCC AAC AAA
    1008        1017        1026        1035        1044        1053        1062

A   L   P   A   P   I   E   K   T   I   S   K   A   K   G   Q   P   R   E   P   Q
GCC CTC CCA GCC CCC ATC GAG AAA ACC ATC TCC AAA GCC AAA GGG CAG CCC CGA GAA CCA CAG
    1071        1080        1089        1098        1107        1116        1125

V   Y   T   L   P   P   S   R   D   E   L   T   K   N   Q   V   S   L   T   C   L
GTG TAC ACC CTG CCC CCA TCC CGG GAT GAG CTG ACC AAG AAC CAG GTC AGC CTG ACC TGC CTG
    1134        1143        1152        1161        1170        1179        1188

V   K   G   F   Y   P   S   D   I   A   V   E   W   E   S   N   G   Q   P   E   N
GTC AAA GGC TTC TAT CCC AGC GAC ATC GCC GTG GAG TGG GAG AGC AAT GGG CAG CCG GAG AAC
    1197        1206        1215        1224        1233        1242        1251

N   Y   K   T   T   P   P   V   L   D   S   D   G   S   F   F   L   Y   S   K   L
AAC TAC AAG ACC ACG CCT CCC GTG CTG GAC TCC GAC GGC TCC TTC TTC CTC TAC AGC AAG CTC
    1260        1269        1278        1287        1296        1305        1314

T   V   D   K   S   R   W   Q   Q   G   N   V   F   S   C   S   V   M   H   E   A
ACC GTG GAC AAG AGC AGG TGG CAG CAG GGG AAC GTC TTC TCA TGC TCC GTG ATG CAT GAG GCT
    1323        1332        1341        1350        1359        1368        1377

L   H   N   H   Y   T   Q   K   S   L   S   L   S   P   G   K
CTG CAC AAC CAC TAC ACG CAG AAG AGC CTC TCC CTG TCT CCG GGT AAA TGA
    1386        1395        1404        1413        1422        1431
```

FIG. 5C

HOST CELLS EXPRESSING 7C10 AND 16C10 CD80-SPECIFIC ANTIBODIES

RELATED APPLICATIONS

This is a continuation of U.S. application Ser. No. 09/576,424, filed May 22, 2000, and issued as U.S. Pat. No. 7,175,847, which is continuation-in-part of U.S. application Ser. No. 08/746,361, filed Nov. 8, 1996, now abandoned, which is a continuation-in-part of U.S. application Ser. No. 08/487,550, filed Jun. 7, 1995, and issued as U.S. Pat. No. 6,113,898. Each of the above-identified applications is incorporated by reference in its entirety herein.

FIELD OF THE INVENTION

The present invention relates to the identification and use of monoclonal antibodies which are specific to B7.1 antigens (CD80). More specifically, the present invention relates to the identification and use of monoclonal antibodies or PRIMATIZED® forms thereof which are capable of inhibiting the binding of human B7.1 antigen to a CD28 receptor and which are not capable of inhibiting the binding of B7.1 to a CTLA-4 receptor. Thus, the invention relates to the identification and use of monoclonal antibodies and PRIMATIZED® forms thereof which recognize specific sites on the B7.1 antigen which are exclusive of CTLA-4 receptor binding.

The invention further relates to monoclonal antibodies or PRIMATIZED® forms thereof which recognize specific sites on the human B7.1 antigen and are capable of inhibiting IL-2 production.

Also, the present invention relates to pharmaceutical compositions containing monoclonal or PRIMATIZED® antibodies specific to human B7.1 and their use as immunosuppressants by modulating the B7:CD28 pathway, e.g., for the treatment of autoimmune disorders, and the prevention of organ rejection.

BACKGROUND OF THE INVENTION

The clinical interface between immunology, hematology, and oncology has long been appreciated. Many conditions treated by the hematologist or oncologist have either an autoimmune or immuno-deficient component to their pathophysiology that has led to the widespread adoption of immunosuppressive medications by hematologists, whereas oncologists have sought immunologic adjuvants that might enhance endogenous immunity to tumors. To date, these interventions have generally consisted of nonspecific modes of immunosuppression and immune stimulation. In addition to the limited efficacy of these interventions, toxicities secondary to their nonspecificity have also limited their overall success. Therefore, alternative strategies have been sought.

Elucidation of the functional role of a rapidly increasing number of cell surface molecules has contributed greatly to the integration of immunology with clinical hematology and oncology. Nearly 200 cell surface antigens have been identified on cells of the immune and hematopoietic systems (Schlossman S F, Boumsell L, Gilks J M, Harlan T, Kishimoto, C Morimoto C, Ritz J., Shaw S, Silverstein R L, Springer T A, Tedder T F, Todd R F:CD antigens (1993), *Blood* 83:879, 1994). These antigens represent both lineage-restricted and more widely distributed molecules involved in a variety of processes, including cellular recognition, adhesion, induction and maintenance of proliferation, cytokine secretion, effector function, and even cell death. Recognition of the functional attributes of these molecules has fostered novel attempts to manipulate the immune response. Although molecules involved in cellular adhesion and antigen-specific recognition have previously been evaluated as targets of therapeutic immunologic intervention, recent attention has focused on a subgroup of cell surface molecules termed co-stimulatory molecules (Bretscher P: "The two-signal model of lymphocyte activation twenty-one years later." *Immunol. Today* 13:73 (1992); Jenkins M K, Johnson J G: "Molecules involved in T-cell co-stimulation." *Curr Opin Immunol* 5:351 (1993); Geppert T, Davis L. Gur H. Wacholtz M. Lipsky P: "Accessory cell signals involved in T-cell activation." *Immunol Rev* 117:5 (1990); Weaver C T, Unanue E R: "The co-stimulatory function of antigen-presenting cells." *Immunol Today* 11:49 (1990); Stennam R M, Young J W: "Signals arising from antigen-presenting cells." *Curr Opin Immunol* 3:361 (1991)). Co-stimulatory molecules do not initiate but rather enable the generation and amplification of antigen-specific T-cell responses and effector function (Bretscher P: "The two-signal model of lymphocyte activation twenty-one years later." *Immunol. Today* 13:73 (1992); Jenkins M K, Johnson J G: "Molecules involved in T-cell co-stimulation." *Curr Opin Immunol* 5:351 (1993); Geppert T, Davis L. Gur H. Wacholtz M. Lipsky P: "Accessory cell signals involved in T-cell activation." *Immunol Rev* 117:5 (1990); Weaver C T, Unanue E R: "The co-stimulatory function of antigen-presenting cells." *Immunol Today* 11:49, (1990); Stennam R M, Young J W: "Signals arising from antigen-presenting cells." *Curr Opin Immunol* 3:361 (1991); June C H, Bluestone J A, Linsley P S, Thompson C D: "Role of the CD28 receptor in T-cell activation." *Immunol Today* 15:321 (1994)).

Recently, one specific co-stimulatory pathway termed B7:CD28 has been studied by different research groups because of its significant role in B- and T-cell activation (June C H, Bluestone J A, Linsley P S, Thompson C D: "Role of the CD28 receptor in T-cell activation." *Immunol Today* 15:321 (1994); June C H, Ledbetter J A: "The role of the CD28 receptor during T-cell responses to antigen." *Annu Rev Immunol* 11:191 (1993); Schwartz R H: "Co-stimulation of T lymphocytes: The role of CD28, CTLA-4, and B7/BB1 in interleukin-2 production and immunotherapy." *Cell* 71:1065-1068 (1992); Jenkins M K, Taylor P S, Norton S D, Urdahl K B: "CD28 delivers a co-stimulatory signal involved in antigen-specific IL-2 production by human T cells." *Journal of Immunology* 147:2461-2466 (1991)). Since this ligand:receptor pathway was discovered four years ago, a large body of evidence has accumulated suggesting that B7:CD28 interactions represent one of the critical junctures in determining immune reactivity versus anergy (June C H, Bluestone J A, Linsley P S, Thompson C D: "Role of the CD28 receptor in T-cell activation." *Immunol Today* 15:321 (1994); June C H, Ledbetter J A: "The role of the CD28 receptor during T-cell responses to antigen." Annu Rev Immunol 11:191 (1993); Schwartz R H: "Co-stimulation of T lymphocytes: The role of CD28, CTLA-4, and B7/BB1 in interleukin-2 production and immunotherapy." *Cell* 71:1065-1068 (1992); Cohen J: "Mounting a targeted strike on unwanted immune responses" (news; comment). *Science* 257:751 (1992); Cohen J: "New protein steals the show as 'co-stimulator' of T cells" (news; comment). *Science* 262:844 (1993)).

In particular, the role of the human B7 antigens, i.e., human B7.1 (CD80) and B7.2 (CD86), has been reported to play a co-stimulatory role in T-cell activation. See, e.g., Gimmi C D, Freeman, G J, Gribben J G, Sugita K, Freedman A S, Morimoto C, Nadler L M: "B-cell surface antigen B7 provides a costimulatory signal that induces T cells to proliferate and secrete interleukin 2." *Proc. Natl. Acad. Sci. (USA)* 88:6575-6579 (1991).

1. B7.1 and B7.2 Co-Stimulatory Role in T Cell Activation

The elaboration of a successful immune response depends on a series of specific interactions between a T cell and an antigen presenting cell. Although the essential first step in this process depends upon the binding of antigen to the T cell receptor, in the context of the MHC class II molecule (Lane, P. J. L., F. M. McConnell, G. L. Schieven, E. A. Clark, and J. A. Ledbetter, (1990), "The Role of Class II Molecules in Human B Cell Activation." *The Journal of Immunology* 144: 3684-3692), this interaction alone is not sufficient to induce all the events necessary for a sustained response to a given antigen (Schwartz, R. H. (1990), "A Cell Culture Model for T Lymphocyte Clonal Anergy." *Science* 248:1349; Jenkins, M. K. (1992), "The Role of Cell Division in the Induction of Clonal Anergy." *Immunology Today* 13:69; Azuma, M., M. Cayabyab, D. Buck, J. H. Phillips, and L. L. Lanier (1992), "Involvement of CD28 in MHC-unrestricted Cytotoxicity Mediated by a Human Natural Killer Leukemia Cell Line." *The Journal of Immunology* 149:1115-1123; Azuma, M., M. Cayabyab, D. Buck, J. H. Phillips, and L. L. Lanier (1992), "CD28 Interaction with B7 Costimulates Primary Allogeneic Proliferative Responses and Cytotoxicity Mediated by Small Resting T Lymphocytes." *J. Exp. Med.* 175:353-360); S. D. Norton, L. Zuckerman, K. B. Urdahl, R. Shefaer, J. Miller, and M. K. Jenkins (1992), "The CD28 Ligand, B7, Enhances IL-2 Production by Providing a Costimulatory Signal to T Cells." *The Journal of Immunology* 149:1556-1561; R. H. Schwartz (1992), "Costimulation of T Lymphocytes: The Role of CD28, CTLA-4, and B7/BB1 in Interleukin-2 Production and Immunotherapy." *Cell* 71:1065-1068).

The involvement of certain other co-stimulatory molecules is necessary (Norton, S. D., L. Zuckerman, K. B. Urdahl, R. Shefler, J. Miller, and M. K. Jenkins (1992), "The CD28 Ligand, B7, Enhances IL-2 Production by Providing A Costimulatory Signal to T Cells." *The Journal of Immunology* 149:1556-1561)). "The homodimers CD28 and CTLA-4 expressed on T cells" (June, C. H., J. A. Ledbetter, P. S. Linsley, and C. B. Thompson (1990), "Role of the CD28 Receptor in T-Cell Activation." *Immunology Today* 11:211-216; Linsley, P. S., W. Brady, M. Umes, L. S. Grosmaire, N. K. Damle, and J. A. Ledbetter (1991), "CTLA-4 is a Second Receptor for the B Cell Activation Antigen B7." *J Exp. Med.* 174:561)), together with B7.1 (CD80) and B7.2 (CD86) expressed on antigen presenting cells, are major pairs of co-stimulatory molecules necessary for a sustained immune response (Azuma, M., H. Yssel, J. H. Phillips, H. Spits, and L. L. Lanier (1993), "Functional Expression of B7/BB1 on Activated T Lymphocytes." *J Exp. Med.* 177:845-850; Freeman, G. J., A. S. Freedman, J. M. Segil, G. Lee, J. F. Whitman, and L M. Nadler (1989), "B7, A New Member of the Ig Superfamily with Unique Expression on Activated and Neoplastic B Cells." *The Journal of Immunology* 143:2714-2722; Hathcock, K. S., G. Laslo, H. B. Dickler, J. Bradshaw, P. Linsley, and R. J. Hodes (1993), "Identification of an Alternative CTLA-4 Ligand Costimulatory for T Cell Activation." *Science* 262:905-911; Hart, D. N. J., G. C. Starling, V. L. Calder, and N. S. Fernando (1993), "B7/BB-1 is a Leucocyte Differentiation Antigen on Human Dendritic Cells Induced by Activation." *Immunology* 79:616-620). It can be shown in vitro that the absence of these co-stimulatory signals leads to an aborted T cell activation pathway and the development of unresponsiveness to the specific antigen, or anergy. (See, e.g., Harding, F. A., J. G. McArthur, J. A. Gross, D. M. Raulet, and J. P. Allison (1992), "CD28 Mediated Signaling Co-stimulates Murine T Cells and Prevents Induction of Anergy in T Cell Clones." *Nature* 356:607-609; Gimmi, C. D., G. J. Freeman, J. G. Gribben, G. Gray, and L. M. Nadler (1993); "Human T-Cell Clonal Anergy is Induced by Antigen Presentation in the Absence of B7 Costimulation.", *Proc. Natl. Acad. Sci.* 90:6586-6590; Tan, P., C. Anasefti, J. A. Hansen, J. Melrose, M. Brunvand, J. Bradshaw, J. A. Ledbetter, and P. S. Linsley (1993), "Induction of Alloantigen-specific Hyporesponsiveness in Human T Lymphocytes by Blocking Interaction of CD28 with Its Natural Ligand B7/BB 1." *J. Exp. Med.* 177:165-173). Achievement of in vivo tolerance constitutes a mechanism for immunosuppression and a viable therapy for organ transplant rejection and for the treatment of autoimmune diseases. This has been achieved in experimental models following the administration of CTLA-4Ig (Lenschow, D. J., Y. Zeng, R. J. Thistlethwaite, A. Montag, W. Brady, M. G. Gibson, P. S. Linsley, and J. A. Bluestone (1992), "Long-Term Survival of Xenogeneic Pancreatic Islet Grafts Induced by CTLA-4Ig." *Science* 257:789-795).

The molecules B7.1 and B7.2 can bind to either CD28 or CTLA-4, although B7.1 binds to CD28 with a Kd of 200 Nm and to CTLA-4 with a 20-fold higher affinity (Linsley, P. S., E. A. Clark, and J. A. Ledbetter (1990), "T-Cell Antigen CD28 Mediates Adhesion with B Cells by Interacting with Activation Antigen B7/BB-l." *Proc. Natl. Acad. Sci.* 87:5031-5035; Linsley et al (1993), "The Role of the CD28 receptor during T cell responses to antigen," *Annu. Rev. Immunol.* 11:191-192; Linesley et al (1993), "CD28 Engagement by B7/BB-1 Induces Transient Down-Regulation of CD28 Synthesis and Prolonged Unresponsiveness to CD28 Signaling," *The Journal of Immunology* 150:3151-3169). B7.1 is expressed on activated B cells and interferon induced monocytes, but not resting B cells (Freeman, G. J., G. S. Gray, C. D. Gimmi, D. B. Lomarrd, L-J. Zhou, M. White, J. D. Fingeroth, J. G. Gribben, and L M. Nadler (1991). "Structure, Expression and T Cell Costimulatory Activity of the Murine Homologue of the Human B Lymphocyte Activation Antigen B7," *J. Exp. Med.,* 174:625-631). B7.2, on the other hand, is constitutively expressed at very low levels on resting monocytes, dendritic cells and B cells, and its expression is enhanced on activated T cells, NK cells and B lymphocytes (Azuma, M. D. Ito, H. Yagita, K. Okumura, J. H. Phillips, L. L. Lanier, and C. Somoza 1993, "B70 Antigen is a Second Ligand for CTLA-4 and CD28," *Nature,* 366:76-79). Although B7.1 and B7.2 can be expressed on the same cell type, their expression on B cells occurs with different kinetics (Lenschow, D. J., G. H. Su, L. A. Zuckerman, N. Nabavi, C. L. Jellis, G. S. Gray, J. Miller, and J. A. Bluestone (1993), "Expression and Functional Significance of an Additional Ligand for CTLA-4," *Proc. Natl. Acad. Sci., USA,* 90:11054-11058; Boussiotis, V. A., G. J. Freeman, J. G. Gribben, J. Daley, G. Gray, and L. M. Nadler (1993), "Activated Human B Lymphocytes Express Three CTLA-4 Counter-receptors that Co-stimulate T-Cell Activation." *Proc. Natl. Acad. Sci., USA,* 90:11059-11063). Further analysis at the RNA level has demonstrated that B7.2 mRNA is constitutively expressed, whereas B7.1 MRNA is detected 4 hours after activation and initial low levels of B7.1 protein are not detectable until 24 hours after stimulation (Boussiotis, V. A., G. J. Freeman, J. G. Gribben, J. Daley, G. Gray, and L. M. Nadler (1993), "Activated Human B Lymphocytes Express Three CTLA-4 Counter-receptors that Co-stimulate T-Cell Activation," *Proc. Natl. Acad. Sci., USA,* 90:11059-11063). CTLA-4/CD28 counter receptors, therefore, may be expressed at various times after B Cell activation.

More recently, it has been suggested that the second T cell associated co-receptor CTLA-4 apparently functions as a negative modulator to override and prevent a runaway immune system (Krummel M, Allison J: "CD28 and CTLA-4 have opposing effects on the response of T cells to stimulation." *J. Exp. Med.* 182:459-466 (1995)). The CTLA-4 receptor plays a critical role in down regulating the immune response, as evidenced in CTLA-4 knockout mice. Knockout mice born without the ability to express the CTLA-4 gene die within 3-4 weeks of severe lymphoproliferative disorder (Tivol E A, Borriello G, Schweitzer A N, Lynch W P, Bluestone J A, Sharpe A H: "Loss of CTLA-4 leads to massive lymphoproliferation and fatal multiorgan tissue destruction, revealing a critical negative regulatory role of CTLA-4." *Immunity* 3:541-547 (1995)). CTLA-4 is thought to function through signaling mechanisms linked to induction of apoptosis (Gribben J G, Freeman G J, Boussiotis V A, Rennert P, Jellis C L, Greenfield E, Barber M, Restivo Jr. V A, Ke X, Gray G S, Nadler L M: "CTLA-4 mediates antigen specific apoptosis of human T cells." *Proc. Natl. Acad. Sci. USA* 92:811-815 (1995)), triggered through as yet undefined ligand binding to specific cites on the receptor. It has been shown in vitro that the blocking of the B7.1/B7.2 dependent co-stimulatory signals in various ways leads to an aborted T cell activating pathway and the development of unresponsiveness to the specific antigen (Lederman S, Chess L, Yellin M J: "Murine monoclonal antibody (5c8) recognizes a human glycoprotein on the surface of T-lymphocytes, compositions containing same." U.S. Pat. No. 5,474,771 (Dec. 12, 1995); Linsley P S, Ledbetter J A, Damle N K, Brady W: "Chimeric CTLA4 receptor and methods for its use." U.S. Pat. No. 5,434,131 (Jul. 18, 1995); Harding, 1992; Gimmi C D, Freeman G J, Bribben J G, Gray G, Nadler L M: "Human T-cell clonal anergy is induced by antigen presentation in the absence of B7 costimulation." *Proc. Natl. Acad. Sci. (USA)* 90:6586-6590 (1993); Tan P, Anasetti C, Hansen J A, Melrose J, Brunvand M, Bradshaw J, Ledbetter J A, Linsley P S: "Induction of alloantigen-specific hyporesponsiveness in human T lymphocytes by blocking interaction of CD28 with its natural ligand B7/BB1." *J. Exp. Med.* 177:165-173 (1993)). Achievement of in vivo tolerance, anergy, or depleting of antigen-specific T cells would constitute a mechanism for immunosuppression and a viable therapy for organ transplant rejection or plausible treatment for autoimmune diseases.

The differential temporal expression of B7.1 and B7.2 suggests that the interaction of these two molecules with CTLA-4 and/or CD28 deliver distinct but related signals to the T cell (LaSalle, J. M., P. J. Tolentino, G. J. Freeman, L. M. Nadler, and D. A. Hafler, (1992), "CD28 and T Cell Antigen Receptor Signal Transduction Coordinately Regulate Interleukin 2 Gene Expression In Response to Superantigen Stimulation," J. Exp. Med., 176:177-186; Vandenberghe, P., G. J. Freeman, L. M. Nadler, M. C. Fletcher, M. Kamoun, L. A. Turka, J. A. Ledbetter, C. B. Thompson, and C. H. June (1992), "Antibody and B7/BB 1-mediated Ligation of the CD28 Receptor Induces Tyrosine Phosphorylation in Human T Cells," *The Journal of Experimental Medicine* 175:951-960)). The exact signaling functions of CTLA-4 and CD28 on the T cell are currently unknown (Janeway, C. A., Jr. and K. Bottomly, (1994), "Signals and Signs for Lymphocyte Responses," *Cell* 76.275285). However, it is possible that one set of receptors could provide the initial stimulus for T cell activation and the second, a sustained signal to allow further elaboration of the pathway and clonal expansion to take place (Linsley, P. S., J. L. Greene, P. Tan, J. Bradshaw, J. A. Ledbetter, C. Anasetti, and N. K. Damle, (1992), "Coexpression and Functional Cooperation of CTLA-4 and CD28 on Activated T Lymphocytes," *J. Exp. Med.* 176:1595-1604). The current data supports the two-signal hypothesis proposed by Jenkins and Schwartz (Schwartz, R. H. (1990), "A Cell Culture Model for T Lymphocyte Clonal Anergy," *Science* 248: 1349; Jenkins, M. K., (1992), "The Role of Cell Division in the Induction of Clonal Anergy," *Immunology Today* 13:69)) that both a TCR and co-stimulatory signal are necessary for T cell expansion, lymphokine secretion and the full development of effector function (Greenan, V. and G. Kroemer (1993), "Multiple Ways to Cellular Immune Tolerance," *Immunology Today* 14:573). The failure to deliver the second signal results in the inability of T cells to secrete IL-2 and renders the cell unresponsive to antigen.

Structurally, both B7.1 and B7.2 contain extracellular immunoglobulin superfamily V and C-like domains, a hydrophobic transmembrane region and a cytoplasmic tail (Freeman, G. J., J. G. Gribben, V. A. Boussiotis, J. W. Ng, V. Restivo, Jr., L. A. Lombard, G. S. Gray, and L. M. Nadler (1993), "Cloning of B7.2: A CTLA-4 Counter-receptor that Co-stimulates Human T Cell Proliferation," *Science* 262:909). Both B7.1 and B7.2 are heavily glycosylated. B7.1 is a 44-54 kD glycoprotein comprised of a 223 amino acid extracellular domain, a 23 amino acid transmembrane domain, and a 61 amino acid cytoplasmic tail. B7.1 contains 3 potential protein kinase phosphorylation sites. (Azuma, M., H. Yssel, J. H. Phillips, H. Spits, and L. L. Lanier, (1993), "Functional Expression of B7/BB1 on Activated T Lymphocytes," *J. Exp. Med.* 177:845-850). B7.2 is a 306 amino acid membrane glycoprotein. It consists of a 220 amino acid extracellular region, a 23 amino acid hydrophobic transmembrane domain and a 60 amino acid cytoplasmic tail (Freeman, G. J., A. S. Freedman, J. M. Segil, G. Lee, J. F. Whitman, and L M. Nadler (1989), "B7, A New Member of the Ig Superfamily with Unique Expression on Activated and Neoplastic B Cells," *The Journal of Immunology* 143:2714-2722). Although both B7.1 and B7.2 genes are localized in the same chromosomal region (Freeman, G. J., D. B. Lombard, C. D. Gimmi, S. A. Brod, L Lee, J. C. Laning, D. A. Hafler, M. E. Dorf, G. S. Gray, H. Reiser, C. H. June, C. B. Thompson, and L. M. Nadler (1992), "CTLA-4 and CD28 MRNA are Coexpressed in Most T Cells After Activation," *The Journal of Immunology* 149:3795-3801; Schwartz, R. H. (1992), "Costimulation of T Lymphocytes: The Role of CD28, CTLA-4, and B7/BB1" in Selvakumar, A., B. K. Mohanraj, R. L. Eddy, T. B. Shows, P. C. White, C. Perrin, and B. Dupont (1992), "Genomic Organization and Chromosomal Location of the Human Gene Encoding the B-Lymphocyte Activation Antigen B7," *Immunogenetics* 36:175-181), these antigens do not share a high level of homology. The overall homology between B7.1 and B7.2 is 26% and between murine B7.1 and human B7.1 is 27% (Azuma, M., H. Yssel, J. H. Phillips, H. Spits, and L. L. Lanier (1993), "Functional Expression of B7/BB1 on Activated T Lymphocytes," *J. Exp. Med.* 177:845-850; Freeman, G. J., A. S. Freedman, J. M. Segil, G. Lee, J. F. Whitman, and L M. Nadler (1989), "B7, A New Member of the Ig Superfamily with Unique Expression on Activated and Neoplastic B Cells," *The Journal of Immunology* 143:2714-2722). Although alignment of human B7.1 human B7.2 and murine B7.1 sequences shows few stretches of lengthy homology, it is known that all three molecules bind to human CTLA-4 and CD28. Thus, there is most likely a common, or closely homologous region shared by the three molecules that may be either contiguous or conformational. This region may constitute the binding site of the B7.1 and B7.2 molecules to their counter-receptors. Antibodies raised against these epitopes could potentially inhibit the interaction of B7 with its counter-receptor on the T cell. Furthermore, antibodies that cross-reacted with this region on both B7.1 and B7.2 molecules would potentially have practical advantages over antibodies directed against B7.1 or B7.2 separately.

2. Blockade of the B7/CD28 Interaction

Blocking of the B71CD28 interaction offers the possibility of inducing specific immunosuppression, with potential for generating long lasting antigen-specific therapeutic effects. Antibodies or agents that temporarily prevent this interaction may be useful, specific and safe clinical immunosuppressive agents, with potential for generating long term antigen-specific therapeutic effects.

Antibodies to either B7.1 or B7.2 have been shown to block T cell activation, as measured by the inhibition of IL-2 production in vitro (DeBoer, M., P. Parren, J. Dove, F. Ossendorp, G. van der Horst, and J. Reeder (1992), "Functional Characterization of a Novel Anti-B7 Monoclonal Antibody," *Eur. Journal of Immunology* 22:3071-3075; Azuma, M., H. Yssel, J. H. Phillips, H. Spits, and L. L. Lanier (1993), "Functional Expression of B7/BB1 on Activated T Lymphocytes," *J. Exp. Med.* 177:845-850)). However, different antibodies have been shown to vary in their immunosuppressive potency, which may reflect either their affinity or epitope specificity. A possible explanation for this may reside in the ability of some antibodies to block only the binding of B7 to CD28, while promoting apoptosis or some other form of negative signaling through the CTLA-4 receptor in activated T cells. Some antibodies to B7.1 or B7.2 may, in fact, hinder the activity of CTLA-4 by cross-reacting with the CTLA-4 binding domain. CTLA-4Ig fusion protein and anti-CD28 Fabs were shown to have similar effects on the down regulation of IL-2 production.

In vivo administration of a soluble CTLA-4Ig fusion protein has been shown to suppress T cell dependent antibody responses in mice (Linsley, P. S., J. L. Greene, P. Tan, J. Bradshaw, J. A. Ledbetter, C. Anasetti, and N. K. Damle (1992), "Coexpression and Functional Cooperation of CTLA-4 and CD28 on Activated T Lymphocytes," *J. Exp. Med.* 176:1595-1604; Lin, H., S. F. Builing, P. S. Linsley, R. O. Wei, C. D. Thompson, and L. A. Turka (1993), "Long-term Acceptance of Major Histocompatibility Complex Mismatched Cardiac Allografts Induced by CTLA-4-Ig Plus Donor Specific Transfusion," *J. Exp. Med.* 178:1801) and, furthermore, larger doses were also able to suppress responses to a second immunization, demonstrating the feasibility of this approach for the treatment of antibody mediated autoimmune disease. In addition, CTLA-4Ig was able to prevent pancreatic islet cell rejection in mice by directly inhibiting the interaction of T cells and B7.1/B7.2 antigen presenting cells (Lenschow, D. J., G. H. Su, L. A. Zuckerman, N. Nabavi, C. L. Jellis, G. S. Gray, J. Miller, and J. A. Bluestone (1993), "Expression and Functional Significance of an Additional Ligand for CTLA-4," *Proc. Natl. Acad. Sci., USA* 90:11054-11058). In this case, long term donor specific tolerance was achieved.

3. Recombinant Phage Display Technology for Antibody Selection

To date, no monoclonal antibodies which cross-react with both B7.1 and B7.2 have been reported. Furthermore, no monoclonal antibodies which are specific to B7.1 or B7.2 and which also recognize specific sites on the antigens which are restricted to co-activation receptor CD28 binding have been reported. Or alternatively, no monoclonal antibodies which are specific to B7.1 or B7.2 and which recognize specific sites on the antigens which are exclusive of CTLA-4 receptor binding have been reported. As discussed supra, such antibodies would potentially be highly desirable as immunosuppressants.

Phage display technology is beginning to replace traditional methods for isolating antibodies generated during the immune response, because a much greater percentage of the immune repertoire can be assessed than is possible using traditional methods. This is in part due to PEG fusion inefficiency, chromosomal instability, and the large amount of tissue culture and screening associated with heterohybridoma production. Phage display technology, by contrast, relies on molecular techniques for potentially capturing the entire repertoire of immunoglobulin genes associated with the response to a given antigen.

This technique is described by Barbas et al, *Proc. Natl. Acad. Sci., USA* 88:7978-7982 (1991). Essentially, immunoglobulin heavy chain genes are PCR amplified and cloned into a vector containing the gene encoding the minor coat protein of the filamentous phage M13 in such a way that a heavy chain fusion protein is created. The heavy chain fusion protein is incorporated into the M13 phage particle together with the light chain genes as it assembles. Each recombinant phage contains, within its genome, the genes for a different antibody Fab molecule which it displays on its surface. Within these libraries, in excess of $10^6$ different antibodies can be cloned and displayed. The phage library is panned on antigen coated microliter wells, non-specific phage are washed off, and antigen binding phage are eluted. The genome from the antigen-specific clones is isolated and the gene III is excised, so that antibody can be expressed in soluble Fab form for further characterization. Once a single Fab is selected as a potential therapeutic candidate, it may easily be converted to a whole antibody. A previously described expression system for converting Fab sequences to whole antibodies is IDEC's mammalian expression vector NEOSPLA. This vector contains either human gamma 1 or gamma 4 constant region genes. CHO cells are transfected with the NEOSPLA vectors and after amplification this vector system has been reported to provide very high expression levels (>30 pg/cell/day) can be achieved.

4. PRIMATIZED® Antibodies

Another highly efficient means for generating recombinant antibodies is disclosed by Newman (1992), Biotechnology 10, 1455-1460. More particularly, this technique results in the generation of PRIMATIZED® antibodies which contain monkey variable domains and human constant sequences. This reference is incorporated by reference in its entirety herein.

Moreover, this technique is also described in commonly assigned U.S. Ser. No. 08/379,072, filed on Jan. 25, 1995, now U.S. Pat. No. 5,658,570, which is a continuation of U.S. Ser. No. 07/912,292, filed Jul. 10, 1992, which is a continuation-in-part of U.S. Ser. No. 07/856,281, filed Mar. 23, 1992, which is a continuation-in-part of U.S. Ser. No. 07/735,064, filed Jul. 25, 1991. U.S. Pat. No. 5,658,570, and the parent applications thereof are incorporated by reference in their entirety herein.

This technique modifies antibodies such that they are not antigenically rejected upon administration in humans. This technique relies on immunization of cynomolgus monkeys with human antigens or receptors. This technique was developed to create high affinity monoclonal antibodies directed to human cell surface antigens.

Identification of macaque antibodies to human B7.1 and B7.2 by screening of phage display libraries or monkey heterohybridomas obtained using B lymphocytes from B7.1 and/or B7.2 immunized monkeys is also described in commonly assigned U.S. application Ser. No. 08/487,550, filed Jun. 7, 1995, incorporated by reference in its entirety herein. More specifically, Ser. No. 08/487,550 provides four monoclonal antibodies 7B6, 16C10, 7C10 and 20C9 which inhibit the B7:CD28 pathway and thereby function as effective immunosuppressants.

Antibodies generated in the manner described by these co-assigned applications have previously been reported to display human effector function, have reduced immunogenicity, and long serum half-life. The technology relies on the fact that despite the fact that cynomolgus monkeys are phylogenetically similar to humans, they still recognize many human proteins as foreign and therefore mount an immune response. Moreover, because the cynomolgus monkeys are phylogenetically close to humans, the antibodies generated in these monkeys have been discovered to have a high degree of amino acid homology to those produced in humans. Indeed, after sequencing macaque immunoglobulin light and heavy chain variable region genes, it was found that the sequence of each gene family was 85-98% homologous to its human counterpart (Newman et al, (1992), Id.). The first antibody generated in this way, an anti-CD4 antibody, was 91-92% homologous to the consensus sequence of human immunoglobulin framework regions. Newman et al, *Biotechnology* 10:1458-1460 (1992).

Monoclonal antibodies specific to the human B7 antigen have been previously described in the literature. For example, Weyl et al, *Hum. Immunol.* 31(4), 271-276 (1991) describe epitope mapping of human monoclonal antibodies against HLA-B-27 using natural and mutated antigenic variants. Also, Toubert et al, *Clin. Exp. Immunol.* 82(1), 16-20 (1990) describe epitope mapping of an HLA-B27 monoclonal antibody that also reacts with a 35-KD bacterial outer membrane protein. Also, Valle et al, *Immunol.* 69(4), 531-535 (1990) describe a monoclonal antibody of the IgG1 subclass which recognizes the B7 antigen expressed in activated B cells and HTLV-1-transformed T cells. Further, Toubert et al, *J. Immunol.* 141(7), 2503-9 (1988) describe epitope mapping of HLA-B27 and HLA-B7 antigens using intradomain recombinants constructed by making hybrid genes between these two alleles in *E. coli*.

High expression of B7 antigen has been correlated to autoimmune diseases by some researchers. For example, lonesco-Tirgoviste et al, *Med. Interre* 24(1), 11-17 (1986) report increased B7 antigen expression in type 1 insulin-dependent diabetes. Also, the involvement of B7 antigen expression on dermal dendritic cells obtained from psoriasis patients has been reported. (Nestle et al, *J. Clin. Invest.* 94(1), 202-209 (1994)).

Further, the inhibition of anti-HLA-B7 alloreactive CTL using affinity-purified soluble HLA-B7 has been reported in the literature. (Zavazava et al, *Transplantation* 51(4), 838-42 (1991)). Further, the use of B7 receptor soluble ligand, CTLA-4-Ig to block B7 activity (See, e.g., Lenschow et al, *Science* 257, 789, 7955 (1992)) in animal models and a B7.1-Ig fusion protein capable of inhibiting B7 has been reported.

Evidence is provided in this disclosure for the identification of monoclonal antibodies which recognize specific sites on the B7.1 antigen which are restricted to CD28 receptor binding. Furthermore, evidence is presented herein for the identification of antibodies which recognize sites on the B7.1 antigen which are exclusive of CTLA-4 receptor binding. Thus, evidence is presented herein to support the existence of unique antigen binding sites on the human B7.1 (CD80) co-stimulatory antigen. The sites claimed are identified by anti-B7.1 PRIMATIZED® antibodies and evidence is presented which confirms binding to a site of interaction on the B7.1 antigen which is restricted to binding with the co-activation receptor CD28.

SUMMARY AND OBJECTS OF THE INVENTION

An object of the invention is to identify novel antibodies which are specific to human B7.1 antigen. More specifically, it is an object of the invention to identify antibodies which are specific to human B7.1 antigen and which are also capable of inhibiting the binding of B7.1 to a CD28 receptor. It is also an object of this invention to identify antibodies which are specific to human B7.1 antigen and which are not capable of inhibiting the binding of B7.1 to a CTLA-4 receptor. Thus, an object of this invention is to identify antibodies which recognize specific sites on the B7.1 antigen, wherein the recognized sites are restricted to CD28 receptor binding and which are exclusive of CTLA-4 receptor binding.

It is a further object of the invention to identify antibodies which are specific to human B7.1 antigen and which fail to recognize human B7.2 antigen.

It is another object of the invention to identify monoclonal antibodies and PRIMATIZED® forms thereof which recognize specific sites on the human B7.1 antigen and which inhibit IL-2 production and T cell proliferation and which function as effective immunosuppressants. More specifically, it is an object of this invention to identify antibodies which are specific to B7.1 and which are capable of inhibiting IL-2 production.

It is another object of the invention to provide monoclonal antibodies and PRIMATIZED® forms thereof which inhibit antigen driven responses in donor spleen cell cultures, e.g., antigen specific IgG responses, IL-2 production and cell proliferation.

It is another specific object of the invention to identify particular monoclonal antibodies specific to human B7.1 antigen and PRIMATIZED® forms thereof having advantageous properties, i.e., affinity, immunosuppressive activity, which are useful as therapeutics. More specifically, these antibodies and PRIMATIZED® forms thereof are to be used, e.g., as immunosuppressants, i.e., to block antigen driven immune responses, to treat autoimmune diseases such as psoriasis, rheumatoid arthritis, systemic erythematosus (SLE), type 1 diabetes mellitus, idiopathic thrombocytopenia purpura (ITP), allergy, inflammatory bile disease, and to prevent organ rejection.

It is another object of the invention to provide pharmaceutical compositions containing one or more monoclonal antibodies specific to human B7.1 antigen or PRIMATIZED® forms thereof, and a pharmaceutically acceptable carrier or excipient. These compositions will be used, e.g., as immunosuppressants to treat autoimmune diseases, e.g., idiopathic thrombocytopeniapurpura (ITP) and systemic lupus erythematosus (SLE), to block antigen driven immune responses, and to prevent organ rejection in transplant recipients.

It is another object of the invention to provide novel methods of therapy by administration of therapeutically effective amounts of one or more or PRIMATIZED® monoclonal antibodies which specifically bind to human B7.1 antigen. Such therapeutic methods are useful for treatment of diseases treatable by inhibition of the B7:CD28 pathway, e.g., autoimmune diseases such as idiopathic thrombocytopenia purpura (ITP), systemic lupus erythematosus (SLE), type 1 diabetes mellitus, psoriasis, rheumatoid arthritis, multiple sclerosis, aplastic anemia, as well as for preventing rejection in transplantation subjects.

It is still another object of the invention to provide transfectants, e.g., CHO cells, which express at least the variable heavy and light domains of monoclonal antibodies specific to the human B7.1 antigen.

DEFINITIONS

The following terms are defined so that the invention may be more clearly understood.

Depleting antibody—an antibody which kills activated B cells or other antigen presenting cells.

Non-depleting antibody—an antibody which blocks the co-stimulatory action of B7 and T cell activating ligands CD28 and CTLA-4. Thus, it anergizes but does not eliminate the antigen presenting cell.

PRIMATIZED® antibody—a recombinant antibody which has been engineered to contain the variable heavy and light domains of a monkey antibody, in particular, a cynomolgus monkey antibody, and which contains human constant domain sequences, preferably the human immunoglobulin gamma 1 or gamma 4 constant domain (or PE variant). The preparation of such antibodies is described in Newman et al, (1992), "Primatization of Recombinant Antibodies for Immunotherapy of Human Diseases: A Macaque/Human Chimeric Antibody Against Human CDH", Biotechnology 10:1458-1460; also in commonly assigned U.S. Ser. No. 08/379,072, now U.S. Pat. No. 5,658,570, both of which are incorporated by reference in their entirety herein. These antibodies have been reported to exhibit a high degree of homology to human antibodies, i.e., 85-98%, display human effector functions, have reduced immunogenicity, and may exhibit high affinity to human antigens.

B7 antigens—B7 antigens in this application include, e.g., human B7, B7.1 and B7.2 antigens. These antigens bind to CD28 and/or CTLA-4. These antigens have a co-stimulatory role in T cell activation. Also, these B7 antigens all contain extracellular immunoglobulin superfamily V and C-like domains, a hydrophobic transmembrane region and a cytoplasmic tail (See, Freeman et al, *Science* 262:909, (1993)), and are heavily glycosylated.

Anti-B7 antibodies—Antibodies, preferably monkey monoclonal antibodies or PRIMATIZED® forms thereof, which specifically bind human B7 antigens, e.g., human B7.1 and/or B7.2 antigen with a sufficient affinity to block the B7:CD28 interaction, but do not block the B7/CTLA-4 receptor interaction and thereby induce immunosuppression.

BRIEF DESCRIPTION OF THE FIGURES

FIG. 3A depicts the amino acid and nucleic acid sequence of a PRIMATIZED® form of the light chain of 7C10 (SEQ ID NOS: 1-2).

FIGS. 3B and 3C depict the amino acid and nucleic acid sequence of a PRIMATIZED® form of the light chain of 7C10 (SEQ ID NOS: 3-4).

FIG. 4A depicts the amino acid and nucleic acid sequence of a PRIMATIZED® form of the light chain of 7B6 (SEQ ID NOS: 5-6).

FIGS. 4B and 4C depict the amino acid and nucleic acid sequence of a PRIMATIZED® form of the heavy chain of 7B6 (SEQ ID NOS: 7-8).

FIG. 5A depicts the amino acid and nucleic acid sequence of a PRIMATIZED® light chain 16C10 (SEQ ID NOS: 9-10).

FIGS. 5B and 5C depict the amino acid and nucleic acid sequence of a PRIMATIZED® heavy chain 16C10 (SEQ ID NOS: 11-12).

DETAILED DESCRIPTION OF THE INVENTION

As described above, the present invention relates to the identification of monoclonal antibodies or PRIMATIZED® forms thereof which are specific to human B7.1 antigen and which are capable of inhibiting the binding of B7.1 to a CD28 receptor and which are not capable of inhibiting the binding of B7.1 to a CTLA-4 receptor. Blocking of the primary activation site between CD28 and B7.1 (CD80) with the identified antibodies while allowing the combined antagonistic effect on positive co-stimulation with an agnostic effect on negative signaling will be a useful therapeutic approach for intervening in relapsed forms of autoimmune disease. The functional activity of the identified antibodies is defined by blocking the production of the T cell stimulatory cytokine IL-2. Identified antibodies have demonstrated the ability to block the production of IL-2 in excess of 50%, in spite of the existence of a second actuating ligand B7.2, suggesting an alternate mechanism of action exists which is not typical of the observed effects of other anti-B7.1 antibodies defined in the literature.

Manufacture of novel monkey monoclonal antibodies which specifically bind human B7.1 and/or human B7.2 antigen, as well as PRIMATIZED® antibodies derived therefrom is described in co-pending U.S. application Ser. No. 08/487,550, and as set forth herein. These antibodies possess high affinity to human B7.1 and/or B7.2 and therefore may be used as immunosuppressants which inhibit the B7:CD86 pathway.

Preparation of monkey monoclonal antibodies will preferably be effected by screening of phage display libraries or by preparation of monkey heterohybridomas using B lymphocytes obtained from B7 (e.g., human B7.1 and/or B7.2) immunized monkeys.

As noted, the first method for generating anti-B7 antibodies involves recombinant phage display technology. This technique is generally described supra.

Figure 1:
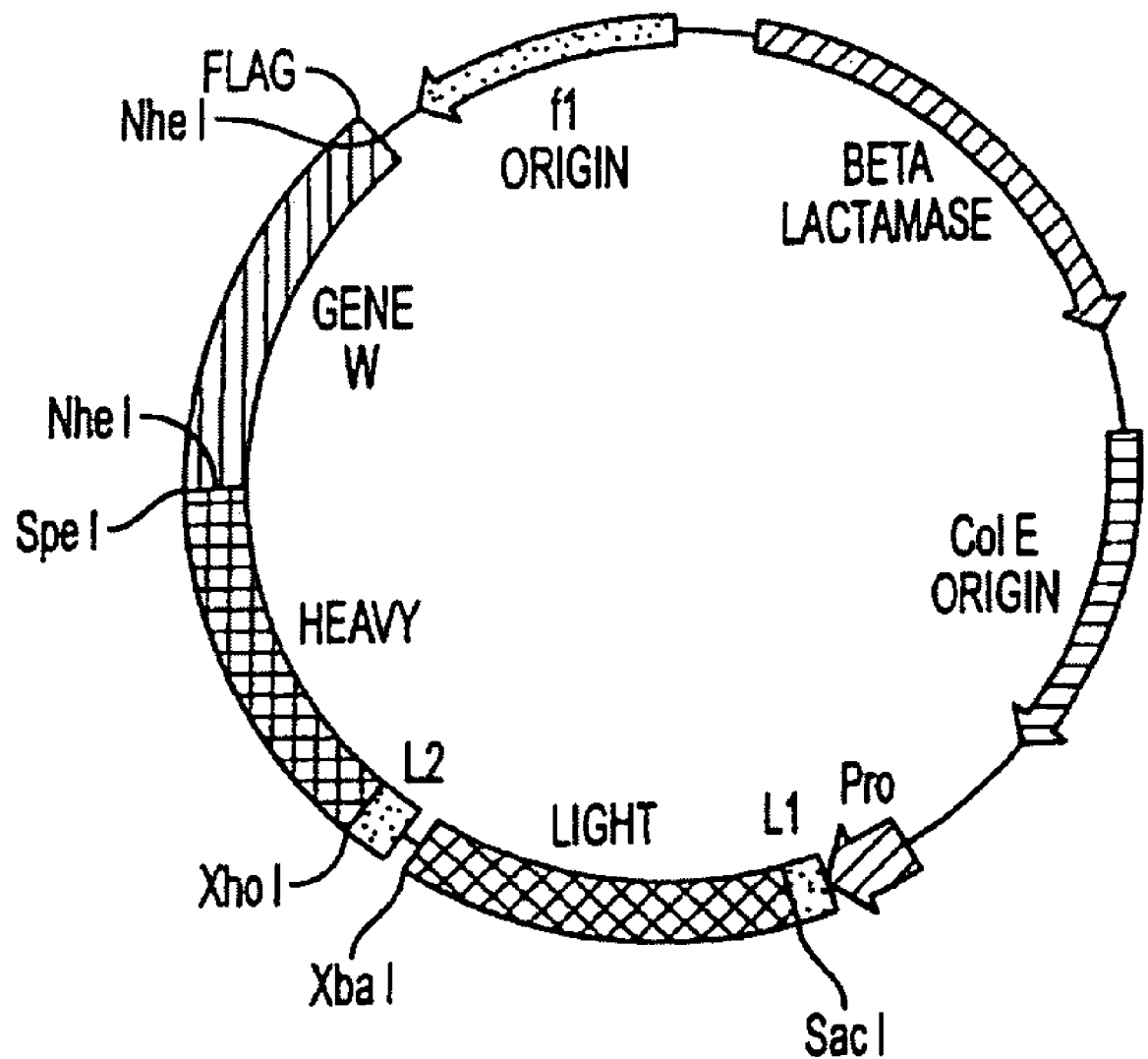
FIG. 1 depicts the pMS vector used to screen recombinant immunoglobulin libraries produced against B7 displayed on the surface of filamentous phage which contains primers based on macaque immunoglobulin sequences.

Essentially, this will comprise synthesis of recombinant immunoglobulin libraries against B7 antigen displayed on the surface of filamentous phage and selection of phage which secrete antibodies having high affinity to B7.1 and/or B7.2 antigen. As noted supra, preferably antibodies will be selected which bind to both human B7.1 and B7.2. To effect such methodology, the present inventors have created a unique library for monkey libraries which reduces the possibility of recombination and improves stability. This vector, PMS, is described in detail infra, and is shown in FIG. 1.

Essentially, to adopt phage display for use with macaque libraries, this vector contains specific primers for PCR amplifying monkey immunoglobulin genes. These primers are based on macaque sequences obtained while developing the PRIMATIZED® technology and databases containing human sequences.

Suitable primers are disclosed in commonly assigned U.S. Pat. No. 5,658,570.

The second method involves the immunization of monkeys, i.e., macaques, against human B7 antigen, preferably against human B7.1 and B7.2 antigen. The inherent advantage of macaques for generation of monoclonal antibodies is discussed supra. In particular, such monkeys, i.e., cynomolgus monkeys, may be immunized against human antigens or receptors. Moreover, the resultant antibodies may be used to make PRIMATIZED® antibodies according to the methodology of Newman et al, Biotechnology 10, 1455-1460 (1992), and Newman et al, commonly assigned U.S. Ser. No. U.S. Pat. No. 5,658,570, which are incorporated by reference in their entirety.

The significant advantage of antibodies obtained from cynomolgus monkeys is that these monkeys recognize many human proteins as foreign and thereby provide for the formation of antibodies, some with high affinity to desired human antigens, e.g., human surface proteins and cell receptors. Moreover, because they are phylogenetically close to humans, the resultant antibodies exhibit a high degree of amino acid homology to those produced in humans. As noted above, after sequencing macaque immunoglobulin light and heavy variable region genes, it was found that the sequence of each gene family was 85-88% homologous to its human counterpart (Newman et al, (1992), Id.).

Essentially, cynomolgus macaque monkeys are administered human B7 antigen, e.g., human B7.1 and/or human B7.2 antigen, B cells are isolated therefrom, e.g., lymph node biopsies are taken from the animals, and B lymphocytes are then fused with KH6/B5 (mouse×human) heteromyeloma cells using polyethylene glycol (PEG). Heterohybridomas secreting antibodies which bind human B7 antigen, e.g., human B7.1 and/or human B7.2 antigen, are then identified.

Antibodies which bind to both B7.1 and B7.2 are desirable because such antibodies potentially may be used to inhibit the interaction of B7.1 and B7.2, as well as B7 with their counter-receptors, i.e., human CTLA-4 and CD28. Antibodies against these epitopes may inhibit the interaction of both human B7.1 and human B7.2 with their counter receptors on the T cell. This may potentially provide synergistic effects.

However, antibodies which bind to only one of human B7 antigen, B7.1 antigen or B7.2 antigen, are also highly desirable because of the co-involvement of these molecules in T cell activation, clonal expansion lymphokine (IL-2) secretion, and responsiveness to antigen. Given that both human B7.1 and B7.2 bind to human CTLA-4 and CD28, it is probable that there is at least one common or homologous region (perhaps a shared conformational epitope or epitopes) to which macaque antibodies may potentially be raised.

The disclosed invention involves the use of an animal which is primed to produce a particular antibody. Animals which are useful for such a process include, but are not limited to, the following: mice, rats, guinea pigs, hamsters, monkeys, pigs, goats and rabbits.

A preferred means of generating human antibodies using SCID mice is disclosed in commonly-owned, co-pending U.S. patent application Ser. No. 08/488,376.

The present inventors elected to immunize macaques against human B7.1 antigen using recombinant soluble B7.1 antigen produced in CHO cells and purified by affinity chromatography using a L307.4 SEPHAROSE® affinity column. However, the particular source of human B7 antigen, human B7.1 antigen or human B7.2 antigen is not critical, provided that it is of sufficient purity to result in a specific antibody response to the particular administered B7 antigen and potentially to other B7 antigens.

The human B7 antigen, human B7.1 antigen (also called CD80) and human B7.2 antigen (also called CD86) genes have been cloned, and sequenced, and therefore may readily be manufactured by recombinant methods.

Preferably, the administered human B7 antigen, human B7.1 antigen and/or human B7.2 antigen will be administered in soluble form, e.g., by expression of a B7, B7.1 or B7.2 gene which has its transmembrane and cytoplasmic domains removed, thereby leaving only the extracellular portion, i.e., the extracellular superfamily V and C-like domains. (See, e.g., Grumet et al, *Hum. Immunol.* 40(3), p. 228-234 (1994), which teaches expression of a soluble form of human B7, which is incorporated by reference in its entirety herein)).

The macaques will be immunized with the B7, B7.1 and/or B7.2 antigen, preferably a soluble form thereof, under conditions which result in the production of antibodies specific thereto. Preferably, the soluble human B7, B7.1 or B7.2 antigen will be administered in combination with an adjuvant, e.g., Complete Freund's Adjuvant (CFA), Alum, Saponin, or other known adjuvants, as well as combinations thereof. In general, this will require repeated immunization, e.g., by repeated injection, over several months. For example, administration of soluble B7.1 antigen was effected in adjuvant, with booster immunizations, over a 3 to 4 month period, with resultant production of serum containing antibodies which bound human B7.1 antigen.

After immunization B cells are collected, e.g., by lymph node biopsies taken from the immunized animals and B lymphocytes fused with KH6/B5 (mouse x human) heteromyeloma cells using polyethylene glycol. Methods for preparation of such heteromyelomas are known and may be found in U.S. Pat. No. 5,658,570, by Newman et al.

Heterohybridomas which secrete antibodies which bind human B7, B7.1 and/or B7.2 are then identified. This may be effected by known techniques. For example, this may be determined by ELISA or radioimmunoassay using enzyme or radionucleotide labelled human B7, B7.1 and/or B7.2 antigen.

Cell lines which secrete antibodies having the desired specificity to human B7, B7.1 and/or B7.2 antigen are then subcloned to monoclonality.

In the present invention, the inventors screened purified antibodies for their ability to bind to soluble B7.1 antigen coated plates in an ELISA assay, antigen positive B cells, and CHO transfectomas which express human B7.1 antigen on their cell surface. In addition, the antibodies were screened for their ability to block B cell/T cell interactions as measured by IL-2 production and tritiated thymidine uptake in a mixed lymphocyte reaction (MLR), with B7 binding being detected using $^{125}$I-radiolabeled soluble B7.1 (SB7.1).

Also, affinity purified antibodies from macaques were tested for their reactivity against CHO transfectants which expressed B7.1/Ig fusion proteins, and against CHO cells which produced human B7.2 antigen. These results indicated that the B7.1 immune sera bound to the B7.2 transfectomas. Binding of antibodies to B7.2 antigen may be confirmed using soluble B7.2-Ig reagents. As discussed in the examples, this may be effected by producing and purifying B7.2-Ig from CHO transfectomas in sufficient quantities to prepare a B7.2-Ig-SEPHAROSE® affinity column. Those antibodies which cross-react with B7.2 will bind the B7.2-Ig-SEPHAROSE® column.

Cell lines which express antibodies which specifically bind to human B7 antigen, B7.1 antigen and/or B7.2 antigen are then used to clone variable domain sequences for the manufacture of PRIMATIZED® antibodies essentially as described in Newman et al (1992), Id. and Newman et al, U.S. Ser. No. 379,072, filed Jan. 25, 1995, both of which are incorporated by reference herein. Essentially, this entails extraction of RNA therefrom, conversion to cDNA, and amplification thereof by PCR using Ig specific primers. Suitable primers are described in Newman et al, 1992, Id. and in U.S. Ser. No. 379,072. (See, in particular, FIG. 1 of U.S. Ser. No. 379,072).

Figure 2:
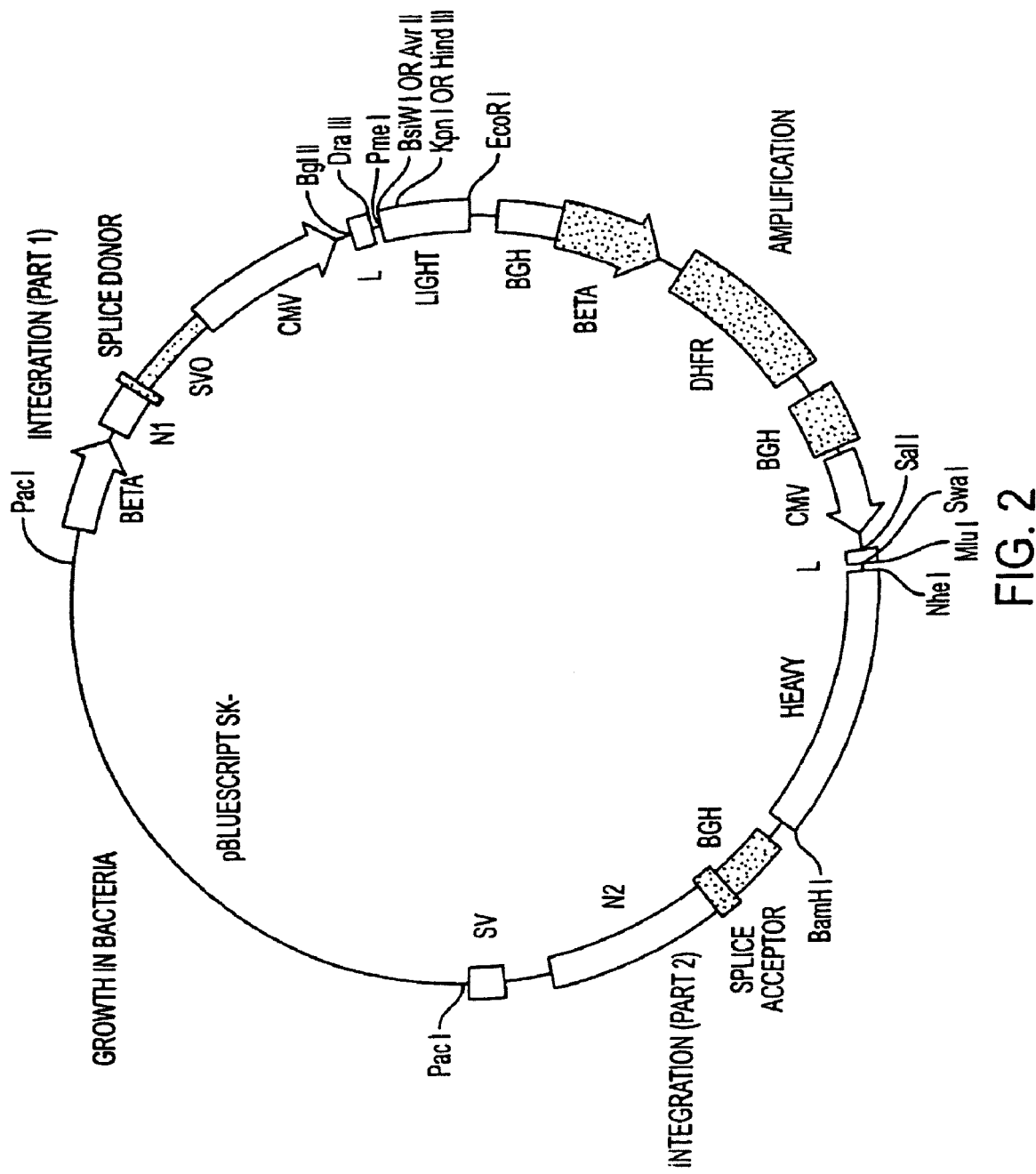
FIG. 2 depicts the NEOSPLA® expression vector used to express the subject PRIMATIZED® antibodies specific to human B7.1 antigen.

The cloned monkey variable genes are then inserted into an expression vector which contains human heavy and light chain constant region genes. Preferably, this is effected using a proprietary expression vector of IDEC, Inc., referred to as NEOSPLA®. This vector is shown in FIG. 2 and contains the cytomegalovirus promoter/enhancer, the mouse beta globin major promoter, the SV40 origin of replication, the bovine growth hormone polyadenylation sequence, neomycin phosphotransferase exon 1 and exon 2, human immunoglobulin kappa or lambda constant region, the dihydrofolate reductase gene, the human immunoglobulin gamma 1 or gamma 4 PE constant region and leader sequence. This vector has been found to result in very high level expression of PRIMATIZED® antibodies upon incorporation of monkey variable region genes, transfection in CHO cells, followed by selection in G418 containing medium and methotrexate amplification.

For example, this expression system has been previously disclosed to result in PRIMATIZED® antibodies having high avidity ($Kd \leq 10^{-10}$ M) against CD4 and other human cell surface receptors. Moreover, the antibodies have been found to exhibit the same affinity, specificity and functional activity as the original monkey antibody. This vector system is substantially disclosed in commonly assigned U.S. Pat. No. 5,658,570, incorporated by reference herein, as well as U.S. Ser. No. 08/149,099, now U.S. Pat. No. 5,736,137, also incorporated by reference in its entirety herein. This system provides for high expression levels, i.e., >30 pg/cell/day.

As discussed infra, the subject inventors have selected four lead candidate monkey monoclonal antibodies which specifically bind the B7.1 antigen. These monkey monoclonal antibodies are referred to herein as 7B6, 16C10, 7C10 and 20C9.

As discussed in greater detail infra, these antibodies were evaluated for their ability to block B cell/T cell interactions as measured by IL-2 production and tritiated thymidine uptake in a mixed lymphocyte reaction for T cell binding experiments for T cell binding, human buffy coat peripheral blood lymphocytes were cultured for 3-6 days in the presence of PHA stimulator. B7 binding was radioassayed using $^{125}$I-radiolabeled soluble B7.1. The observed results indicate that all of these antibodies bind B7.1 antigen with high affinity and effectively block B cell/T cell interactions as evidenced by reduced IL-2 production and reduced proliferation of mixed lymphocyte cultures.

The properties of these particular monkey monoclonal antibodies are summarized below:

1. Scatchard analysis showed that the apparent affinity constants (Kd) for the monkey antibodies binding to B7-Ig coated plates were approximated to be:

| a: | 7C10: | $6.2 \times 10^{-9}$ M |
|---|---|---|
| b: | 16C10: | $8.1 \times 10^{-9}$ M |
| c: | 7B6: | $10.7 \times 10^{-9}$ M |
| d: | 20C9: | $16.8 \times 10^{-9}$ M |

2. The antibodies were tested in vitro in a mixed lymphocyte reaction assay (MLR). The MLR showed that all 4 anti-B7.1 antibodies inhibit IL-2 production to different extents as shown by the following $IC_{50}$ values:

| a: | 7B6: | 5.0 µg/M |
|---|---|---|
| b: | 16C10: | <0.1 µg/M |
| c: | 20C9: | 2.0 µg/M |
| d: | 7C10: | 5.0 µg/M |

3. The monkey anti-B7.1 antibodies were tested for their ability to bind B7 on human peripheral blood lymphocytes (PBL). FACS analysis showed that all 4 monkey antibodies tested positive.
4. Monkey antibodies 16C10, 7B6, 7C10 and 20C9 were tested for Clq binding by FACS analysis. Results showed 7C10 monkey Ig had strong human Clq binding after incubating with B7.1 CHO-transfected cells. 16C10 was positive, while 20C9 and 7B6 monkey antibodies were negative.
5. To select an animal model for path-tox studies, the monkey antibodies were tested with animal blood from different species. It was determined that the monkey anti-B7.1 antibodies cross-reacted with human, chimpanzee.

Based on these properties, it would appear that three monkey monoclonal antibodies possess the most advantageous properties, 16C10, 7C10 and 20C9, with 16C10 and 7C10 being somewhat better than 20C9.

Using the techniques described supra, and in commonly assigned U.S. Pat. No. 5,658,570, the present inventors have cloned the variable domains of 7C10, 7B6 and 16C 10, and provide the amino acid and nucleic acid sequences of PRIMATIZED® forms of the 7C10 light chain, 7C10 heavy chain, 7B6 light chain, 7B6 heavy chain, 16C10 light chain and 16C10 heavy chain. These amino acid and nucleic acid sequences may be found in FIGS. 3A (SEQ ID NOS: 1-2), 3B-3C (SEQ ID NOS: 3-4), 4A (SEQ ID NOS: 5-6), 4B-4C (SEQ ID NOS: 7-8), 5A (SEQ ID NOS: 9-10) and 5B-5C (SEQ ID NOS: 11-12). The DNA and amino acid sequence for the human gamma 1, gamma 4 constant domain may be found in U.S. Pat. No. 5,658,570.

As discussed supra, these primatized antibodies are preferably expressed using the NEOSPLA expression vector shown in FIG. 2 which is substantially described in commonly assigned U.S. Pat. No. 5,658,570, and U.S. Pat. No. 5,736,137, incorporated by reference herein in its entirety.

As previously noted, the subject PRIMATIZED® antibodies will preferably contain either the human immunoglobulin gamma 1 or gamma 4 constant region, with gamma 4 preferably mutated at two positions to create gamma 4 PE. The gamma 4 PE mutant contains two mutations, a glutamic acid in the CH2 region introduced to eliminate residual FCR binding, and a proline substitution in the hinge region, intended to enhance the stability of the heavy chain disulfide bond interaction. (See, Alegre et al, J. Immunol. 148, 3461-3468 (1992); and Angel et al, Mol. Immunol. 30, 105-158 (1993), both of which are incorporated by reference herein).

Whether the subject PRIMATIZED® antibodies contain the gamma 1, gamma 4 or gamma 4 PE constant region largely depends on the particular disease target. Preferably, depleting and non-depleting PRIMATIZED® IgG1 and IgG4 antibodies are created and tested against specific disease targets.

Given the described binding and functional properties of the subject monkey monoclonal antibodies, these anti-B7.1 monoclonal antibodies and PRIMATIZED® forms thereof should be well suited as therapeutic agents for blocking the B7:CD28 interaction thereby providing for immunosuppression. In particular, given their high affinity to B7.1 antigen and ability to block B cell/T cell interactions as measured by IL-2 production and tritiated thymidine uptake in mixed lymphocyte culture as well as their ability to effectively inhibit antigen driven responses in donor spleen cell cultures as shown by reduced antigen specific IgG responses, IL-2 production and cell proliferation, these monkey monoclonal antibodies and PRIMATIZED® forms thereof should function as effective immunosuppressants which modulate the B7:CD28 pathway. This is significant for the treatment of many diseases wherein immunosuppression is therapeutically desirable, e.g., autoimmune diseases, to inhibit undesirable antigen specific IgG responses, and also for prevention of organ rejection and graft-versus-host disease. Essentially, the subject antibodies will be useful in treating any disease wherein suppression of the B7:CD28 pathway is therapeutically desirable.

Key therapeutic indications for the subject anti-B7.1 antibodies include, by way of example, autoimmune diseases such as idiopathic thrombocytopenia purpura (ITP), systemic lupus erythematosus (SLE), type 1 diabetes mellitus, multiple sclerosis, aplastic anemia, psoriasis, allergy, inflammatory bile disease and rheumatoid arthritis.

Another significant therapeutic indication of the subject anti-B7.1 antibodies is for prevention of graft-versus-host-disease (GVHD) during organ transplant and bone marrow transplant (BMT). The subject antibodies may be used to induce host tolerance to donor-specific alloantigens and thereby facilitate engrafiment and reduce the incidence of graft rejection. It has been shown in a murine model of allogeneic cardiac transplantation that intravenous administration of CTLA4-Ig can result in immunosuppression or even induction of tolerance to alloantigen. (Lin et al, J. Exp. Med. 178:1801, 1993; Torka et al, Proc. Natl. Acad. Sci., USA 89:11102, 1992). It is expected that the subject PRIMATIZED® anti-B7.1 antibodies will exhibit similar or greater activity.

Antibodies produced in the manner described above, or by equivalent techniques, can be purified by a combination of affinity and size exclusion chromatography for characterization in functional biological assays. These assays include determination of specificity and binding affinity as well as effector function associated with the expressed isotype, e.g., ADCC, or complement fixation. Such antibodies may be used as passive or active therapeutic agents against a number of human diseases, including B cell lymphoma, infectious diseases including viral diseases such as HIV/AIDS, autoimmune and inflammatory diseases, and transplantation. The antibodies can be used either in their native form, or as part of an antibody/chelate, antibody/drug or antibody/toxin complex. Additionally, whole antibodies or antibody fragments ($Fab_2$, Fab, Fv) may be used as imaging reagents or as potential vaccines or immunogens in active immunotherapy for the generation of anti-idiotypic responses.

The amount of antibody useful to produce a therapeutic effect can be determined by standard techniques well known to those of ordinary skill in the art. The antibodies will generally be provided by standard technique within a pharmaceutically acceptable buffer, and may be administered by any desired route. Because of the efficacy of the presently claimed antibodies and their tolerance by humans it is possible to administer these antibodies repetitively in order to combat various diseases or disease states within a human.

The anti-B7.1 antibodies (or fragments thereof) of this invention are useful for inducing immunosuppression, i.e., inducing a suppression of a human's or animal's immune system. This invention therefore relates to a method of prophylactically or therapeutically inducing immunosuppression in a human or other animal in need thereof by administering an effective, non-toxic amount of such an antibody of this invention to such human or other animal.

The ability of the compounds of this invention to induce immunosuppression has been demonstrated in standard tests used for this purpose, for example, a mixed lymphocyte reaction test or a test measuring inhibition of T-cell proliferation measured by thymidine uptake.

For example, in vitro assays were conducted that measured cell growth and activating cytokines produced in response to co-stimulatory signals that activate CD4+ T cells. The production and secretion of these cytokines occurs naturally in T cells under conditions where a primary and secondary signal is generated through interactions between T cells and antigen presenting cells. Normally a primary signal is initiated through interaction of a antigen specific T cell receptor and MHC Class II molecules bearing the specific antigen on antigen presenting cells. A secondary or co-stimulatory signal is required to obtain maximal activation of T cells. Several T cell co-stimulatory receptors have been identified that drive the production of various cytokines, and up-regulate other cell surface receptors that function in growth and differentiation of T cells and hematopoietic accessory cells. Some of the known signaling T cell co-stimulatory receptors are CD28, CD 1, CD54 and CD40L. Sustained adhesion and prolonged interactions through these cell surface molecules result in secretion of IL-2 and various secondary inflammatory cytokines that control numerous immuno-regulatory functions.

The study of T cell interactions can be complex due to the presence of numerous accessory cell types capable of mediating redundant or interdependent co-stimulatory effects.

The CD281B7 receptor ligand interaction is considered to be the key secondary response element between antigen presenting cells and CD4+ helper T cells in the immune response cascade. After a primary signal is generated between antigen specific T cell receptors and antigen/MHC class II complexes, two types of B7 molecules, B7-1 (CD80) and B7-2, (CD86) are up-regulated and establish a membrane signaling event through binding to CD28 receptor. These signals drive the gene expression of various cytokines beginning with the production of IL-2. The detection of secreted IL-2, cell proliferation and various cell surface activation markers including the receptor for IL-2 are clear indicators that co-stimulation has occurred and cells are beginning to divide and differentiate to maturity. T cells may be influenced or driven down different maturation pathways depending on many complex internal and external factors through mechanisms that are poorly understood. The CD28/B7 interaction was first identified as an adhesion event when a B7 specific antibody was identified that blocked adhesion between B and T cell types. CD28 is known to affect in vivo immune responses by functioning both as a cell adhesion molecule linking B and T lymphocytes and as the surface component of a novel signal transduction pathway (June et al. 1990, *Immunology Today*, 11: 211-216). As a result, several monoclonal antibodies that recognize either CD28 or B7 are capable of blocking both adhesion and signaling events. Blocking of either event would lead directly or indirectly to reduced signaling through the CD28 receptor and would result in reduced IL-2 production, proliferation and the appearance of secondary cytokines.

More specifically, the present inventors have isolated certain novel antibodies, the activity of which apparently does not involve directly blocking of signal transduction as demonstrated through the use of CTLA-4Ig, a soluble receptor fusion protein that co-recognizes both B7 receptors. Evidence is provided herein that a PRIMATIZED® antibody according to the invention, referred to as IDEC-114 blocks adhesion of antigen presenting cells to T cells thereby blocking an upstream event prior to signaling that under certain conditions, possibly related to B7 receptor density, is capable of influencing T cell activation. Evidence is provided through use of an in vitro assay that establishes distinct differences between the mechanism of action of IDEC-114 and other anti-CD80 antibodies as well as CTLA-4Ig. The in vitro assay employed in these experiments was designed to reduce the number of complex interactions provided by accessory cells, by using a purified CD4+ T cell population and replacing accessory cells with a non-cellular co-stimulatory system. This cell activating system obviates the need for antigen presenting cells by using latex micospheres containing immobilized antibody to the CD3 antigen to deliver a suboptimal primary signal to the T cell. This system when presented along with B7 (CD80) co-stimulatory ligand provides a very potent signal through the CD28 receptor that initiates gene expression resulting in production of IL-2, T cell growth and other pro-inflammatory cytokines.

The fact that the antibodies of this invention have utility in inducing immunosuppression indicates that they should be useful in the treatment or prevention of resistance to or rejection of transplanted organs or tissues (e.g., kidney, heart, lung, bone marrow, skin, cornea, etc.); the treatment or prevention of autoimmune, inflammatory, proliferative and hyperproliferative diseases, and of cutaneous manifestations of immunologically medicated diseases (e.g., rheumatoid arthritis, lupus erythematosus, systemic lupus erythematosus, Hashimotos thyroiditis, multiple sclerosis, myasthenia gravis, type 1 diabetes, uveitis, nephrotic syndrome, psoriasis, atopical dermatitis, contact dermatitis and further eczematous dermatitides, seborrheic dermatitis, Lichen planus, Pemplugus, bullous pemphigus, Epidermolysis bullosa, urticaria, angioedemas, vasculitides, erythema, cutaneous eosinophilias, Alopecia areata, etc.); the treatment of reversible obstructive airways disease, intestinal inflammations and allergies (e.g., inflammatory bile disease, Coeliac disease, proctitis, eosinophilia gastroenteritis, mastocytosis, Crohn's disease and ulcerative colitis), food-related allergies (e.g., migraine, rhinitis and eczema), and other types of allergies.

One skilled in the art would be able, by routine experimentation, to determine what an effective, non-toxic amount of antibody would be for the purpose of inducing immunosuppression. Generally, however, an effective dosage will be in the range of about 0.05 to 100 milligrams per kilogram body weight per day.

The antibodies (or fragments thereof) of this invention should also be useful for treating tumors in a mammal. More specifically, they should be useful for reducing tumor size, inhibiting tumor growth and/or prolonging the survival time of tumor-bearing animals. Accordingly, this invention also relates to a method of treating tumors in a human or other animal by administering to such human or animal an effective, non-toxic amount of an antibody. One skilled in the art would be able, by routine experimentation, to determine what an effective, non-toxic amount of anti-B7 antibody would be for the purpose of treating carcinogenic tumors. Generally, however, an effective dosage is expected to be in the range of about 0.05 to 100 milligrams per kilogram body weight per day.

The antibodies of the invention may be administered to a human or other animal in accordance with the aforementioned methods of treatment in an amount sufficient to produce such effect to a therapeutic or prophylactic degree. Such antibodies of the invention can be administered to such human or other animal in a conventional dosage form prepared by combining the antibody of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables.

The route of administration of the antibody (or fragment thereof) of the invention may be oral, parenteral, by inhalation or topical. The term parenteral as used herein includes intravenous, intraperitoneal, intramuscular, subcutaneous, rectal or vaginal administration. The subcutaneous and intramuscular forms of parenteral administration are generally preferred.

The daily parenteral and oral dosage regimens for employing compounds of the invention to prophylactically or therapeutically induce immunosuppression, or to therapeutically treat carcinogenic tumors will generally be in the range of about 0.05 to 100, but preferably about 0.5 to 10, milligrams per kilogram body weight per day.

The antibodies of the invention may also be administered by inhalation. By "inhalation" is meant intranasal and oral inhalation administration. Appropriate dosage forms for such administration, such as an aerosol formulation or a metered dose inhaler, may be prepared by conventional techniques. The preferred dosage amount of a compound of the invention to be employed is generally within the range of about 10 to 100 milligrams.

The antibodies of the invention may also be administered topically. By topical administration is meant non-systemic administration and includes the application of an antibody (or fragment thereof) compound of the invention externally to the epidermis, to the buccal cavity and instillation of such an antibody into the ear, eye and nose, and where it does not significantly enter the blood stream. By systemic administration is meant oral, intravenous, intraperitoneal and intramuscular administration. The amount of an antibody required for therapeutic or prophylactic effect will, of course, vary with the antibody chosen, the nature and severity of the condition being treated and the animal undergoing treatment, and is ultimately at the discretion of the physician. A suitable topical dose of an antibody of the invention will generally be within the range of about 1 to 100 milligrams per kilogram body weight daily.

Formulations

While it is possible for an antibody or fragment thereof to be administered alone, it is preferable to present it as a pharmaceutical formulation. The active ingredient may comprise, for topical administration, from 0.001% to 10% w/w, e.g., from 1% to 2% by weight of the formulation, although it may comprise as much as 10% w/w but preferably not in excess of 5% w/w and more preferably from 0.1% to 1% w/w of the formulation.

The topical formulations of the present invention, comprise an active ingredient together with one or more acceptable carrier(s) therefor and optionally any other therapeutic ingredients(s). The carrier(s) must be "acceptable" in the sense of being compatible with the other ingredients of the formulation and not deleterious to the recipient thereof.

Formulations suitable for topical administration include liquid or semi-liquid preparations suitable for penetration through the skin to the site of where treatment is required, such as liniments, lotions, creams, ointments or pastes, and drops suitable for administration to the eye, ear or nose.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 90°-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogols. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

The subject anti-B7.1 antibodies or fragments thereof may also be administered in combination with other moieties which modulate the B7:CD28 pathway. Such moieties include, by way of example, cytokines such as IL-7 and IL-10, CTLA4-Ig, soluble CTLA-4 and anti-CD28 antibodies and fragments thereof. Also, the subject antibodies may be administered in combination with other immunosuppressants. Such immunosuppressants include small molecules such as cyclosporin A (CSA) and FK506; monoclonal antibodies such as anti-tumor necrosis factor a (anti-TNFa), anti-CD54, anti-CD11, anti-CD11a, and anti-IL-1; and, other soluble receptors such as rTNFa and rIL-1.

It will be recognized by one of skill in the art that the optimal quantity and spacing of individual dosages of an antibody or fragment thereof of the invention will be determined by the nature and extent of the condition being treated, the form, route and site of administration, and the particular animal being treated, and that such optimums can be determined by conventional techniques. It will also be appreciated by one of skill in the art that the optimal course of treatment, i.e., the number of doses of an antibody or fragment thereof of the invention given per day for a defined number of days, can be ascertained by those skilled in the art using conventional course of treatment determination tests.

Without further elaboration, it is believed that one skilled in the art can, using the preceding description, utilize the present invention to its fullest extent. The following formulations are, therefore, to be construed as merely illustrative embodiments and not a limitation of the scope of the present invention in any way.

Capsule Composition

A pharmaceutical composition of this invention in the form of a capsule is prepared by filling a standard two-piece hard gelatin capsule with 50 mg. of an antibody or fragment thereof of the invention, in powdered form, 100 mg. of lactose, 32 mg. of talc and 8 mg. of magnesium stearate.

Injectable Parenteral Composition

A pharmaceutical composition of this invention in a form suitable for administration by injection is prepared by stirring 1.5% by weight of an antibody or fragment thereof of the invention in 10% by volume propylene glycol and water. The solution is sterilized by filtration.

Ointment Composition

Antibody or fragment thereof of the invention 1.0 g.

White soft paraffin to 100.0 g.

The antibody or fragment thereof of the invention is dispersed in a small volume of the vehicle to produce a smooth, homogeneous product. Collapsible metal tubes are then filled with the dispersion.

Topical Cream Composition
  Antibody or fragment thereof of the invention 1.0 g.
  Polawax GP 200 20.0 g.
  Lanolin Anhydrous 2.0 g.
  White Beeswax 2.5 g.
  Methyl hydroxybenzoate 0.1 g.
  Distilled Water to 100.0 g.

The polawax, beeswax and lanolin are heated together at 60° C. A solution of methyl hydroxybenzoate is added and homogenization is achieved using high speed stirring. The temperature is then allowed to fall to 50° C. The antibody or fragment thereof of the invention is then added and dispersed throughout, and the composition is allowed to cool with slow speed stirring.

Topical Lotion Composition
  Antibody or fragment thereof of the invention 1.0 g.
  Sorbitan Monolaurate 0.6 g.
  Polysorbate 20 0.6 g.
  Cetostearyl Alcohol 1.2 g.
  Glycerin 6.0 g.
  Methyl Hydroxybenzoate 0.2 g.
  Purified Water B.P. to 100-00 ml. (B.P.=British Pharmacopeia)

The methyl hydroxybenzoate and glycerin are dissolved in 70 ml. of the water at 75° C. The sorbitan monolaurate, polysorbate 20 and cetostearyl alcohol are melted together at 75° C. and added to the aqueous solution. The resulting emulsion is homogenized, allowed to cool with continuous stirring and the antibody or fragment thereof of the invention is added as a suspension in the remaining water. The whole suspension is stirred until homogenized.

Eye Drop Composition
  Antibody or fragment thereof of the invention 0.5 g.
  Methyl Hydroxybenzoate 0.01 g.
  Propyl Hydroxybenzoate 0.04 g.
  Purified Water B.P. to 100-00 ml.

The methyl and propyl hydroxybenzoates are dissolved in 70 ml. purified water at 75° C. and the resulting solution is allowed to cool. The antibody or fragment thereof of the invention is then added, and the solution is sterilized by filtration through a membrane filter (0.022 μm pore size), and packed aseptically into suitable sterile containers.

Composition for Administration by Inhalation

For an aerosol container with a capacity of 15-20 ml: mix 10 mg. of an antibody or fragment thereof of the invention with 0.2-0.5% of a lubricating agent, such as polysorbate 85 or oleic acid, and disperse such mixture in a propellant, such as freon, preferably in a combination of (1,2 dichlorotetrafluoroethane) and difluorochloro-methane and put into an appropriate aerosol container adapted for either intranasal or oral inhalation administration.

Composition for Administration by Inhalation

For an aerosol container with a capacity of 15-20 ml: dissolve 10 mg. of an antibody or fragment thereof of the invention in ethanol (6-8 ml.), add 0.1-0.2% of a lubricating agent, such as polysorbate 85 or oleic acid; and disperse such in a propellant, such as freon, preferably in combination of (1.2 dichlorotetra-fluoroethane) and difluorochloromethane, and put into an appropriate aerosol container adapted for either intranasal or oral inhalation administration.

The antibodies and pharmaceutical compositions of the invention are particularly useful for parenteral administration, i.e., subcutaneously, intramuscularly or intravenously. The compositions for parenteral administration will commonly comprise a solution of an antibody or fragment thereof of the invention or a cocktail thereof dissolved in an acceptable carrier, preferably an aqueous carrier. A variety of aqueous carriers may be employed, e.g., water, buffered water, 0.4% saline, 0.3% glycine, and the like. These solutions are sterile and generally free of particulate matter. These solutions may be sterilized by conventional, well-known sterilization techniques. The compositions may contain pharmaceutically acceptable auxiliary substances as required to approximate physiological conditions such as pH adjusting and buffering agents, etc. The concentration of the antibody or fragment thereof of the invention in such pharmaceutical formulation can vary widely, i.e., from less than about 0.5%, usually at or at least about 1% to as much as 15 or 20% by weight, and will be selected primarily based on fluid volumes, viscosities, etc., according to the particular mode of administration selected.

Thus, a pharmaceutical composition of the invention for intramuscular injection could be prepared to contain 1 Ml sterile buffered water, and 50 mg. of an antibody or fragment thereof of the invention. Similarly, a pharmaceutical composition of the invention for intravenous infusion could be made up to contain 250 ml. of sterile Ringer's solution, and 150 mg. of an antibody or fragment thereof of the invention. Actual methods for preparing parenterally administrable compositions are well known or will be apparent to those skilled in the art, and are described in more detail in, for example, *Remington's Pharmaceutical Science*, 15th ed., Mack Publishing Company, Easton, Pa., hereby incorporated by reference herein.

The antibodies (or fragments thereof) of the invention can be lyophilized for storage and reconstituted in a suitable carrier prior to use. This technique has been shown to be effective with conventional immune globulins and art-known lyophilization and reconstitution techniques can be employed.

Depending on the intended result, the pharmaceutical composition of the invention can be administered for prophylactic and/or therapeutic treatments. In therapeutic application, compositions are administered to a patient already suffering from a disease, in an amount sufficient to cure or at least partially arrest the disease and its complications. In prophylactic applications, compositions containing the present antibodies or a cocktail thereof are administered to a patient not already in a disease state to enhance the patient's resistance.

Single or multiple administrations of the pharmaceutical compositions can be carried out with dose levels and pattern being selected by the treating physician. In any event, the pharmaceutical composition of the invention should provide a quantity of the altered antibodies (or fragments thereof) of the invention sufficient to effectively treat the patient.

It should also be noted that the antibodies of this invention may be used for the design and synthesis of either peptide or non-peptide compounds (mimetics) which would be useful in the same therapy as the antibody. See, e.g., Saragovi et al., *Science*, 253, 792-795 (1991).

To further illustrate the invention, the following examples are provided. These examples are not intended, nor are they to be construed, as further limiting the invention.

EXAMPLE 1

Recombinant immunoglobulin libraries displayed on the surface of filamentous phage were first described by McCafferty et al, Nature, 348:552-554, 1990 and Barbas et al, *Proc. Natl. Acad. Sci., USA* 88:7978-7982, 1991. Using this technology, high affinity antibodies have been isolated from immune human recombinant libraries (Barbas et al, *Proc.*

Natl. Acad. Sci., USA 589:10164-10168, 1992). Although the phage display concept used is substantially similar to that described by Barbas, 1991, Id. the technique has been modified by the substitution of a unique vector for monkey libraries to reduce the possibility of recombination and improve stability. This vector, pMS, FIG. 1 contains a single lac promoter/operator for efficient transcription and translation of polycistronic heavy and light chain monkey DNA. This vector contains two different leader sequences, the omp A (Movva et al, *J. Biol. Chem.* 255: 27-29 (1980), for the light chain and the pel B (Lei, *J. Bact.*, 4379-109:4383 (1987) for the heavy chain Fd. Both leader sequences are translated into hydrophobic signal peptides that direct the secretion of the heavy and light chain cloned products into the periplasmic space. In the oxidative environment of the periplasm, the two chains fold and disulfide bonds form to create stable Fab fragments. We derived the backbone of the vector from the phagemid bluescript. (Stratagene, La Jolla, Calif.). It contains the gene for the enzyme beta-lactamase that confers ampicillin (carbenicillin) resistance to bacteria that harbor pMS DNA. We also derived, from bluescript, the origin of replication of the multicopy plasmid ColE1 and the origin of replication of the filamentous bacteriophage f1. The origin of replication of phage f1 (the so-called intragenic region), signals the initiation of synthesis of single stranded pMS DNA, the initiation of capsid formation and the termination of RNA synthesis by viral enzymes. The replication and assembly of pMS DNA strands into phage particles requires viral proteins that must be provided by a helper phage. We have used helper phage VCSM13 which is particularly suited for this, since it also contains a gene coding for kanamycin resistance. Bacteria infected with VCSM13 and pMS can be selected by adding both kanamycin and carbenicillin to the growth medium. The bacteria will ultimately produce filamentous phage particles containing either pMS or VCSM13 genomes. Packaging of the helper phage is less efficient than that of pMS, resulting in a mixed phage population that contains predominately recombinant pMS phages. The ends of the phage pick up minor coat proteins specific to each end. Of particular interest here is the gene III product which is present in three to five copies at one end of the phage. The gene III product is 406 amino acid residues and is required for phage infection of *E. coli* via the F pili. The first two domains of the heavy chain, the variable and the CH1 domain, are fused to the carboxy-terminal half of the gene III protein. This recombinant pili protein, directed by the pel B leader, is secreted to the peroplasm where it accumulates and forms disulfide bonds with the light chain before it is incorporated in the coat of the phage. Also, another vector contains a FLAG sequence engineered downstream of the gene III. The FLAG is an 8 amino acid peptide expressed at the carboxy terminal of the Fd protein. We are using commercially available monoclonal anti-FLAG M2 for both purification and detection of phage Fab by ELISA (Brizzard, *Bio Techniques* 16(4):730-731 (1994)).

After constructing the vector pMS, we tested its ability to produce phage bound Fab using control antibody genes. We cloned an anti-tetanus toxoid antibody, (obtained from Dr. Carlos Barbas), into pMS and transformed XLI-blue. We co-infected our cells with VCSM13 and generated phage displaying the anti-tetanus toxoid antibody. We performed efficiency experiments where anti-tetanus toxoid phage were combined with phage beading an irrelevant antibody at 1:100,000. We performed three rounds of panning by applying 50 µl of the mixed phage to antigen (tetanus toxoid) coated polystyrene wells. Non-adherent phage were washed off and the adherent phage were eluted with acid. The eluted phage were used to infect a fresh aliquot of XL1Blue bacteria and helper phage was added. After overnight amplification, phage were prepared and again panned on antigen coated plates. After three rounds of panning, we were able to show that we had successfully enriched for the anti-tetanus toxoid phage. The success of this technology also depends on the ability to prepare soluble Fabs for characterization of the final panned product. This was achieved by excising gene III from the pMS DNA using the restriction enzyme Nhe I followed by re-ligation. After the gene III was excised, the Fab was no longer displayed on the phage surface but accumulated in the piroplasmic space. Lysates were prepared from bacteria expressing soluble Fab and tested for antigen specificity using an ELISA. High levels of soluble Fab were detected.

In order to adapt phage display technology for use with macaque libraries, we developed specific primers for PCR amplifying monkey immunoglobulin genes. These were based on macaque sequences we obtained while developing the PRIMATIZED®. antibody technology (See, U.S. Pat. No. 5,658,570) and databases containing human sequences. (Kabat et al, (1991), "Sequences of Proteins of Immunological Interest," U.S. Dept. of Health and Human Services, National Institute of Health).

We developed three sets of primers to cover amplification of the macaque repertoire. Our first set of primers was designed for amplification of the heavy chain VH and CH1 (Fd) domains. It consisted of a 3' CH1 domain primer and six 5' VH family specific primers that bind in the framework 1 region. Our second set of primers, for amplifying the whole lambda chain, covers the many lambda chain subgroups. It consists of a 3' primer and three 5' degenerate primers that bind in the VL framework 1 region. Our third set of primers was designed for amplification of the kappa chain subgroups. It consists of one 3' primer and five VK framework 1 primers. Using each of these sets, PCR parameters were optimized to obtain strong enough signals from each primer pair so that ample material was available for cloning of the library. We recently created macaque combinatorial libraries in our pMS vector using these optimized PCR conditions. Bone marrow biopsies were taken from CD4 immune monkeys as the source of immunoglobulin RNA. The libraries contained approximately $10^6$ members and are currently being panned or specific binders on antigen coated wells.

EXAMPLE 2

Development of B7/CTLA-4 Reagents

We have generated a number of reagents for the purpose of immunizing monkeys, developing binding and functional assays in vitro, screening heterohybridomas and panning phage libraries. Table 1 lists each reagent and its intended purpose. In the case of B7.1, RNA was extracted from SB cells and converted to cDNA using reverse transcriptase. The first strand cDNA was PCR amplified using B7.1 specific primers and cloned into IDEC's NEOSPLA mammalian expression vectors. CHO cells were transfected with B7.1 NEOSPLA DNA and clones expressing membrane associated B7.1 were identified. The B7.1 fusion protein was generated similarly, except that the PCR amplified B7.1 gene was cloned into a NEOSPLA cassette vector containing the human CH2 and CH3 immunoglobulin genes. CHO cells were transformed with the B7.1/Ig NEOSPLA DNA and stable clones secreting B7.1/Ig fusion protein were amplified. In general, the B7.2 and CTLA4 reagents were generated in the same manner, except that for B7.2 the RNA was isolated from human spleen cells that had been stimulated 24 hours with anti-Ig and IL-4, and for the CTLA4 constructs the gene source was PHA activated human T cells.

TABLE 1

| Reagent | Purpose | CHO Expression |
|---|---|---|
| Soluble B7.1 | Immunization, immunoassays | Yes |
| B7.1 Transfectant | Screening, ELISA | Yes |
| B7.1/Ig Fusion Protein | Inhibition studies, panning | Yes |
| B7.2 Transfectant | Screening, ELISA | Yes |
| B7.2/Ig Fusion Protein | Inhibition studies, panning | To be completed |
| CTLA4 Transfectant | Inhibition studies | To be completed |
| CTLA4/Ig | Inhibition studies | To be completed |

The availability of these reagents, together with monoclonal antibodies to B7.1 (L3074) (Becton Dickinson, 1994) and B7.2 (Fun-1 (Engel et al, *Blood,* 84, 1402-1407, (1994) and purified goat and rabbit antisera, specifically developed to detect monkey Fab fragments, facilitates identification of antibodies having the desired properties.

EXAMPLE 3

Generation of a Phage Display Library

Recombinant phage display libraries are generated from B7.1 and B7.2 immune monkeys. Lymph node and bone marrow biopsies are performed 7-12 days after immunization to harvest RNA rich B cells and plasma cells. RNA is isolated from the lymphocytes using the method described by Chomczynski, *Anal. Biochem.,* 162(1), 156-159 (1987). RNA is converted to cDNA using an oligo dT primer and reverse transcriptase. The first strand cDNA is divided into aliquots and PCR amplified using the sets of kappa, lambda, and heavy chain Fd region primers described earlier and either Pfu polymerase (Stratagene, San Diego) or Taq polymerase (Promega, Madison). The heavy chain PCR amplified products are pooled, cut with Xho I/Spe I restriction enzymes and cloned into the vector pMS. Subsequently, the light chain PCR products are pooled, cut with Sac I/Xba I restriction enzymes, and cloned to create the recombinant library. XLI-Blue *E. coli* is transformed with the library DNA and super-infected with VCSM13 to produce the phage displaying antibodies. The library is panned four rounds on polystyrene wells coated with B7.1 or B7.2 antigen. Individual phage clones from each round of panning are analyzed. The pMS vector DNA is isolated and the gene III excised. Soluble Fab fragments are generated and tested in ELISA for binding to B7.1 and B7.2.

EXAMPLE 4

Characterization of Phage Fab Fragments

The monkey phage Fab fragments are characterized for their specificity and the ability to block B7.1-Ig and B7.2-Ig binding to CTLA-4-Ig or CTLA-4 transfected cells. Phage fragments are also characterized for cross-reactivity after first panning for 4 rounds on the B7 species used for immunization in order to select for high affinity fragments. Fab fragments identified from four rounds of panning either on B7.1 or B7.2 antigen coated surfaces are scaled up by infection and grown in 24 hour fermentation cultures of *E coli*. Fragments are purified by Kodak FLAG binding to a anti-FLAG affinity column. Purified phage Fabs are tested for affinity by an ELISA based direct binding modified Scatchard analysis (Katoh et al, *J. Chem. BioEng.* 76:451-454 (1993)) using Goat anti-monkey Fab antibodies or anti-FLAG MAb conjugated with horseradish peroxidase. The anti-monkey Fab reagents will be absorbed against human heavy chain constant region Ig to remove any cross-reactivity to B7-Ig. Kd values are calculated for each fragment after measurements of direct binding to B7. I-Ig or B7.2-Ig coated plates.

EXAMPLE 5

Phage Fab Fragment Blocking of CTLA-4/B7 Binding

Fab fragments most effectively blocking the binding of B7-Ig at the lowest concentrations are selected as lead candidates. Selections are made by competing off $^{125}$I-B7-Ig binding to CTLA-4-Ig or CTLA-4 transfected cells. Additional selection criteria include, blocking of mixed lymphocyte reaction (MLR), as measured by inhibiting 3H-thymidine uptake in responder cells (Azuma et al, *J. Exp. Med.* 177:845-850; Azuma et al, *Nature* 301:76-79 (1993)) and direct analysis of IL-2 production using IL-2 assay kits. The three or four candidates which are most effective in inhibiting of MLR and CTLA-4 binding assays are chosen for cloning into the above-described mammalian expression vector for transfection into CHO cells and expression of chimeric monkey/human antibodies.

EXAMPLE 6

Generation of Monkey Heterohybridomas

Monkey heterohybridomas secreting monoclonal antibodies are generated from existing immunized animals whose sera tested positive for B7.1 and/or B7.2. Lymph node biopsies are taken from animals positive to either, or both, antigens. The method of hybridoma production is similar to the established method used for the generation of monkey anti-CD4 antibodies (Newman, 1992 (Id.)). Monkeys with high serum titers will have sections of inguinal lymph nodes removed under anesthesia. Lymphocytes are washed from the tissue and fused with KH6/B5 heteromyeloma cells (Carrol et al, *J. Immunol. Meth.* 89:61-72 (1986)) using polyethylene glycol (PEG). Hybridomas are selected on H.A.T. media and stabilized by repeated subcloning in 96 well plates.

Monkey monoclonal antibodies specific for B7.1 antigen are screened for cross-reactivity to B7.2. Monkey anti-B7 antibodies will be characterized for blocking of B7/CTLA-4 binding using the $^{125}$I-B7-Ig binding assay. Inhibition of MLR by 3H-Thymidine uptake and direct measurement of IL-2 production is used to select three candidates. Two candidates will be brought forward in Phase II studies and expressed in CHO cells while repeating all functional studies. For the purposes of developing an animal model for in vivo pharmacology, anti-B7 antibodies will be tested on cells of several animal species. The establishment of an animal model will allow preclinical studies to be carried out for the selected clinical indication.

EXAMPLE 7

As discussed supra, using the above heterohybridoma methods, 4 lead monkey anti-B7.1 antibodies have been identified: 16C10, 7B6, 7C10 and 20C9. These antibodies were characterized as follows:

Scatchard analysis showed that the apparent affinity constants (Kd) for the monkey antibodies binding to B7-Ig coated plates were approximated to be:

| a: | 7C10: | $6.2 \times 10^{-9}$M |
| b: | 16C10: | $8.1 \times 10^{-9}$M |
| c: | 7B6: | $10.7 \times 10^{-9}$M |
| d: | 20C9: | $16.8 \times 10^{-9}$M |

The antibodies were tested in vitro in a mixed lymphocyte reaction assay (MLR). The MLR showed that all 4 anti-B7.1 antibodies inhibit IL-2 production to different extents:

| a: | 7B6: | 5.0 μg/Ml |
| b: | 16C10: | 0.1 μg/Ml |
| c: | 20C9: | 2.0 μg/Ml |
| d: | 7C10: | 5.0 μg/Ml |

The monkey anti-B7.1 antibodies were tested for their ability to bind B7 on human peripheral blood lymphocytes (PBL). FACS analysis showed that all 4 monkey antibodies tested positive.

Monkey antibodies 16C10, 7B6, 7C10 and 20C9 were tested for Clq binding by FACS analysis. Results showed 7C10 monkey Ig had strong human Clq binding after incubating with B7.1 CHO-transfected cells. 16C10 was also positive, while 20C9 and 7B6 monkey antibodies were negative.

EXAMPLE 8

Using the PRIMATIZED® antibody methodology incorporated by reference to commonly assigned U.S. Pat. No. 5,658,570, and using the NEOSPLA® vector system shown in FIG. 2, the heavy and light chain variable domains of 7C10, 7B6 and 16C10 were cloned and PRIMATIZED® forms thereof have been synthesized in CHO cells using the NEOSPLA® vector system. The amino acid and nucleic acid sequences for the PRIMATIZED® 7C10 light and heavy chain, 7B6 light and heavy chain, and 16C10 light and heavy chain are respectively shown in FIGS. 3A (SEQ ID NOS: 1-2), 3B-3C (SEQ ID NOS: 3-4), 4A (SEQ ID NOS: 5-6), 4B-4C (SEQ ID NOS: 7-8), 5A (SEQ ID NOS: 9-10) and 5B-5C (SEQ ID NOS: 11-12).

EXAMPLE 9

Confirming Experiments on the Non-cross-reactivity of the CTLA-4 and PRIMATIZED® Antibody Binding Sites on B7.1.

Figure 6:
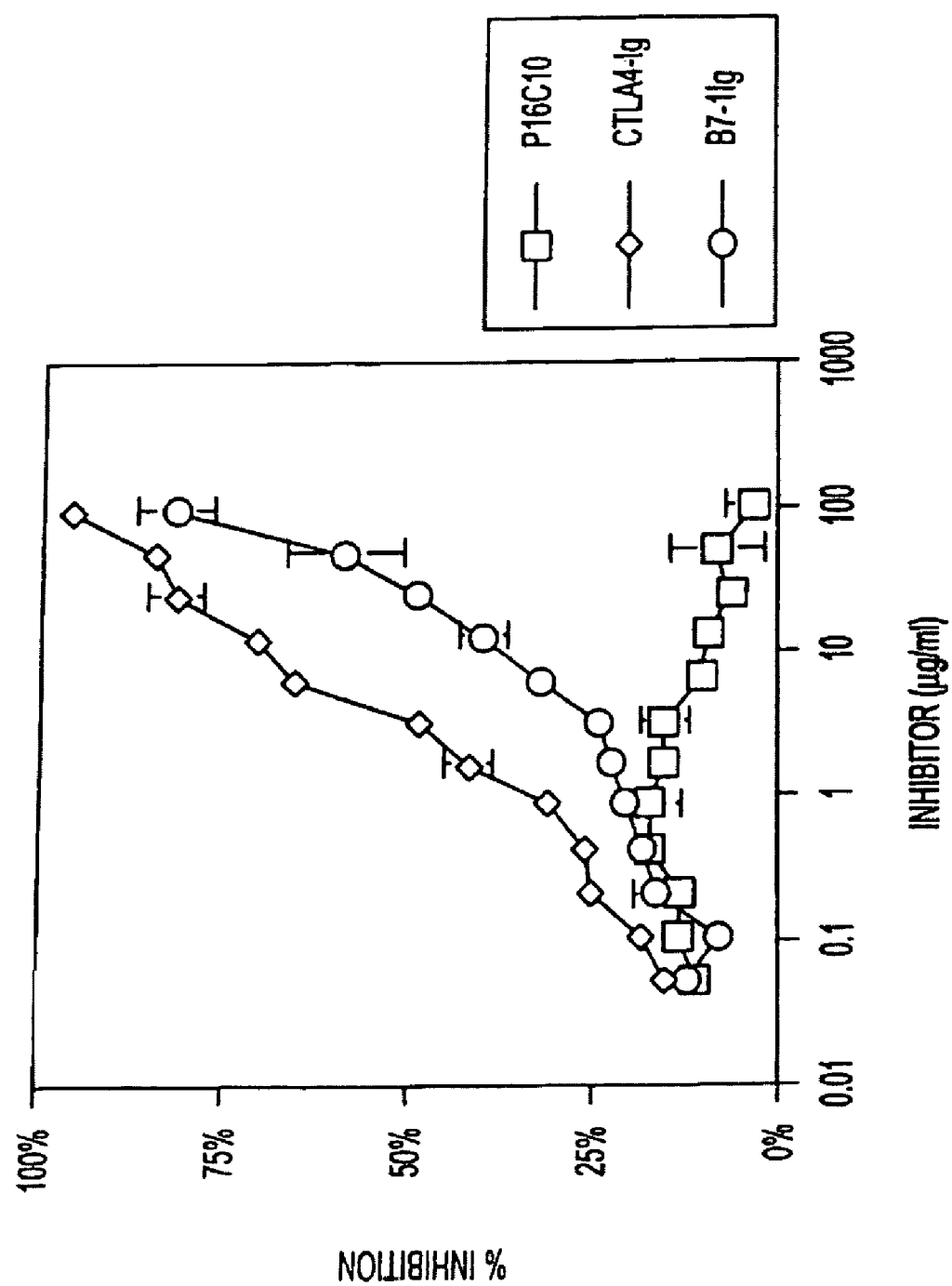
FIG. 6 depicts the inability of P16C10 to block CTLA-4Ig-Biotin binding to B7.1 transfected CHO cells.

In competitive binding assays using biotinylated CTLA-4Ig (FIG. 6), unlabeled PRIMATIZED® 16C10 (i.e., P16C10) was unable to block CTLA-4Ig binding to B7.1 transfected CHO cells. It can be seen that unlabeled CTLA-4Ig and unlabeled B7.1 effectively compete under these conditions.

Figure 7:
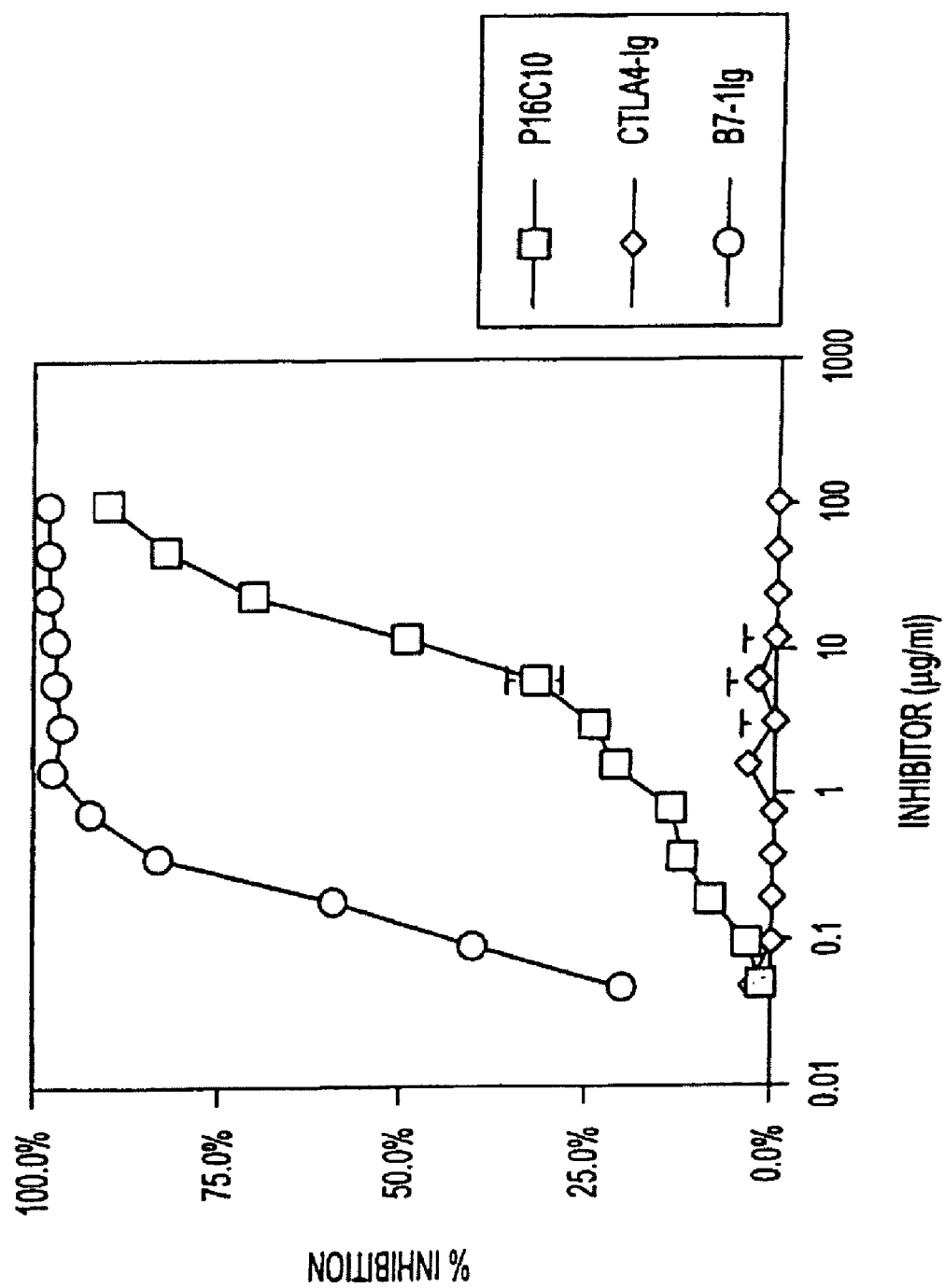
FIG. 7 depicts the inability of CTLA-4Ig to block P16C10-Biotin binding to B7.1 transfected CHO cells.

In a second experiment using Biotinylated P16C10, the same conclusions can be made. In the experiment shown in FIG. 7, binding of P16C10-Biotin is inhibited by both unlabeled P16C10 and B7.1Ig, but not by CTLA-4Ig. Although CTLA-4Ig is reported to be as much as 4-10 fold higher in affinity (Kd=0.4 nM; Morton et al., J Immunol. 156:1047-1054 (1996)), there is no significant inhibition of P16C10 binding even at CTLA-4Ig concentrations as high as 100 fold excess.

Similar results were obtained using the PRIMATIZED® antibody 7C10 (P7C10) when it was substituted for P16C10 in the experiments (data not provided).

EXAMPLE 10

Comparing the Ability of L307.4 and BB-1 Mouse Antibodies to Bind to B7 CHO Cells in the Presence of CTLA-4Ig.

The binding of L307.4 and BB-1 murine anti-B7 antibody in the presence of CTLA-4Ig was studied in order to determine whether the mouse antibody binding sites overlapped with the CTLA-4 binding site. Competition assay experiments using P16C10-Biotin, L307.4-Biotin and CTLA-4Ig-Biotin were done to insure that affinity differences did not prevent detection of competitive binding. The results are shown in FIGS. 8 and 9.

Figure 8:
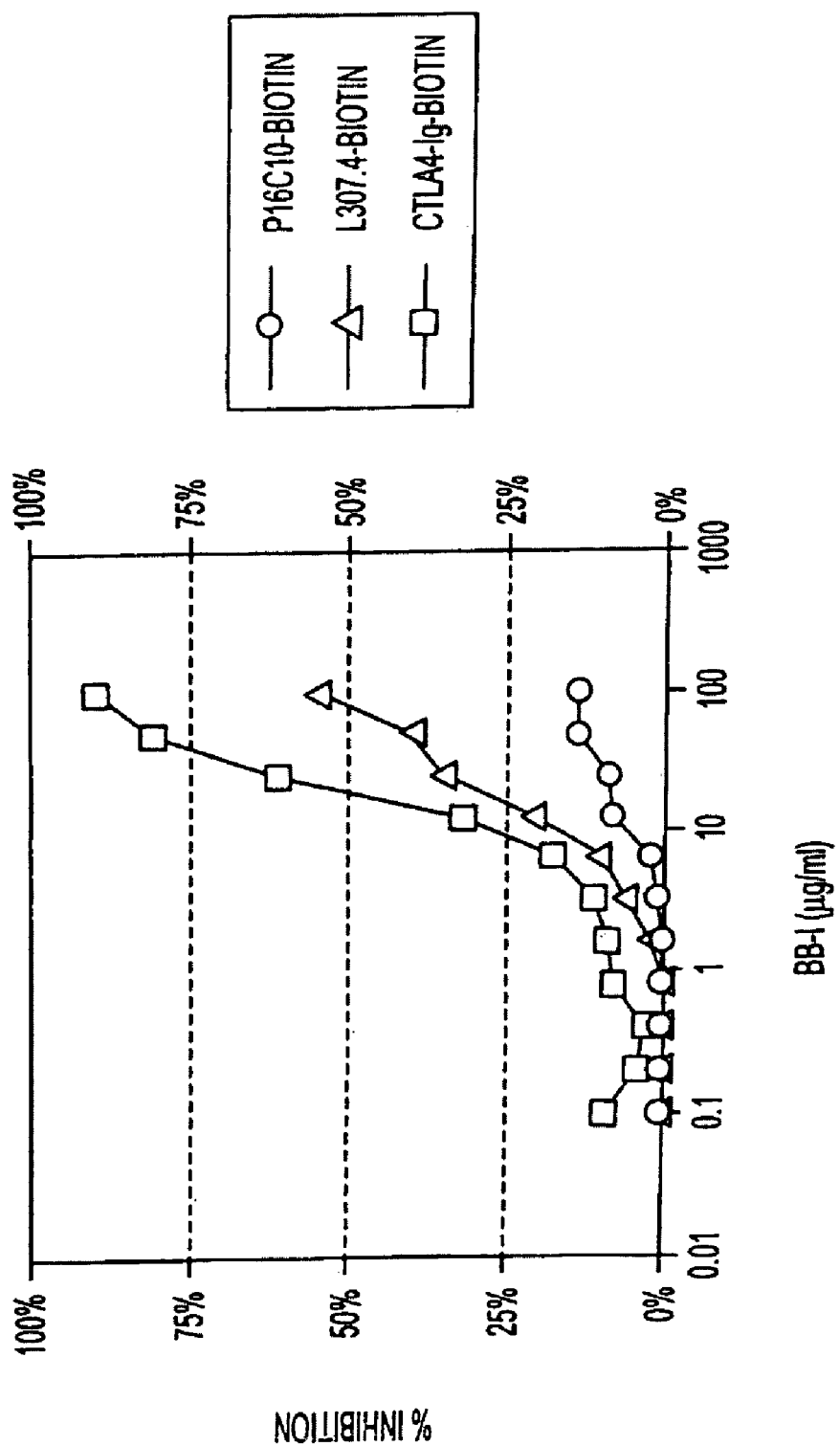
FIG. 8 depicts that BB-1 completely blocks binding of CTLA-4Ig-Biotin to B7.1 transfected CHO cells and further depicts the inability of BB-1 to significantly affect P16C10-Biotin binding to B7.1 transfected CHO cells.

The results of FIG. 8 confirm earlier studies that the mouse antibody BB-1 does not compete with P16C10. These results also show that there is some cross-reactivity to L307.4 of approximately 50%. The results of FIG. 8 confirm that BB-1 and L307.4 both compete with each other and that BB-1 completely blocks binding of CTLA-4Ig-Biotin to B7.1 transfected CHO cells. BB-l does not significantly affect P16C10 binding to B7.1 positive CHO cells.

Figure 9:
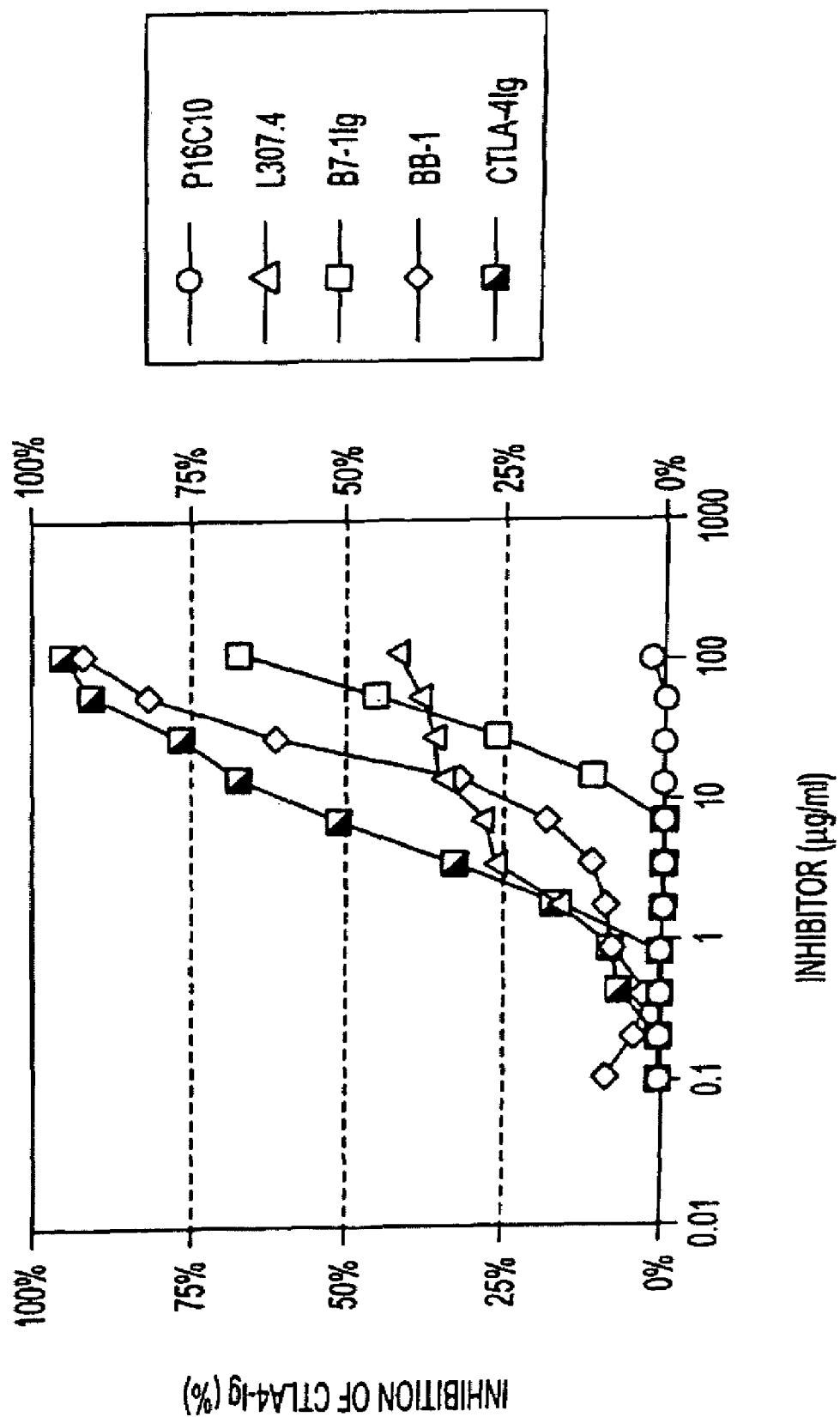
FIG. 9 depicts that CTLA-4Ig-Biotin is effectively blocked by all B7.1 inhibitors except P16C10.

The results shown in FIG. 9 indicate better than 50% competition when CTLA-4Ig-Biotin is used in the binding experiment. FIG. 9 shows that CTLA-4Ig-Biotin is effectively blocked by all B7.1 inhibitors except P16C10, therefore P16C10 recognizes a unique binding determinate on B7.1 which allows the normal CTLA-4 ligand binding in the generation of negative signals. Earlier functional studies (data not shown) suggest a weakened ability of L307.4 to block IL-2 production in allogeneic MLR, which correlates with the hypothesis that it may interfere with CTLA-4 negative signaling. It is not clear how many of the other murine antibodies reported in the literature give complete inhibition of CTLA-4 binding; however, this issue may be important in defining the true functional mechanisms of B7.1 and B7.2 specific antibodies.

These results confirm earlier studies using B7-Ig in competition with P16C10-Biotin for binding to B7.1 transfected CHO cells. The studies also confirm earlier observations of no inhibition of the P16C10 by CTLA-4Ig. These results are highly suggestive that the primate antibodies are specific for a unique B7.1 epitope independent of the CTLA-4 binding site which interacts primarily with CD28. This type of interaction would provide a benefit, since it has the ability to block binding of B7.1 to CD28 receptors while still allowing the negative signaling function of CTLA-4 to occur uninhibited. This perceived interaction may lead to a down regulation of the overall T cell activation response regardless of the predominance of either Th1 or Th2 phenotypes.

Similar results were obtained using P7C10 when it was substituted for P 16C10 in the experiments (data not provided).

EXAMPLE 11

Experiment demonstrating the ability of P16C10 to bind and block B7.1 interactions with CD28 receptor.

Figure 10:
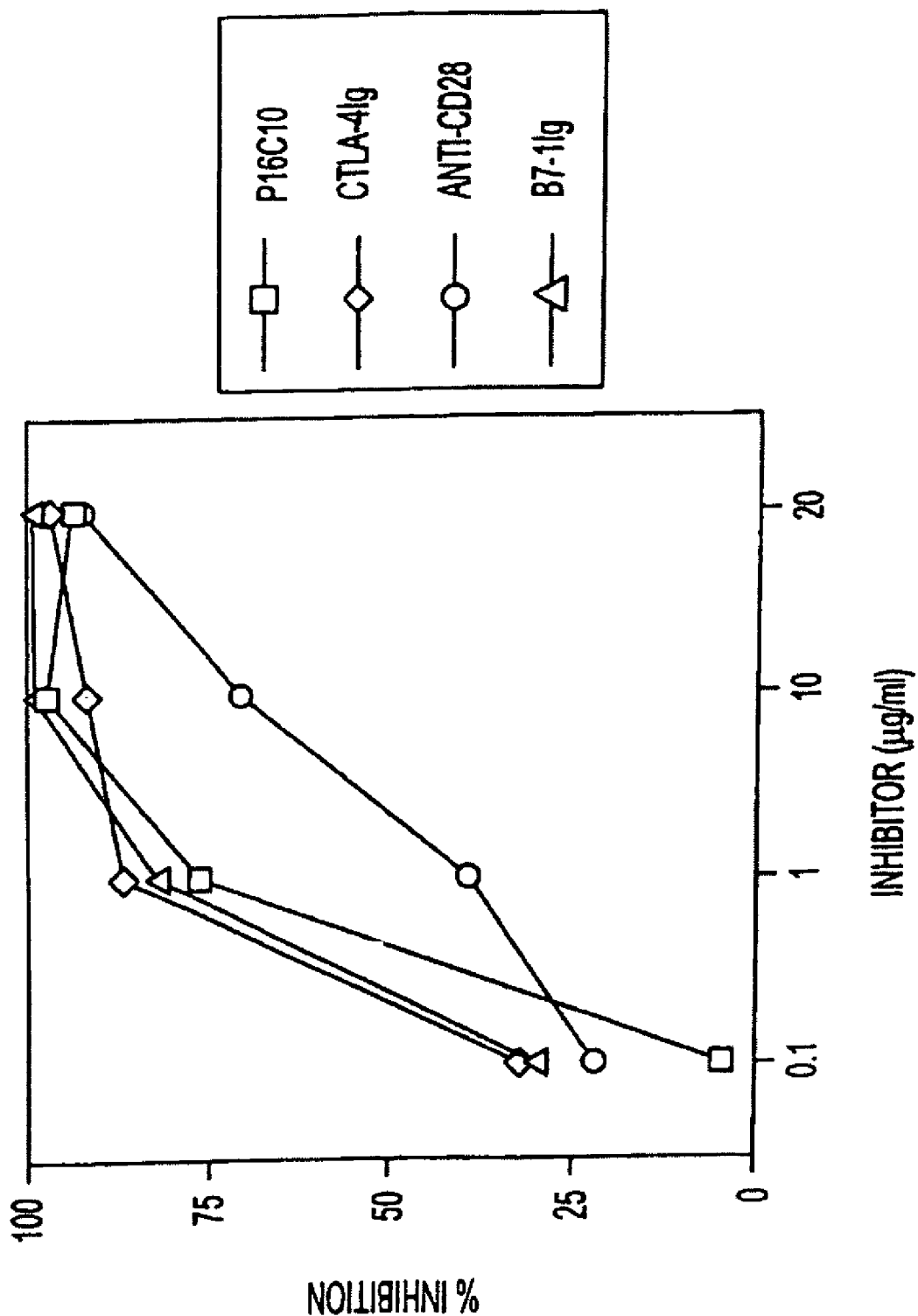
FIG. 10 depicts the ability of P16C10 to block binding of the CD28/B7-1Ig interaction. Data shown are averages of values obtained from four separate experiments.

An experiment to determine if P16C10 binding of B7.1 can block the interaction of B7.1 with CD28 was attempted by radiolabeling B7.1Ig with $^{125}$I, followed by competitive binding to CD28 positive non-activated peripheral blood T lymphocytes. The results shown in FIG. 10 demonstrate that the radiolabeled B7.1Ig binds specifically to the T cells, as confirmed by inhibition with unlabeled B7.1Ig. The results also show that CTLA-4Ig, anti-CD28 and P16C10 are all capable of blocking this interaction. The results further confirm that P16C10 blocks binding of the CD28/B7 interaction with an $IC_{50}$ of <1 ug/mL.

The above results were obtained under conditions where no membrane associated CTLA-4 was expressed (Linsley et al., *J. Exp. Med.* 173:721-730 (1991)) and confirmed by blocking with the anti-CD28 antibody.

Similar results were obtained using P7C10 when it was substituted for P16C10 in the experiments (data not provided).

EXAMPLE 12

IDEC-114 does not Block IL-2 Production in Co-stimulated T Cells

Figure 11:
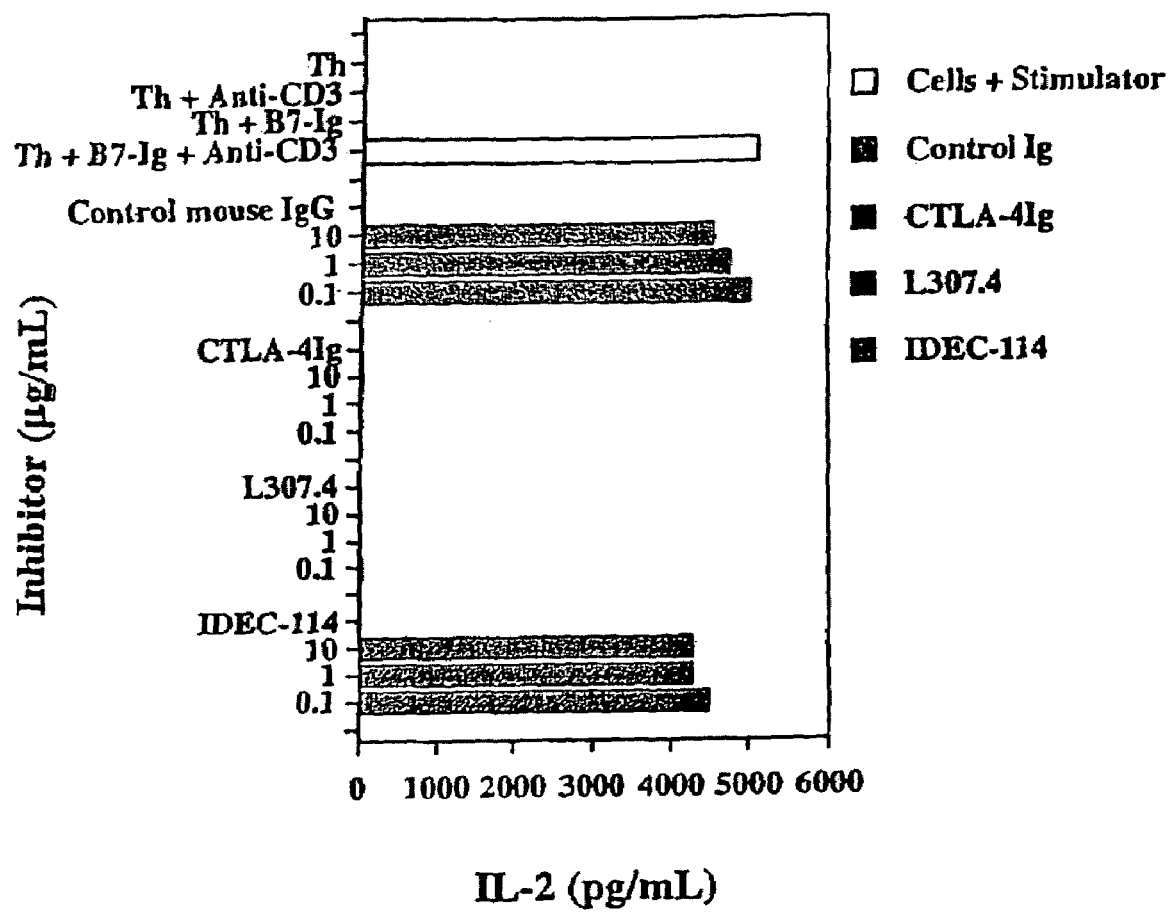
FIG. 11 depicts production of IL-2 in cultures of purified normal human CD4+ lymphocytes when stimulated with sub-optimal amounts of immobilized anti-CD3 antibody and B7-1 (CD80) on latex microbeads. L307.4 is a commercially available murine antibody (BID Pharmingen) that binds specifically to human CD80 and neutralizes CD28:CD80 functional interactions. CTLA-4Ig is a soluble receptor fusion protein that specifically blocks CD80 and CD86 binding to CD28 receptors on T cells. IDLC-114 is a PRIMATIZED® monoclonal antibody that specifically binds to both soluble and membrane forms of the CD80 antigen but does not recognize CTLA-4 or B7-2 antigens. The ratio of anti-CD3 to B7Ig used in the cultures to stimulate T cells was 1:10 (w/w).

In an experiment, the results of which are contained in FIG. 11, a sub-optimal primary signal was induced by attaching an anti-CD3 antibody and a soluble B7Ig fusion protein to covalently coupled protein-A latex microspheres. Initially, a 1:10 ratio of anti-CD3 to B7Ig was used which is a relatively high density of B7 co-stimulatory molecules that is several times greater than normal cells express based on the relative amounts of IL-2 that are typically produced. Purified CD4+ T cells obtained from blood bank donors and co-cultured the cells in presence or absence of soluble CD28:B7 inhibitors that included anti CD80 antibodies L307.4 and IDEC-114 and soluble CTLA-4Ig fusion protein were added at three concentrations ranging from 10 to 0.1 µg/ml. Samples of tissue culture media were collected after 48 hours and the IL-2 cytokine present in the cultures was determined. The results show clearly that beads containing anti-CD3 alone and B7Ig alone produced little or no IL-2. By contrast, both anti-CD3 and B7Ig were present approximately 4500 pg/mL of IL-2 was produced. The results also revealed that both L307.4 and CTLA-4Ig completely inhibited the production of IL-2 at all concentrations where IDEC-114 had no effect. These results suggest that L307.4 and CTLA-4Ig regulate the activation of T cells by a similar mechanism that directly interferes with CD28 signaling to produce the activating cytokine IL-2 while IDEC-114 has no such functional property.

EXAMPLE 13

IDEC-114 does not Block Growth in Co-stimulated T Cells

Figure 12:
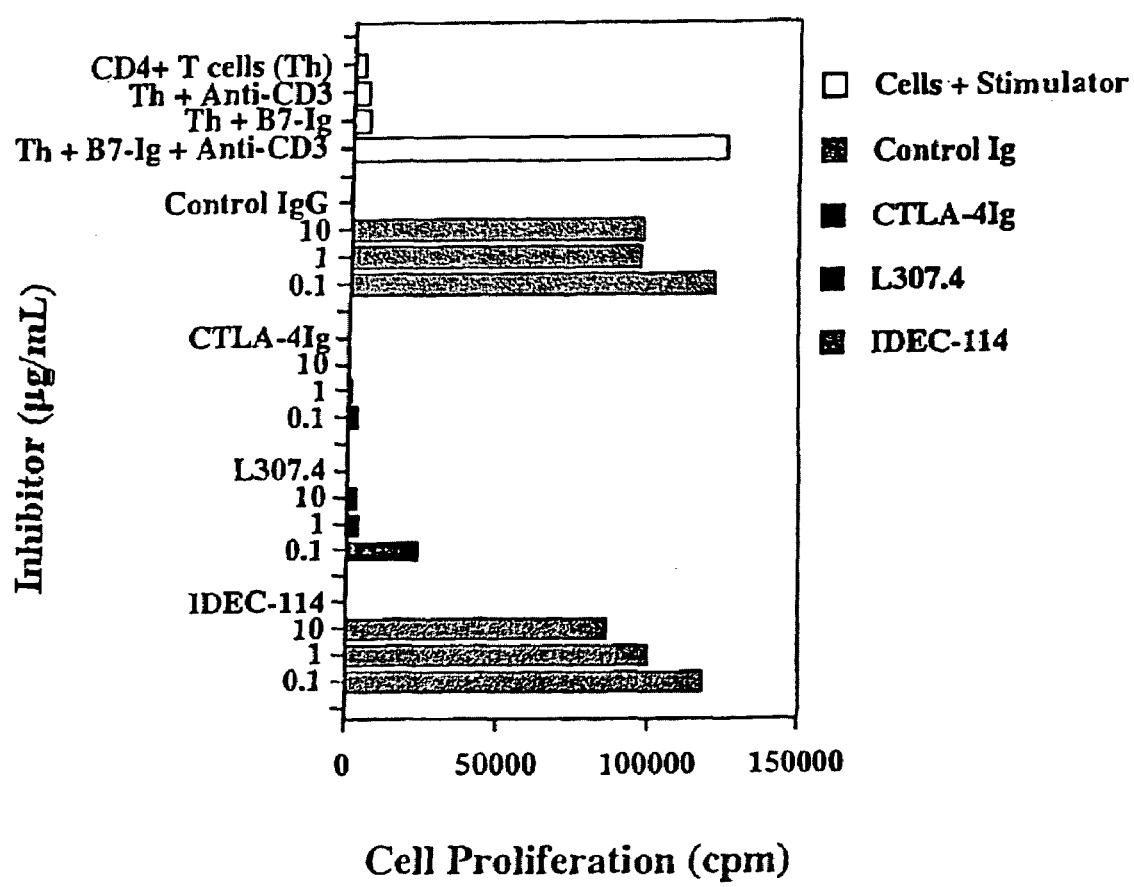
FIG. 12 depicts uptake of H3-Thymidine in cultures of purified normal human CD4+ lymphocytes when stimulated with sub-optimal amounts of immobilized anti-CD3 antibody and B7-1 (CD80) on latex microbeads. L307.4 is a commercially available murine antibody (B/D Pharmingen) that binds specifically to human CD80 and neutralizes CD28:CD80 functional interactions. CTLA-4Ig is a soluble receptor fusion protein that specifically blocks CD80 and CD86 binding to CD28 receptors on T cells. IDEC-114 is a PRIMATIZED® monoclonal antibody that specifically binds to both soluble and membrane forms of the CD80 antigen but does not recognize CTLA-4 or B7-2 antigens.
Figure 13:
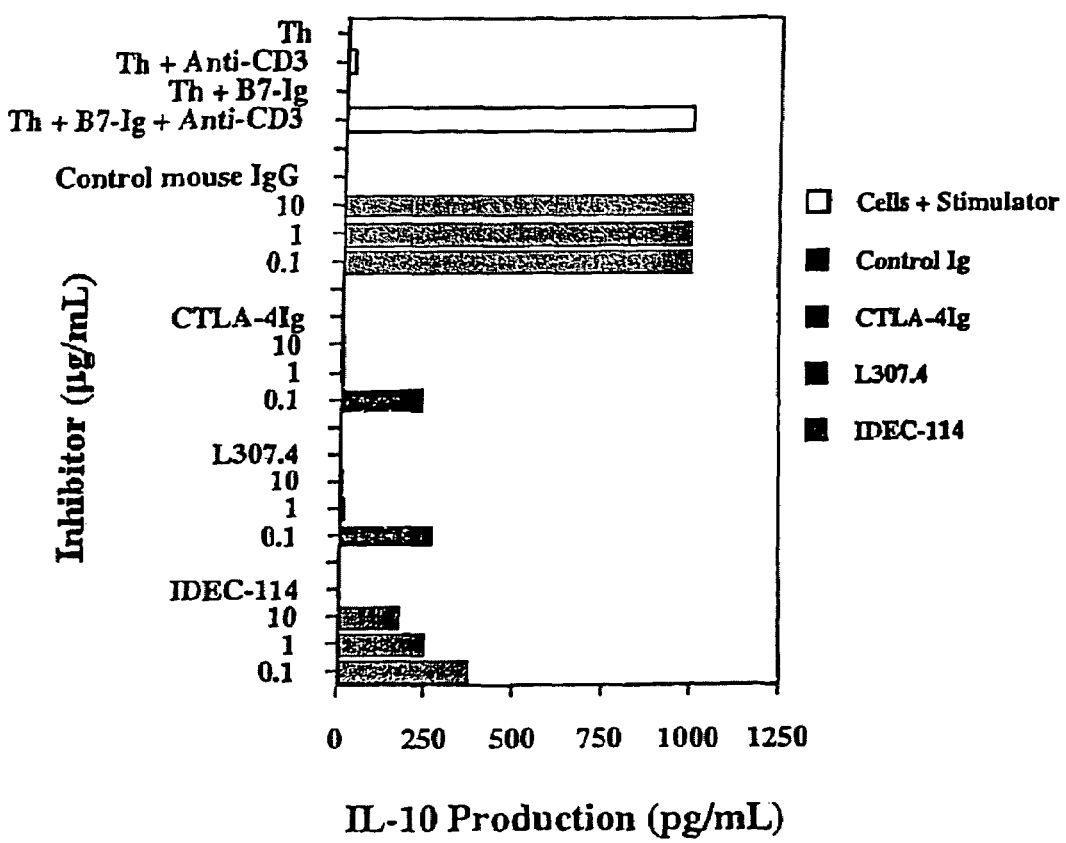
FIG. 13 depicts production of TH2 cytokine IL-10 in cultures of purified normal human CD4+ lymphocytes when stimulated with sub-optimal amounts of immobilized anti-CD3 antibody and B7-1 (CD80) on latex microbeads. Inhibition of IL-10 production by L307.4 anti-CD80 and CTLA-4Ig fusion protein was compared at 0.1,1, and 10 µg/mL.

The same cultures were analyzed for effect on cell growth and similar results to the effects on IL-2 production were obtained. As seen in FIG. 12, L307.4 and CTLA-4Ig were equally effective in totally blocking cell proliferation as determined by uptake of radiolabeled thymidine. Under these same conditions, IDEC-114 had no effect on cell growth. These results further suggest that IDEC-114 is not directly regulating the growth and differentiation properties of CD4+ T cells by blocking the interaction between B7(CD80) and CD28 receptors, unlike other tested anti-B7 antibodies having different binding specifications.

EXAMPLE 14

IDEC-114 Partially Blocks IL-10 Production in Co-stimulated T Cells

The same cultures were analyzed for the presence of the secondary TH2 cytokine IL-10. It was found that both L307.4 and CTLA-4 again completely blocked IL-10 production, whereas IDEC-114 only partially blocked IL-10 proeduction. As seen in FIG. 3, L307.4 and CTLA-4Ig were about equally effective in blocking IL-10 production while IDEC-114 had a partial effect. The partial inhibition of IL-10 by IDEC-114 may be a function of its property of allowing negative signaling to occur in T cells by not interfering with the function of CTLA-4 expressed in T cells. CTLA-4 is upregulated in T cells during co-stimulation and is thought to provide a negative signal to T cells. These results further suggest that IDEC-114 is not regulating the cytokine producing properties of CD4+ T cells through the normal channels involving CD28 signal transduction.

EXAMPLE 15

IDEC-114 Blocks IL-2 Production in T Cells Co-stimulated with Micro-beads Containing Reduced Amounts of B7.

Figure 14:
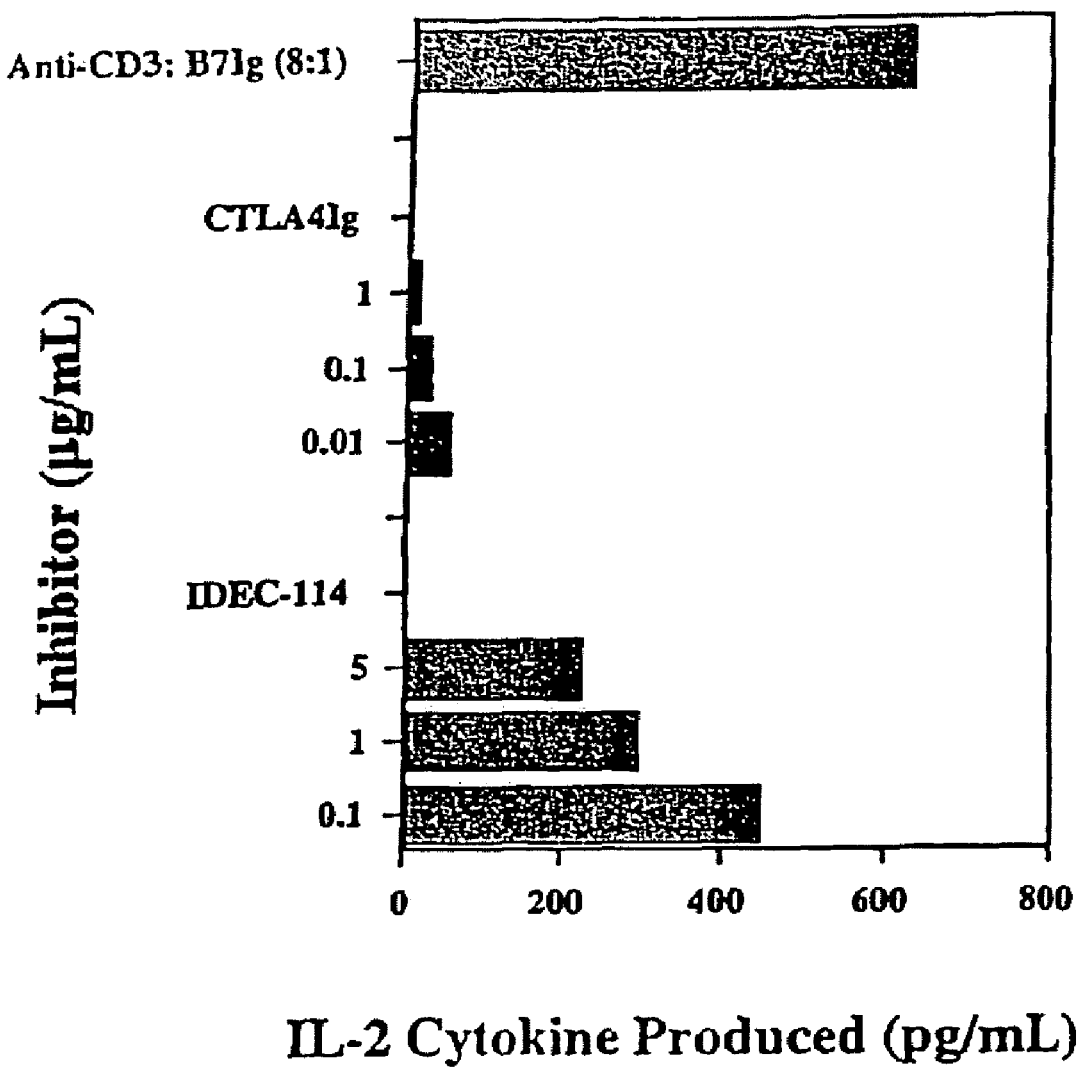
FIG. 14 depicts inhibition of IL-2 cytokine production by CTLA-4Ig and IDEC-114 in cultures of purified human CD4+ T cells. T cells were co-stimulated with anti-CD3 and B7Ig coated latex microbeads with an anti-CD3/B7 ratio (w/w) of 8: 1. IL-2 was determined by growth and uptake of Thymidine by the IL-2 dependent cell line CTLL-2.

In another experiment, the ratio of anti-CD3 to B7-Ig was adjusted on the stimulator beads from a 1:10 ratio to 8:1 or a reduction in B7 of about 80-fold with an 8-fold excess of anti-CD3. The production of IL-2 under these conditions is significantly reduced to typically less than 1000 pg/mL and is more in line with cultures stimulated with mismatched allotypes or CD80 transfected cells. Under these conditions (FIG. 14), we observed near complete inhibition of IL-2 with CTLA-4Ig consistent with results obtained by beads with an anti-CD3/B7-Ig ratio of 1:10. However, with IDEC-114, we routinely observed significant inhibition of IL-2 (50-90%). We are also able to block IL-2 generated in cultures of mixed lymphocytes or when B7 transfected CHO cells are used as stimulators instead of microbeads.

These results suggest that IDEC-114 may function by interfering with adhesion and its effects may be facilitated by reduced expression or maintaining of a lower avidity form of CD80 during co-stimulation.

Analysis of Results

The T cell regulatory properties of IDEC-114 and CTLA-4Ig were compared in an in vitro co-stimulatory system that includes purified CD4+ helper T cells in the absence of accessory cells. In place of accessory antigen-presenting cells, Protein A coated latex microspheres and attached anti-CD3 and B7Ig fusion protein were used. When T-cells were incubated with beads that contained a 10-fold excess of B7 there was a strong co-stimulatory response as measured by IL-2, IL-10 and cell growth that was totally blocked by CTLA-4Ig and a commercially available anti-CD80 monoclonal antibody L307.4. By contrast IDEC-114 had no effect on IL-2 or cell growth but did partially inhibit IL-10 production. It appears that both CTLA-4 and L307.4 possess higher affinities to B7 antigen and that increasing the concentration of IDEC-114 in the cultures should result in the same effect. Based thereon, the affinities of CTLA-4Ig and IDEC-114 (Kd=4 nM) were compared by surface plasmon resonance. It was found that the affinity of CTLA-4Ig (Morten et al., 1996, *J. Immunol.* 156: 1047-1054) was approximately 10-fold higher (Kd=0.4 nM). This assay was performed using as much as 1000-fold greater concentration of IDEC-114 with no effect on IL-2. Also, when T-cells were activated in cultures with beads containing a reduced content of B7 (anti-CD3/B7, 8:1), significant blocking of IL-2 production by both CTLA-4Ig and IDEC-114 was observed. In the latter experiment the equivalent blocking ability of IDEC-114 required approximately 10-fold higher concentration than CTLA-4Ig and was comparable to the difference between the affinities of the two. These results were interpreted by hypothesizing that reduced amounts of B7 on the beads may lead to a reduction in the forming of stable interactions with CD28. This low affinity state may somewhat resemble normal resting B cells. Therefore, with the reduced avidity for adhesion, IDEC-114 may bind to a remote site inducing a conformational change resulting in even lower affinity of CD80 for CD28.

Alternatively, antigen presenting cells that become activated may increase their surface density to the extent that the highly mobile B7 molecules more easily form homodimers. With respect thereto, it has been reported that monomeric forms of B7 have extremely low affinity and fast off-rate kinetics (van der Merwe, et al. 1997, J. Exp. Med., 185: 393-403) and that homodimeric forms can have up to 500-fold higher affinity. A higher affinity form would understandably facilitate cluster or patch formation leading to a more stable receptor ligand complex. Consequently, IDEC-114 may bind to a remote site that could restrict the association of neighboring CD80 molecules and reduce or limit the amount of dimerization effectively limiting the adhesion complex formation.

The observed results suggest that PRIMATIZED® antibodies having the novel binding properties disclosed herein do not influence the regulation of T cells, unlike prior anti-B7.1 antibodies. It is hypothesized, based on these results, that the antibodies of the invention, such as IDEC-114, bind to a unique site on CD80 expressed on antigen presenting cells which prevents the association of CD80 receptors from forming a higher affinity interaction with CD28 receptors on T cells. This would generate a weaker signal through CD28 that under certain conditions could not be overcome by the upregulation of more B7 ligand. However, these same results do not preclude the ability of IDEC-114 to function in other types of immune regulatory mechanisms occurring in vivo where the presence of NK cells and macrophages may contribute to killing of B cells or activated T cells through Fc and complement mediated effects.

It is anticipated that these PRIMATIZED® antibodies, given their probable low antigenicity and human effector function, will be well suited as therapeutics. In this regard, it has been shown that PRIMATIZED® 16C10 (IDEC-114) exhibits human Clq binding.

Those skilled in the art will recognize or be able to ascertain using no more than routine experimentation many equivalents to the specific embodiments of the invention described herein. Such equivalents are intended to be embraced by the following claims.

DEPOSIT INFORMATION

Hybridoma 7B6, hybridoma 7C10, and hybridoma 16C10, which produce antibodies 7C10 and 16C10, respectively, were deposited on May 29, 1996, with the American Type Culture Collection (ATCC), currently located at 10801 University Boulevard, Manassas, Va. 20110-2209, under the provisions of the Budapest Treaty for the International Recognition of the Deposit of Microorganisms for the Purpose of Patent Procedure ("Budapest Treaty"). The ATCC has assigned hybridoma 7B6 the ATCC Accession No. HB-12120, assigned hybridoma 7C10 the ATCC Accession No. HB-12117, and assigned hybridoma 16C10 the ATCC Accession No. HB-12119.

What is claimed is:

1. A host cell expressing a monoclonal antibody or fragment thereof that binds specifically to human CD80 antigen and inhibits the binding of the CD80 antigen to CD28 without inhibiting the binding of the CD80 antigen to CTLA-4.

2. The host cell of claim 1, wherein the antibody competes for binding to CD80 antigen with a 7C10 antibody, produced by a hybridoma assigned ATCC Accession No. HB-12117, or a 16C10 antibody, produced by a hybridoma assigned ATCC Accession No. HB-12119.

3. The host cell of claim 1, wherein the antibody is a human monoclonal antibody or a chimeric or humanized antibody comprising constant regions derived from human constant regions.

4. The host cell of claim 3, wherein the antibody is a chimeric antibody comprising variable regions of an Old World monkey antibody and human constant regions.

5. The host cell of claim 4, wherein the antibody comprises variable regions of a 7C10 antibody, produced by a hybridoma assigned ATCC Accession No. HB-12117, or a 16C10 antibody, produced by a hybridoma assigned ATCC Accession No. HB-12119.

6. The host cell of claim 4, wherein the antibody comprises a human constant region selected from the group consisting of a human gamma 1 constant region, a human gamma 4 constant region, and a human gamma 4PE constant region.

7. The host cell of claim 4, wherein the antibody comprises a light chain variable region having an amino acid sequence shown in SEQ ID NO: 2 and a heavy chain variable region having an amino acid sequence shown in SEQ ID NO: 4.

8. The host cell of claim 4, wherein the antibody comprises a light chain variable region having an amino acid sequence shown in SEQ ID NO: 10 and a heavy chain variable region having an amino acid sequence shown in SEQ ID NO: 12.

9. The host cell of claim 5, wherein the antibody comprises variable regions of a 16C10 antibody, produced by a hybridoma assigned ATCC Accession No. HB-12119 and a human gamma 1 constant region.

10. The host cell of claim 1, wherein the antibody fragment is selected from the group consisting of Fab, F(ab')$_2$ and Fv.

11. The host cell of claim 1, wherein the antibody has the same epitopic specificity as an antibody selected from the group consisting of
    (a) an antibody having as its variable light sequence and variable heavy sequence the amino acid sequence of SEQ ID NO: 2 and SEQ ID NO: 4, respectively;
    (b) an antibody having as its variable light sequence and variable heavy sequence the amino acid sequence of SEQ ID NO: 10 and SEQ ID NO: 12, respectively.

12. A host cell expressing a primatized monoclonal antibody which specifically binds to human CD80 antigen, wherein the antibody comprises the variable light and heavy domains contained in SEQ ID NO: 2 and SEQ ID NO: 4, respectively, and human heavy and light chain constant regions.

13. The host cell of claim 12, wherein the antibody comprises a human gamma 1 or gamma 4 constant region.

14. A host cell expressing a primatized monoclonal antibody which specifically binds to human CD80 antigen, wherein the antibody comprises the variable light and heavy domains contained in SEQ ID NO: 10 and SEQ ID NO: 12, respectively, and human heavy and light chain constant regions.

15. The host cell of claim 14, wherein the antibody comprises a human gamma 1 or a gamma 4 constant region.

16. A host cell expressing a monoclonal antibody, wherein the antibody specifically binds to human CD80 antigen and comprises a light and heavy chain variable domain derived from the light and heavy chain variable domain of an antibody produced by a hybridoma assigned ATCC Accession No. HB-12117 and constant regions derived from human constant regions.

17. The host cell of claim 16, wherein the constant regions are a human heavy chain constant region and a human light chain constant region.

18. The host cell of claim 17, wherein the human heavy chain constant region is a human gamma or gamma 4 constant region.

19. The host cell of claim 16, wherein the antibody comprises variable regions of an antibody produced by the hybridoma assigned ATCC Accession No. HB-12117.

20. The host cell of claim 19, wherein the antibody comprises light chain and heavy chain polypeptide sequences as set forth in SEQ ID NOS. 2 and 4, respectively.

21. A host cell expressing a monoclonal antibody, wherein the antibody specifically binds to human CD80 antigen and comprises a light and heavy chain variable domain derived from the light and heavy chain variable domain of an antibody produced by a hybridoma assigned ATCC Accession No. HB-12119 and constant regions derived from human constant regions.

22. The host cell of claim 21, wherein the constant regions are a human heavy chain constant region and a human light chain constant region.

23. The host cell of claim 22, wherein the human heavy chain constant region is a human gamma or gamma 4 constant region.

24. The host cell of claim 21, wherein the antibody comprises variable regions of an antibody produced by the hybridoma assigned ATCC Accession No. HB-12119.

25. The host cell of claim 24, wherein the antibody comprises light chain and heavy chain polypeptide sequences as set forth in SEQ ID NOS. 10 and 12, respectively.

26. A host cell expressing a monoclonal anti-CD80 antibody, wherein the antibody has the same epitopic specificity as an antibody selected from the group consisting of:
    (a) an antibody having as its variable light sequence and variable heavy sequence the amino acid sequence of SEQ ID NO: 2 and SEQ ID NO: 4, respectively;
    (b) an antibody having as its variable light sequence and variable heavy sequence the amino acid sequence of SEQ ID NO: 6 and SEQ ID NO: 8, respectively, and
    (c) an antibody having as its variable light sequence and variable heavy sequence the amino acid of SEQ ID NO: 10 and SEQ ID NO: 12, respectively.

27. The host cell of claim 26, wherein the antibody has the same epitopic specificity as an antibody having as its variable light and heavy chain sequences a polypeptide having the amino acid sequences contained in SEQ ID NO: 2 and SEQ ID NO: 4, respectively.

28. The host cell of claim 27, wherein the monoclonal antibody comprises variable light and heavy chain sequences set forth as SEQ ID NO: 2 and SEQ ID NO: 4, respectively.

29. The host cell of claim 26, wherein the antibody has the same epitopic specificity as an antibody having as its variable light and heavy chain sequences a polypeptide having the amino acid sequences contained in SEQ ID NO: 10 and SEQ ID NO: 12, respectively.

30. The host cell of claim 29, wherein the monoclonal antibody comprises variable light and heavy chain sequences set forth as SEQ ID NO: 10 and SEQ ID NO: 12, respectively.

31. The host cell of claim 26, wherein the monoclonal antibody or CD80-binding fragment thereof comprises a light chain constant region of a human antibody light chain, and a heavy chain constant region of a human antibody heavy chain.

32. The host cell of claim 31, wherein the monoclonal antibody or CD80-binding fragment thereof comprises a heavy chain constant region selected from human gamma 1 constant region, human gamma 4 constant region, and human gamma 4 PE constant region.

33. The host cell of claim 32, wherein the monoclonal antibody or CD80-binding fragment thereof comprises a human gamma 1 heavy chain constant region.

34. The host cell of claim 30, wherein the monoclonal antibody or CD80-binding fragment thereof comprises a human gamma 1 heavy chain constant region.

35. The host cell of claim 26, wherein the monoclonal antibody or CD80-binding fragment thereof inhibits the interaction of B cell and T cells via the CD80/CD28 pathway.

36. The host cell of claim 35, wherein the monoclonal antibody or CD80-binding fragment thereof inhibits the interaction of B cell and T cells via the CD80/CD28 pathway without inhibiting the interaction of CD80/CTLA-4.

37. The host cell of claim 26, wherein the monoclonal antibody or CD80-binding fragment thereof inhibits the production of IL-2 by T cells.

38. The host cell of claim 26, wherein the CD80-binding fragment is a F(ab')$_2$, Fab, or Fv fragment.

39. The host cell of claim 1, which is a CHO cell.
40. The host cell of claim 12, which is a CHO cell.
41. The host cell of claim 14, which is a CHO cell.
42. The host cell of claim 16, which is a CHO cell.
43. The host cell of claim 21, which is a CHO cell.
44. The host cell of claim 26, which is a CHO cell.

* * * * *

SEQUENCE LISTING

```
<160> NUMBER OF SEQ ID NOS: 12

<210> SEQ ID NO 1
<211> LENGTH: 705
<212> TYPE: DNA
<213> ORGANISM: Homo sapiens
<220> FEATURE:
<221> NAME/KEY: CDS
<222> LOCATION: (1)..(702)

<400> SEQUENCE: 1 atg agg gtc ccc gct cag ctc ctg ggg ctc ctg ctg ctc tgg ctc cca        48
Met Arg Val Pro Ala Gln Leu Leu Gly Leu Leu Leu Leu Trp Leu Pro
  1               5                  10                  15 ggt gca cga tgt gcc tat gaa ctg act cag cca ccc tcg gtg tca gtg        96
Gly Ala Arg Cys Ala Tyr Glu Leu Thr Gln Pro Pro Ser Val Ser Val
             20                  25                  30 tcc cca gga cag acg gcc agg atc acc tgt ggg gga gac aac agt aga       144
Ser Pro Gly Gln Thr Ala Arg Ile Thr Cys Gly Gly Asp Asn Ser Arg
         35                  40                  45 aat gaa tat gtc cac tgg tac cag cag aag cca gcg cgg gcc cct ata       192
Asn Glu Tyr Val His Trp Tyr Gln Gln Lys Pro Ala Arg Ala Pro Ile
     50                  55                  60 ctg gtc atc tat gat gat agt gac cgg ccc tca ggg atc cct gag cga       240
Leu Val Ile Tyr Asp Asp Ser Asp Arg Pro Ser Gly Ile Pro Glu Arg
 65                  70                  75                  80 ttc tct ggc tcc aaa tca ggg aac acc gcc acc ctg acc atc aac ggg       288
Phe Ser Gly Ser Lys Ser Gly Asn Thr Ala Thr Leu Thr Ile Asn Gly
                 85                  90                  95
```

-continued

| | | |
|---|---|---|
| gtc gag gcc ggg gat gag gct gac tat tac tgt cag gtg tgg gac agg<br>Val Glu Ala Gly Asp Glu Ala Asp Tyr Tyr Cys Gln Val Trp Asp Arg<br>                100                          105                          110 | 336 | |
| gct agt gat cat ccg gtc ttc gga gga ggg acc cgg gtg acc gtc cta<br>Ala Ser Asp His Pro Val Phe Gly Gly Gly Thr Arg Val Thr Val Leu<br>            115                          120                          125 | 384 | |
| ggt cag ccc aag gct gcc ccc tcg gtc act ctg ttc ccg ccc tcc tct<br>Gly Gln Pro Lys Ala Ala Pro Ser Val Thr Leu Phe Pro Pro Ser Ser<br>130                            135                          140 | 432 | |
| gag gag ctt caa gcc aac aag gcc aca ctg gtg tgt ctc ata agt gac<br>Glu Glu Leu Gln Ala Asn Lys Ala Thr Leu Val Cys Leu Ile Ser Asp<br>145                          150                          155                        160 | 480 | |
| ttc tac ccg gga gcc gtg aca gtg gcc tgg aag gca gat agc agc ccc<br>Phe Tyr Pro Gly Ala Val Thr Val Ala Trp Lys Ala Asp Ser Ser Pro<br>                    165                          170                          175 | 528 | |
| gtc aag gcg gga gtg gag acc acc aca ccc tcc aaa caa agc aac aac<br>Val Lys Ala Gly Val Glu Thr Thr Thr Pro Ser Lys Gln Ser Asn Asn<br>            180                          185                          190 | 576 | |
| aag tac gcg gcc agc agc tac ctg agc ctg acg cct gag cag tgg aag<br>Lys Tyr Ala Ala Ser Ser Tyr Leu Ser Leu Thr Pro Glu Gln Trp Lys<br>                    195                          200                          205 | 624 | |
| tcc cac aga agc tac agc tgc cag gtc acg cat gaa ggg agc acc gtg<br>Ser His Arg Ser Tyr Ser Cys Gln Val Thr His Glu Gly Ser Thr Val<br>210                            215                          220 | 672 | |
| gag aag aca gtg gcc cct aca gaa tgt tca tga<br>Glu Lys Thr Val Ala Pro Thr Glu Cys Ser<br>225                          230 | 705 | |

<210> SEQ ID NO 2
<211> LENGTH: 234
<212> TYPE: PRT
<213> ORGANISM: Homo sapiens

<400> SEQUENCE: 2

Met Arg Val Pro Ala Gln Leu Leu Gly Leu Leu Leu Leu Trp Leu Pro
1                       5                            10                            15

Gly Ala Arg Cys Ala Tyr Glu Leu Thr Gln Pro Pro Ser Val Ser Val
                    20                          25                          30

Ser Pro Gly Gln Thr Ala Arg Ile Thr Cys Gly Gly Asp Asn Ser Arg
            35                          40                          45

Asn Glu Tyr Val His Trp Tyr Gln Gln Lys Pro Ala Arg Ala Pro Ile
        50                          55                          60

Leu Val Ile Tyr Asp Asp Ser Asp Arg Pro Ser Gly Ile Pro Glu Arg
65                          70                            75                        80

Phe Ser Gly Ser Lys Ser Gly Asn Thr Ala Thr Leu Thr Ile Asn Gly
                    85                          90                          95

Val Glu Ala Gly Asp Glu Ala Asp Tyr Tyr Cys Gln Val Trp Asp Arg
                100                          105                        110

Ala Ser Asp His Pro Val Phe Gly Gly Gly Thr Arg Val Thr Val Leu
            115                          120                          125

Gly Gln Pro Lys Ala Ala Pro Ser Val Thr Leu Phe Pro Pro Ser Ser
        130                          135                          140

Glu Glu Leu Gln Ala Asn Lys Ala Thr Leu Val Cys Leu Ile Ser Asp
145                          150                          155                        160

Phe Tyr Pro Gly Ala Val Thr Val Ala Trp Lys Ala Asp Ser Ser Pro
                165                          170                        175

Val Lys Ala Gly Val Glu Thr Thr Thr Pro Ser Lys Gln Ser Asn Asn

-continued

```
                 180                 185                 190
      Lys Tyr Ala Ala Ser Ser Tyr Leu Ser Leu Thr Pro Glu Gln Trp Lys
              195                 200                 205

Ser His Arg Ser Tyr Ser Cys Gln Val Thr His Glu Gly Ser Thr Val
              210                 215                 220

Glu Lys Thr Val Ala Pro Thr Glu Cys Ser
      225                 230

<210> SEQ ID NO 3
<211> LENGTH: 1431
<212> TYPE: DNA
<213> ORGANISM: Homo sapiens
<220> FEATURE:
<221> NAME/KEY: CDS
<222> LOCATION: (1)..(1428)

<400> SEQUENCE: 3 atg aaa cac ctg tgg ttc ttc ctc ctc ctg gtg gca gct ccc aga tgg        48
Met Lys His Leu Trp Phe Phe Leu Leu Leu Val Ala Ala Pro Arg Trp
  1               5                  10                  15 gtc ctg tcc cag gtg aag ctg cag cag tgg ggc gaa gga ctt ctg cag        96
Val Leu Ser Gln Val Lys Leu Gln Gln Trp Gly Glu Gly Leu Leu Gln
             20                  25                  30 cct tcg gag acc ctg tcc cgc acc tgc gtt gtc tct ggt ggc tcc atc       144
Pro Ser Glu Thr Leu Ser Arg Thr Cys Val Val Ser Gly Gly Ser Ile
         35                  40                  45 agc ggt tac tac tac tgg acc tgg atc cgc cag acc cca ggg agg gga       192
Ser Gly Tyr Tyr Tyr Trp Thr Trp Ile Arg Gln Thr Pro Gly Arg Gly
     50                  55                  60 ctg gag tgg att ggc cat att tat ggt aat ggt gcg acc acc aac tac       240
Leu Glu Trp Ile Gly His Ile Tyr Gly Asn Gly Ala Thr Thr Asn Tyr
 65                  70                  75                  80 aat ccc tcc ctc aag agt cga gtc acc att tca aaa gac acg tcc aag       288
Asn Pro Ser Leu Lys Ser Arg Val Thr Ile Ser Lys Asp Thr Ser Lys
                 85                  90                  95 aac cag ttc ttc ctg aac ttg aat tct gtg acc gac gcg gac acg gcc       336
Asn Gln Phe Phe Leu Asn Leu Asn Ser Val Thr Asp Ala Asp Thr Ala
            100                 105                 110 gtc tat tac tgt gcg aga ggc cct cgc cct gat tgc aca acc att tgt       384
Val Tyr Tyr Cys Ala Arg Gly Pro Arg Pro Asp Cys Thr Thr Ile Cys
        115                 120                 125 tat ggc ggc tgg gtc gat gtc tgg ggc ccg gga gac ctg gtc acc gtc       432
Tyr Gly Gly Trp Val Asp Val Trp Gly Pro Gly Asp Leu Val Thr Val
    130                 135                 140 tcc tca gct agc acc aag ggc cca tcg gtc ttc ccc ctg gca ccc tcc       480
Ser Ser Ala Ser Thr Lys Gly Pro Ser Val Phe Pro Leu Ala Pro Ser
145                 150                 155                 160 tcc aag agc acc tct ggg ggc aca gcg gcc ctg ggc tgc ctg gtc aag       528
Ser Lys Ser Thr Ser Gly Gly Thr Ala Ala Leu Gly Cys Leu Val Lys
                165                 170                 175 gac tac ttc ccc gaa ccg gtg acg gtg tcg tgg aac tca ggc gcc ctg       576
Asp Tyr Phe Pro Glu Pro Val Thr Val Ser Trp Asn Ser Gly Ala Leu
            180                 185                 190 acc agc ggc gtg cac acc ttc ccg gct gtc cta cag tcc tca gga ctc       624
Thr Ser Gly Val His Thr Phe Pro Ala Val Leu Gln Ser Ser Gly Leu
        195                 200                 205 tac tcc ctc agc agc gtg gtg acc gtg ccc tcc agc agc ttg ggc acc       672
Tyr Ser Leu Ser Ser Val Val Thr Val Pro Ser Ser Ser Leu Gly Thr
    210                 215                 220 cag acc tac atc tgc aac gtg aat cac aag ccc agc aac acc aag gtg       720
```

```
Gln Thr Tyr Ile Cys Asn Val Asn His Lys Pro Ser Asn Thr Lys Val
225                 230                 235                 240 gac aag aaa gca gag ccc aaa tct tgt gac aaa act cac aca tgc cca    768
Asp Lys Lys Ala Glu Pro Lys Ser Cys Asp Lys Thr His Thr Cys Pro
                245                 250                 255 ccg tgc cca gca cct gaa ctc ctg ggg gga ccg tca gtc ttc ctc ttc    816
Pro Cys Pro Ala Pro Glu Leu Leu Gly Gly Pro Ser Val Phe Leu Phe
            260                 265                 270 ccc cca aaa ccc aag gac acc ctc atg atc tcc cgg acc cct gag gtc    864
Pro Pro Lys Pro Lys Asp Thr Leu Met Ile Ser Arg Thr Pro Glu Val
        275                 280                 285 aca tgc gtg gtg gtg gac gtg agc cac gaa gac cct gag gtc aag ttc    912
Thr Cys Val Val Val Asp Val Ser His Glu Asp Pro Glu Val Lys Phe
    290                 295                 300 aac tgg tac gtg gac ggc gtg gag gtg cat aat gcc aag aca aag ccg    960
Asn Trp Tyr Val Asp Gly Val Glu Val His Asn Ala Lys Thr Lys Pro
305                 310                 315                 320 cgg gag gag cag tac aac agc acg tac cgt gtg gtc agc gtc ctc acc   1008
Arg Glu Glu Gln Tyr Asn Ser Thr Tyr Arg Val Val Ser Val Leu Thr
                325                 330                 335 gtc ctg cac cag gac tgg ctg aat ggc aag gag tac aag tgc aag gtc   1056
Val Leu His Gln Asp Trp Leu Asn Gly Lys Glu Tyr Lys Cys Lys Val
            340                 345                 350 tcc aac aaa gcc ctc cca gcc ccc atc gag aaa acc atc tcc aaa gcc   1104
Ser Asn Lys Ala Leu Pro Ala Pro Ile Glu Lys Thr Ile Ser Lys Ala
        355                 360                 365 aaa ggg cag ccc cga gaa cca cag gtg tac acc ctg ccc cca tcc cgg   1152
Lys Gly Gln Pro Arg Glu Pro Gln Val Tyr Thr Leu Pro Pro Ser Arg
    370                 375                 380 gat gag ctg acc aag aac cag gtc agc ctg acc tgc ctg gtc aaa ggc   1200
Asp Glu Leu Thr Lys Asn Gln Val Ser Leu Thr Cys Leu Val Lys Gly
385                 390                 395                 400 ttc tat ccc agc gac atc gcc gtg gag tgg gag agc aat ggg cag ccg   1248
Phe Tyr Pro Ser Asp Ile Ala Val Glu Trp Glu Ser Asn Gly Gln Pro
                405                 410                 415 gag aac aac tac aag acc acg cct ccc gtg ctg gac tcc gac ggc tcc   1296
Glu Asn Asn Tyr Lys Thr Thr Pro Pro Val Leu Asp Ser Asp Gly Ser
            420                 425                 430 ttc ttc ctc tac agc aag ctc acc gtg gac aag agc agg tgg cag cag   1344
Phe Phe Leu Tyr Ser Lys Leu Thr Val Asp Lys Ser Arg Trp Gln Gln
        435                 440                 445 ggg aac gtc ttc tca tgc tcc gtg atg cat gag gct ctg cac aac cac   1392
Gly Asn Val Phe Ser Cys Ser Val Met His Glu Ala Leu His Asn His
    450                 455                 460 tac acg cag aag agc ctc tcc ctg tct ccg ggt aaa tga               1431
Tyr Thr Gln Lys Ser Leu Ser Leu Ser Pro Gly Lys
465                 470                 475

<210> SEQ ID NO 4
<211> LENGTH: 476
<212> TYPE: PRT
<213> ORGANISM: Homo sapiens

<400> SEQUENCE: 4

Met Lys His Leu Trp Phe Phe Leu Leu Leu Val Ala Ala Pro Arg Trp
1               5                   10                  15

Val Leu Ser Gln Val Lys Leu Gln Gln Trp Gly Glu Gly Leu Leu Gln
            20                  25                  30

Pro Ser Glu Thr Leu Ser Arg Thr Cys Val Val Ser Gly Gly Ser Ile
        35                  40                  45
```

```
Ser Gly Tyr Tyr Tyr Trp Thr Trp Ile Arg Gln Thr Pro Gly Arg Gly
     50                  55                  60

Leu Glu Trp Ile Gly His Ile Tyr Gly Asn Gly Ala Thr Thr Asn Tyr
 65                  70                  75                  80

Asn Pro Ser Leu Lys Ser Arg Val Thr Ile Ser Lys Asp Thr Ser Lys
                 85                  90                  95

Asn Gln Phe Phe Leu Asn Leu Asn Ser Val Thr Asp Ala Asp Thr Ala
                100                 105                 110

Val Tyr Tyr Cys Ala Arg Gly Pro Arg Pro Asp Cys Thr Thr Ile Cys
            115                 120                 125

Tyr Gly Gly Trp Val Asp Val Trp Gly Pro Gly Asp Leu Val Thr Val
        130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Leu Gly Thr
210                 215                 220

Gln Thr Tyr Ile Cys Asn Val Asn His Lys Pro Ser Asn Thr Lys Val
225                 230                 235                 240

Asp Lys Lys Ala Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Ala Leu His Asn His
450                 455                 460
```

```
Tyr Thr Gln Lys Ser Leu Ser Leu Ser Pro Gly Lys
465                 470                 475

<210> SEQ ID NO 5
<211> LENGTH: 720
<212> TYPE: DNA
<213> ORGANISM: Homo sapiens
<220> FEATURE:
<221> NAME/KEY: CDS
<222> LOCATION: (1)...(717)

<400> SEQUENCE: 5 atg agc ctc cct gct cag ctc ctc ggg ctg cta ttg ctc tgc gtc ccc      48
Met Ser Leu Pro Ala Gln Leu Leu Gly Leu Leu Leu Leu Cys Val Pro
 1               5                  10                  15 ggg tcc agt ggg gaa gtt gtg atg act cag tct cca ctg tcc ctt ccc      96
Gly Ser Ser Gly Glu Val Val Met Thr Gln Ser Pro Leu Ser Leu Pro
            20                  25                  30 atc aca cct gga gag ccg gcc tcc atc tcc tgt agg tct agt caa agc     144
Ile Thr Pro Gly Glu Pro Ala Ser Ile Ser Cys Arg Ser Ser Gln Ser
        35                  40                  45 ctt aaa cac agt aat gga gac acc ttc ctg agt tgg tat cag cag aag     192
Leu Lys His Ser Asn Gly Asp Thr Phe Leu Ser Trp Tyr Gln Gln Lys
    50                  55                  60 cca ggc caa cct cca agg ctc ctg att tat aag gtt tct aac cgg gac     240
Pro Gly Gln Pro Pro Arg Leu Leu Ile Tyr Lys Val Ser Asn Arg Asp
65                  70                  75                  80 tct ggg gtc cca gac aga ttc agc ggc agt ggg gca ggg aca gat ttc     288
Ser Gly Val Pro Asp Arg Phe Ser Gly Ser Gly Ala Gly Thr Asp Phe
                85                  90                  95 aca ctg aaa atc agc gca gtg gag gct gaa gat gtt ggg gtt tat ttc     336
Thr Leu Lys Ile Ser Ala Val Glu Ala Glu Asp Val Gly Val Tyr Phe
            100                 105                 110 tgc ggg caa ggt aca agg act cct ccc act ttc ggc gga ggg acc aag     384
Cys Gly Gln Gly Thr Arg Thr Pro Pro Thr Phe Gly Gly Gly Thr Lys
        115                 120                 125 gtg gaa atc aaa cgt acg gtg gct gca cca tct gtc ttc atc ttc ccg     432
Val Glu Ile Lys Arg Thr Val Ala Ala Pro Ser Val Phe Ile Phe Pro
    130                 135                 140 cca tct gat gag cag ttg aaa tct gga act gcc tct gtt gtg tgc ctg     480
Pro Ser Asp Glu Gln Leu Lys Ser Gly Thr Ala Ser Val Val Cys Leu
145                 150                 155                 160 ctg aat aac ttc tat ccc aga gag gcc aaa gta cag tgg aag gtg gat     528
Leu Asn Asn Phe Tyr Pro Arg Glu Ala Lys Val Gln Trp Lys Val Asp
                165                 170                 175 aac gcc ctc caa tcg ggt aac tcc cag gag agt gtc aca gag cag gac     576
Asn Ala Leu Gln Ser Gly Asn Ser Gln Glu Ser Val Thr Glu Gln Asp
            180                 185                 190 agc aag gac agc acc tac agc ctc agc agc acc ctg acg ctg agc aaa     624
Ser Lys Asp Ser Thr Tyr Ser Leu Ser Ser Thr Leu Thr Leu Ser Lys
        195                 200                 205 gca gac tac gag aaa cac aaa gtc tac gcc tgc gaa gtc acc cat cag     672
Ala Asp Tyr Glu Lys His Lys Val Tyr Ala Cys Glu Val Thr His Gln
    210                 215                 220 ggc ctg agc tcg ccc gtc aca aag agc ttc aac agg gga gag tgt tga     720
Gly Leu Ser Ser Pro Val Thr Lys Ser Phe Asn Arg Gly Glu Cys
225                 230                 235

<210> SEQ ID NO 6
<211> LENGTH: 239
<212> TYPE: PRT
<213> ORGANISM: Homo sapiens
```

<400> SEQUENCE: 6

```
Met Ser Leu Pro Ala Gln Leu Leu Gly Leu Leu Leu Leu Cys Val Pro
1               5                   10                  15

Gly Ser Ser Gly Glu Val Val Met Thr Gln Ser Pro Leu Ser Leu Pro
            20                  25                  30

Ile Thr Pro Gly Glu Pro Ala Ser Ile Ser Cys Arg Ser Ser Gln Ser
        35                  40                  45

Leu Lys His Ser Asn Gly Asp Thr Phe Leu Ser Trp Tyr Gln Gln Lys
    50                  55                  60

Pro Gly Gln Pro Pro Arg Leu Leu Ile Tyr Lys Val Ser Asn Arg Asp
65                  70                  75                  80

Ser Gly Val Pro Asp Arg Phe Ser Gly Ser Gly Ala Gly Thr Asp Phe
                85                  90                  95

Thr Leu Lys Ile Ser Ala Val Glu Ala Glu Asp Val Gly Val Tyr Phe
            100                 105                 110

Cys Gly Gln Gly Thr Arg Thr Pro Pro Thr Phe Gly Gly Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

<210> SEQ ID NO 7
<211> LENGTH: 1437
<212> TYPE: DNA
<213> ORGANISM: Homo sapiens
<220> FEATURE:
<221> NAME/KEY: CDS
<222> LOCATION: (1)..(1434)

<400> SEQUENCE: 7

```
atg ggt tgg agc ctc atc ttg ctc ttc ctt gtc gct gtt gct acg cgt     48
Met Gly Trp Ser Leu Ile Leu Leu Phe Leu Val Ala Val Ala Thr Arg
1               5                   10                  15 gtc cag tgt gag gtg caa ctg gtg gag tct ggg gga ggc ttg gtc cag     96
Val Gln Cys Glu Val Gln Leu Val Glu Ser Gly Gly Gly Leu Val Gln
            20                  25                  30 cct ggc ggg tcc ctg aga gtc tcc tgt gca gtc tct gga ttc acc ttc    144
Pro Gly Gly Ser Leu Arg Val Ser Cys Ala Val Ser Gly Phe Thr Phe
        35                  40                  45 agt gac cac tac atg tat tgg ttc cgc cag gct cca ggg aag ggg ccg    192
Ser Asp His Tyr Met Tyr Trp Phe Arg Gln Ala Pro Gly Lys Gly Pro
    50                  55                  60 gaa tgg gta ggt ttc att aga aac aaa ccg aac ggt ggg aca aca gaa    240
Glu Trp Val Gly Phe Ile Arg Asn Lys Pro Asn Gly Gly Thr Thr Glu
65                  70                  75                  80
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| tac | gcc | gcg | tct | gtg | aaa | gac | aga | ttc | acc | atc | tcc | aga | gat | gat | tcc | 288 |
| Tyr | Ala | Ala | Ser | Val | Lys | Asp | Arg | Phe | Thr | Ile | Ser | Arg | Asp | Asp | Ser |     |
|     |     |     |     | 85  |     |     |     |     | 90  |     |     |     |     | 95  |     |     |
| aaa | agc | atc | gcc | tat | ctg | caa | atg | agc | agc | ctg | aaa | atc | gag | gac | acg | 336 |
| Lys | Ser | Ile | Ala | Tyr | Leu | Gln | Met | Ser | Ser | Leu | Lys | Ile | Glu | Asp | Thr |     |
|     |     |     | 100 |     |     |     |     | 105 |     |     |     |     | 110 |     |     |     |
| gcc | gtc | tat | tac | tgt | act | aca | tcc | tac | att | tca | cat | tgt | cgg | ggt | ggt | 384 |
| Ala | Val | Tyr | Tyr | Cys | Thr | Thr | Ser | Tyr | Ile | Ser | His | Cys | Arg | Gly | Gly |     |
|     |     | 115 |     |     |     |     | 120 |     |     |     |     | 125 |     |     |     |     |
| gtc | tgc | tat | gga | ggt | tac | ttc | gaa | ttc | tgg | ggc | cag | ggc | gcc | ctg | gtc | 432 |
| Val | Cys | Tyr | Gly | Gly | Tyr | Phe | Glu | Phe | Trp | Gly | Gln | Gly | Ala | Leu | Val |     |
|     | 130 |     |     |     |     | 135 |     |     |     |     | 140 |     |     |     |     |     |
| acc | gtc | tcc | tca | gct | agc | acc | aag | ggc | cca | tcg | gtc | ttc | ccc | ctg | gca | 480 |
| Thr | Val | Ser | Ser | Ala | Ser | Thr | Lys | Gly | Pro | Ser | Val | Phe | Pro | Leu | Ala |     |
| 145 |     |     |     |     | 150 |     |     |     |     | 155 |     |     |     |     | 160 |     |
| ccc | tcc | tcc | aag | agc | acc | tct | ggg | ggc | aca | gcg | gcc | ctg | ggc | tgc | ctg | 528 |
| Pro | Ser | Ser | Lys | Ser | Thr | Ser | Gly | Gly | Thr | Ala | Ala | Leu | Gly | Cys | Leu |     |
|     |     |     |     | 165 |     |     |     |     | 170 |     |     |     |     | 175 |     |     |
| gtc | aag | gac | tac | ttc | ccc | gaa | ccg | gtg | acg | gtg | tcg | tgg | aac | tca | ggc | 576 |
| Val | Lys | Asp | Tyr | Phe | Pro | Glu | Pro | Val | Thr | Val | Ser | Trp | Asn | Ser | Gly |     |
|     |     |     | 180 |     |     |     |     | 185 |     |     |     |     | 190 |     |     |     |
| gcc | ctg | acc | agc | ggc | gtg | cac | acc | ttc | ccg | gct | gtc | cta | cag | tcc | tca | 624 |
| Ala | Leu | Thr | Ser | Gly | Val | His | Thr | Phe | Pro | Ala | Val | Leu | Gln | Ser | Ser |     |
|     |     | 195 |     |     |     |     | 200 |     |     |     |     | 205 |     |     |     |     |
| gga | ctc | tac | tcc | ctc | agc | agc | gtg | gtg | acc | gtg | ccc | tcc | agc | agc | ttg | 672 |
| Gly | Leu | Tyr | Ser | Leu | Ser | Ser | Val | Val | Thr | Val | Pro | Ser | Ser | Ser | Leu |     |
|     | 210 |     |     |     |     | 215 |     |     |     |     | 220 |     |     |     |     |     |
| ggc | acc | cag | acc | tac | atc | tgc | aac | gtg | aat | cac | aag | ccc | agc | aac | acc | 720 |
| Gly | Thr | Gln | Thr | Tyr | Ile | Cys | Asn | Val | Asn | His | Lys | Pro | Ser | Asn | Thr |     |
| 225 |     |     |     |     | 230 |     |     |     |     | 235 |     |     |     |     | 240 |     |
| aag | gtg | gac | aag | aaa | gca | gag | ccc | aaa | tct | tgt | gac | aaa | act | cac | aca | 768 |
| Lys | Val | Asp | Lys | Lys | Ala | Glu | Pro | Lys | Ser | Cys | Asp | Lys | Thr | His | Thr |     |
|     |     |     |     | 245 |     |     |     |     | 250 |     |     |     |     | 255 |     |     |
| tgc | cca | ccg | tgc | cca | gca | cct | gaa | ctc | ctg | ggg | gga | ccg | tca | gtc | ttc | 816 |
| Cys | Pro | Pro | Cys | Pro | Ala | Pro | Glu | Leu | Leu | Gly | Gly | Pro | Ser | Val | Phe |     |
|     |     |     | 260 |     |     |     |     | 265 |     |     |     |     | 270 |     |     |     |
| ctc | ttc | ccc | cca | aaa | ccc | aag | gac | acc | ctc | atg | atc | tcc | cgg | acc | cct | 864 |
| Leu | Phe | Pro | Pro | Lys | Pro | Lys | Asp | Thr | Leu | Met | Ile | Ser | Arg | Thr | Pro |     |
|     |     | 275 |     |     |     |     | 280 |     |     |     |     | 285 |     |     |     |     |
| gag | gtc | aca | tgc | gtg | gtg | gtg | gac | gtg | agc | cac | gaa | gac | cct | gag | gtc | 912 |
| Glu | Val | Thr | Cys | Val | Val | Val | Asp | Val | Ser | His | Glu | Asp | Pro | Glu | Val |     |
|     | 290 |     |     |     |     | 295 |     |     |     |     | 300 |     |     |     |     |     |
| aag | ttc | aac | tgg | tac | gtg | gac | ggc | gtg | gag | gtg | cat | aat | gcc | aag | aca | 960 |
| Lys | Phe | Asn | Trp | Tyr | Val | Asp | Gly | Val | Glu | Val | His | Asn | Ala | Lys | Thr |     |
| 305 |     |     |     |     | 310 |     |     |     |     | 315 |     |     |     |     | 320 |     |
| aag | ccg | cgg | gag | gag | cag | tac | aac | agc | acg | tac | cgt | gtg | gtc | agc | gtc | 1008 |
| Lys | Pro | Arg | Glu | Glu | Gln | Tyr | Asn | Ser | Thr | Tyr | Arg | Val | Val | Ser | Val |     |
|     |     |     |     | 325 |     |     |     |     | 330 |     |     |     |     | 335 |     |     |
| ctc | acc | gtc | ctg | cac | cag | gac | tgg | ctg | aat | ggc | aag | gag | tac | aag | tgc | 1056 |
| Leu | Thr | Val | Leu | His | Gln | Asp | Trp | Leu | Asn | Gly | Lys | Glu | Tyr | Lys | Cys |     |
|     |     |     | 340 |     |     |     |     | 345 |     |     |     |     | 350 |     |     |     |
| aag | gtc | tcc | aac | aaa | gcc | ctc | cca | gcc | ccc | atc | gag | aaa | acc | atc | tcc | 1104 |
| Lys | Val | Ser | Asn | Lys | Ala | Leu | Pro | Ala | Pro | Ile | Glu | Lys | Thr | Ile | Ser |     |
|     |     | 355 |     |     |     |     | 360 |     |     |     |     | 365 |     |     |     |     |
| aaa | gcc | aaa | ggg | cag | ccc | cga | gaa | cca | cag | gtg | tac | acc | ctg | ccc | cca | 1152 |
| Lys | Ala | Lys | Gly | Gln | Pro | Arg | Glu | Pro | Gln | Val | Tyr | Thr | Leu | Pro | Pro |     |
|     | 370 |     |     |     |     | 375 |     |     |     |     | 380 |     |     |     |     |     |
| tcc | cgg | gat | gag | ctg | acc | aag | aac | cag | gtc | agc | ctg | acc | tgc | ctg | gtc | 1200 |
| Ser | Arg | Asp | Glu | Leu | Thr | Lys | Asn | Gln | Val | Ser | Leu | Thr | Cys | Leu | Val |     |
| 385 |     |     |     |     | 390 |     |     |     |     | 395 |     |     |     |     | 400 |     |

```
aaa ggc ttc tat ccc agc gac atc gcc gtg gag tgg gag agc aat ggg    1248
Lys Gly Phe Tyr Pro Ser Asp Ile Ala Val Glu Trp Glu Ser Asn Gly
            405                 410                 415 cag ccg gag aac aac tac aag acc acg cct ccc gtg ctg gac tcc gac    1296
Gln Pro Glu Asn Asn Tyr Lys Thr Thr Pro Pro Val Leu Asp Ser Asp
        420                 425                 430 ggc tcc ttc ttc ctc tac agc aag ctc acc gtg gac aag agc agg tgg    1344
Gly Ser Phe Phe Leu Tyr Ser Lys Leu Thr Val Asp Lys Ser Arg Trp
        435                 440                 445 cag cag ggg aac gtc ttc tca tgc tcc gtg atg cat gag gct ctg cac    1392
Gln Gln Gly Asn Val Phe Ser Cys Ser Val Met His Glu Ala Leu His
450                 455                 460 aac cac tac acg cag aag agc ctc tcc ctg tct ccg ggt aaa tga        1437
Asn His Tyr Thr Gln Lys Ser Leu Ser Leu Ser Pro Gly Lys
465                 470                 475

<210> SEQ ID NO 8
<211> LENGTH: 478
<212> TYPE: PRT
<213> ORGANISM: Homo sapiens

<400> SEQUENCE: 8

Met Gly Trp Ser Leu Ile Leu Leu Phe Leu Val Ala Val Ala Thr Arg
1               5                   10                  15

Val Gln Cys Glu Val Gln Leu Val Glu Ser Gly Gly Gly Leu Val Gln
            20                  25                  30

Pro Gly Gly Ser Leu Arg Val Ser Cys Ala Val Ser Gly Phe Thr Phe
        35                  40                  45

Ser Asp His Tyr Met Tyr Trp Phe Arg Gln Ala Pro Gly Lys Gly Pro
    50                  55                  60

Glu Trp Val Gly Phe Ile Arg Asn Lys Pro Asn Gly Gly Thr Thr Glu
65                  70                  75                  80

Tyr Ala Ala Ser Val Lys Asp Arg Phe Thr Ile Ser Arg Asp Asp Ser
                85                  90                  95

Lys Ser Ile Ala Tyr Leu Gln Met Ser Ser Leu Lys Ile Glu Asp Thr
            100                 105                 110

Ala Val Tyr Tyr Cys Thr Thr Ser Tyr Ile Ser His Cys Arg Gly Gly
        115                 120                 125

Val Cys Tyr Gly Gly Tyr Phe Glu Phe Trp Gly Gln Gly Ala Leu Val
    130                 135                 140

Thr Val Ser Ser Ala Ser Thr Lys Gly Pro Ser Val Phe Pro Leu Ala
145                 150                 155                 160

Pro Ser Ser Lys Ser Thr Ser Gly Gly Thr Ala Ala Leu Gly Cys Leu
                165                 170                 175

Val Lys Asp Tyr Phe Pro Glu Pro Val Thr Val Ser Trp Asn Ser Gly
            180                 185                 190

Ala Leu Thr Ser Gly Val His Thr Phe Pro Ala Val Leu Gln Ser Ser
        195                 200                 205

Gly Leu Tyr Ser Leu Ser Ser Val Val Thr Val Pro Ser Ser Ser Leu
    210                 215                 220

Gly Thr Gln Thr Tyr Ile Cys Asn Val Asn His Lys Pro Ser Asn Thr
225                 230                 235                 240

Lys Val Asp Lys Lys Ala Glu Pro Lys Ser Cys Asp Lys Thr His Thr
                245                 250                 255

Cys Pro Pro Cys Pro Ala Pro Glu Leu Leu Gly Gly Pro Ser Val Phe
            260                 265                 270
```

```
Leu Phe Pro Pro Lys Pro Lys Asp Thr Leu Met Ile Ser Arg Thr Pro
            275                 280                 285

Glu Val Thr Cys Val Val Val Asp Val Ser His Glu Asp Pro Glu Val
        290                 295                 300

Lys Phe Asn Trp Tyr Val Asp Gly Val Glu Val His Asn Ala Lys Thr
305                 310                 315                 320

Lys Pro Arg Glu Glu Gln Tyr Asn Ser Thr Tyr Arg Val Val Ser Val
                325                 330                 335

Leu Thr Val Leu His Gln Asp Trp Leu Asn Gly Lys Glu Tyr Lys Cys
            340                 345                 350

Lys Val Ser Asn Lys Ala Leu Pro Ala Pro Ile Glu Lys Thr Ile Ser
        355                 360                 365

Lys Ala Lys Gly Gln Pro Arg Glu Pro Gln Val Tyr Thr Leu Pro Pro
    370                 375                 380

Ser Arg Asp Glu Leu Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
            420                 425                 430

Gly Ser Phe Phe Leu Tyr Ser Lys Leu Thr Val Asp Lys Ser Arg Trp
        435                 440                 445

Gln Gln Gly Asn Val Phe Ser Cys Ser Val Met His Glu Ala Leu His
    450                 455                 460

Asn His Tyr Thr Gln Lys Ser Leu Ser Leu Ser Pro Gly Lys
465                 470                 475

<210> SEQ ID NO 9
<211> LENGTH: 711
<212> TYPE: DNA
<213> ORGANISM: Homo sapiens
<220> FEATURE:
<221> NAME/KEY: CDS
<222> LOCATION: (1)..(708)

<400> SEQUENCE: 9 atg agg gtc ccc gct cag ctc ctg ggg ctc ctg ctg ctc tgg ctc cca      48
Met Arg Val Pro Ala Gln Leu Leu Gly Leu Leu Leu Leu Trp Leu Pro
  1               5                  10                  15 ggt gca cga tgt gag tct gcc ctg aca cag ccg ccc tca gtg tct ggg      96
Gly Ala Arg Cys Glu Ser Ala Leu Thr Gln Pro Pro Ser Val Ser Gly
             20                  25                  30 gcc cca ggg cag aag gtc acc atc tcg tgc act ggg agc acc tcc aac     144
Ala Pro Gly Gln Lys Val Thr Ile Ser Cys Thr Gly Ser Thr Ser Asn
         35                  40                  45 att gga ggt tat gat cta cat tgg tac cag cag ctc cca gga acg gcc     192
Ile Gly Gly Tyr Asp Leu His Trp Tyr Gln Gln Leu Pro Gly Thr Ala
     50                  55                  60 ccc aaa ctc ctc atc tat gac att aac aag cga ccc tca gga att tct     240
Pro Lys Leu Leu Ile Tyr Asp Ile Asn Lys Arg Pro Ser Gly Ile Ser
 65                  70                  75                  80 gac cga ttc tct ggc tcc aag tct ggt acc gcg gcc tcc ctg gcc atc     288
Asp Arg Phe Ser Gly Ser Lys Ser Gly Thr Ala Ala Ser Leu Ala Ile
                 85                  90                  95 act ggg ctc cag act gag gat gag gct gat tat tac tgc cag tcc tat     336
Thr Gly Leu Gln Thr Glu Asp Glu Ala Asp Tyr Tyr Cys Gln Ser Tyr
            100                 105                 110
```

-continued

```
gac agc agc ctg aat gct cag gta ttc gga gga ggg acc cgg ctg acc    384
Asp Ser Ser Leu Asn Ala Gln Val Phe Gly Gly Gly Thr Arg Leu Thr
        115                 120                 125 gtc cta ggt cag ccc aag gct gcc ccc acg gtc act ctg ttc ccg ccc    432
Val Leu Gly Gln Pro Lys Ala Ala Pro Thr Val Thr Leu Phe Pro Pro
    130                 135                 140 tcc tct gag gag ctt caa gcc aac aag gcc aca ctg gtg tgt ctc ata    480
Ser Ser Glu Glu Leu Gln Ala Asn Lys Ala Thr Leu Val Cys Leu Ile
145                 150                 155                 160 agt gac ttc tac ccg gga gcc gtg aca gtg gcc tgg aag gca gat agc    528
Ser Asp Phe Tyr Pro Gly Ala Val Thr Val Ala Trp Lys Ala Asp Ser
                165                 170                 175 agc ccc gtc aag gcg gga gtg gag acc acc aca ccc tcc aaa caa agc    576
Ser Pro Val Lys Ala Gly Val Glu Thr Thr Thr Pro Ser Lys Gln Ser
            180                 185                 190 aac aac aag tac gcg gcc agc agc tac ctg agc ctg acg cct gag cag    624
Asn Asn Lys Tyr Ala Ala Ser Ser Tyr Leu Ser Leu Thr Pro Glu Gln
        195                 200                 205 tgg aag tcc cac aga agc tac agc tgc cag gtc acg cat gaa ggg agc    672
Trp Lys Ser His Arg Ser Tyr Ser Cys Gln Val Thr His Glu Gly Ser
    210                 215                 220 acc gtg gag aag aca gtg gcc cct aca gaa tgt tca tga                711
Thr Val Glu Lys Thr Val Ala Pro Thr Glu Cys Ser
225                 230                 235
```

<210> SEQ ID NO 10
<211> LENGTH: 236
<212> TYPE: PRT
<213> ORGANISM: Homo sapiens

<400> SEQUENCE: 10

```
Met Arg Val Pro Ala Gln Leu Leu Gly Leu Leu Leu Leu Trp Leu Pro
 1               5                  10                  15

Gly Ala Arg Cys Glu Ser Ala Leu Thr Gln Pro Pro Ser Val Ser Gly
            20                  25                  30

Ala Pro Gly Gln Lys Val Thr Ile Ser Cys Thr Gly Ser Thr Ser Asn
        35                  40                  45

Ile Gly Gly Tyr Asp Leu His Trp Tyr Gln Gln Leu Pro Gly Thr Ala
    50                  55                  60

Pro Lys Leu Leu Ile Tyr Asp Ile Asn Lys Arg Pro Ser Gly Ile Ser
65                  70                  75                  80

Asp Arg Phe Ser Gly Ser Lys Ser Gly Thr Ala Ala Ser Leu Ala Ile
                85                  90                  95

Thr Gly Leu Gln Thr Glu Asp Glu Ala Asp Tyr Tyr Cys Gln Ser Tyr
            100                 105                 110

Asp Ser Ser Leu Asn Ala Gln Val Phe Gly Gly Gly Thr Arg Leu Thr
        115                 120                 125

Val Leu Gly Gln Pro Lys Ala Ala Pro Thr Val Thr Leu Phe Pro Pro
    130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Ser
                165                 170                 175

Ser Pro Val Lys Ala Gly Val Glu Thr Thr Thr Pro Ser Lys Gln Ser
            180                 185                 190

Asn Asn Lys Tyr Ala Ala Ser Ser Tyr Leu Ser Leu Thr Pro Glu Gln
        195                 200                 205
```

```
Trp Lys Ser His Arg Ser Tyr Ser Cys Gln Val Thr His Glu Gly Ser
    210                 215                 220
Thr Val Glu Lys Thr Val Ala Pro Thr Glu Cys Ser
225                 230                 235

<210> SEQ ID NO 11
<211> LENGTH: 1431
<212> TYPE: DNA
<213> ORGANISM: Homo sapiens
<220> FEATURE:
<221> NAME/KEY: CDS
<222> LOCATION: (1)..(1428)

<400> SEQUENCE: 11 atg aaa cac ctg tgg ttc ttc ctc ctc ctg gtg gca gct ccc aga tgg    48
Met Lys His Leu Trp Phe Phe Leu Leu Leu Val Ala Ala Pro Arg Trp
  1               5                  10                  15 gtc ctg tcc cag gtg cag ctg cag gag tcg ggc cca gga ctg gtg aag    96
Val Leu Ser Gln Val Gln Leu Gln Glu Ser Gly Pro Gly Leu Val Lys
             20                  25                  30 cct tcg gag acc ctg tcc ctc acc tgc gct gtc tct ggt ggc tcc atc   144
Pro Ser Glu Thr Leu Ser Leu Thr Cys Ala Val Ser Gly Gly Ser Ile
         35                  40                  45 agc ggt ggt tat ggc tgg ggc tgg atc cgc cag ccc cca ggg aag ggg   192
Ser Gly Gly Tyr Gly Trp Gly Trp Ile Arg Gln Pro Pro Gly Lys Gly
     50                  55                  60 ctg gag tgg att ggg agt ttc tat agt agt agt ggg aac acc tac tac   240
Leu Glu Trp Ile Gly Ser Phe Tyr Ser Ser Ser Gly Asn Thr Tyr Tyr
 65                  70                  75                  80 aac ccc tcc ctc aag agt caa gtc acc att tca aca gac acg tcc aag   288
Asn Pro Ser Leu Lys Ser Gln Val Thr Ile Ser Thr Asp Thr Ser Lys
                 85                  90                  95 aac cag ttc tcc ctg aag ctg aac tct atg acc gcc gcg gac acg gcc   336
Asn Gln Phe Ser Leu Lys Leu Asn Ser Met Thr Ala Ala Asp Thr Ala
            100                 105                 110 gtg tat tac tgt gtg aga gat cgt ctt ttt tca gtt gtt gga atg gtt   384
Val Tyr Tyr Cys Val Arg Asp Arg Leu Phe Ser Val Val Gly Met Val
        115                 120                 125 tac aac aac tgg ttc gat gtc tgg ggc ccg gga gtc ctg gtc acc gtc   432
Tyr Asn Asn Trp Phe Asp Val Trp Gly Pro Gly Val Leu Val Thr Val
    130                 135                 140 tcc tca gct agc acc aag ggc cca tcg gtc ttc ccc ctg gca ccc tcc   480
Ser Ser Ala Ser Thr Lys Gly Pro Ser Val Phe Pro Leu Ala Pro Ser
145                 150                 155                 160 tcc aag agc acc tct ggg ggc aca gcg gcc ctg ggc tgc ctg gtc aag   528
Ser Lys Ser Thr Ser Gly Gly Thr Ala Ala Leu Gly Cys Leu Val Lys
                165                 170                 175 gac tac ttc ccc gaa ccg gtg acg gtg tcg tgg aac tca ggc gcc ctg   576
Asp Tyr Phe Pro Glu Pro Val Thr Val Ser Trp Asn Ser Gly Ala Leu
            180                 185                 190 acc agc ggc gtg cac acc ttc ccg gct gtc cta cag tcc tca gga ctc   624
Thr Ser Gly Val His Thr Phe Pro Ala Val Leu Gln Ser Ser Gly Leu
        195                 200                 205 tac tcc ctc agc agc gtg gtg acc gtg ccc tcc agc agc ttg ggc acc   672
Tyr Ser Leu Ser Ser Val Val Thr Val Pro Ser Ser Ser Leu Gly Thr
    210                 215                 220 cag acc tac atc tgc aac gtg aat cac aag ccc agc aac acc aag gtg   720
Gln Thr Tyr Ile Cys Asn Val Asn His Lys Pro Ser Asn Thr Lys Val
225                 230                 235                 240 gac aag aaa gca gag ccc aaa tct tgt gac aaa act cac aca tgc cca   768
Asp Lys Lys Ala Glu Pro Lys Ser Cys Asp Lys Thr His Thr Cys Pro
```

```
                     245                 250                 255
ccg tgc cca gca cct gaa ctc ctg ggg gga ccg tca gtc ttc ctc ttc      816
Pro Cys Pro Ala Pro Glu Leu Leu Gly Gly Pro Ser Val Phe Leu Phe
            260                 265                 270 ccc cca aaa ccc aag gac acc ctc atg atc tcc cgg acc cct gag gtc      864
Pro Pro Lys Pro Lys Asp Thr Leu Met Ile Ser Arg Thr Pro Glu Val
        275                 280                 285 aca tgc gtg gtg gtg gac gtg agc cac gaa gac cct gag gtc aag ttc      912
Thr Cys Val Val Val Asp Val Ser His Glu Asp Pro Glu Val Lys Phe
    290                 295                 300 aac tgg tac gtg gac ggc gtg gag gtg cat aat gcc aag aca aag ccg      960
Asn Trp Tyr Val Asp Gly Val Glu Val His Asn Ala Lys Thr Lys Pro
305                 310                 315                 320 cgg gag gag cag tac aac agc acg tac cgt gtg gtc agc gtc ctc acc     1008
Arg Glu Glu Gln Tyr Asn Ser Thr Tyr Arg Val Val Ser Val Leu Thr
            325                 330                 335 gtc ctg cac cag gac tgg ctg aat ggc aag gag tac aag tgc aag gtc     1056
Val Leu His Gln Asp Trp Leu Asn Gly Lys Glu Tyr Lys Cys Lys Val
        340                 345                 350 tcc aac aaa gcc ctc cca gcc ccc atc gag aaa acc atc tcc aaa gcc     1104
Ser Asn Lys Ala Leu Pro Ala Pro Ile Glu Lys Thr Ile Ser Lys Ala
    355                 360                 365 aaa ggg cag ccc cga gaa cca cag gtg tac acc ctg ccc cca tcc cgg     1152
Lys Gly Gln Pro Arg Glu Pro Gln Val Tyr Thr Leu Pro Pro Ser Arg
370                 375                 380 gat gag ctg acc aag aac cag gtc agc ctg acc tgc ctg gtc aaa ggc     1200
Asp Glu Leu Thr Lys Asn Gln Val Ser Leu Thr Cys Leu Val Lys Gly
385                 390                 395                 400 ttc tat ccc agc gac atc gcc gtg gag tgg gag agc aat ggg cag ccg     1248
Phe Tyr Pro Ser Asp Ile Ala Val Glu Trp Glu Ser Asn Gly Gln Pro
            405                 410                 415 gag aac aac tac aag acc acg cct ccc gtg ctg gac tcc gac ggc tcc     1296
Glu Asn Asn Tyr Lys Thr Thr Pro Pro Val Leu Asp Ser Asp Gly Ser
        420                 425                 430 ttc ttc ctc tac agc aag ctc acc gtg gac aag agc agg tgg cag cag     1344
Phe Phe Leu Tyr Ser Lys Leu Thr Val Asp Lys Ser Arg Trp Gln Gln
    435                 440                 445 ggg aac gtc ttc tca tgc tcc gtg atg cat gag gct ctg cac aac cac     1392
Gly Asn Val Phe Ser Cys Ser Val Met His Glu Ala Leu His Asn His
450                 455                 460 tac acg cag aag agc ctc tcc ctg tct ccg ggt aaa tga                 1431
Tyr Thr Gln Lys Ser Leu Ser Leu Ser Pro Gly Lys
465                 470                 475

<210> SEQ ID NO 12
<211> LENGTH: 476
<212> TYPE: PRT
<213> ORGANISM: Homo sapiens

<400> SEQUENCE: 12

Met Lys His Leu Trp Phe Phe Leu Leu Leu Val Ala Ala Pro Arg Trp
  1               5                  10                  15

Val Leu Ser Gln Val Gln Leu Gln Glu Ser Gly Pro Gly Leu Val Lys
             20                  25                  30

Pro Ser Glu Thr Leu Ser Leu Thr Cys Ala Val Ser Gly Gly Ser Ile
         35                  40                  45

Ser Gly Gly Tyr Gly Trp Gly Trp Ile Arg Gln Pro Pro Gly Lys Gly
     50                  55                  60

Leu Glu Trp Ile Gly Ser Phe Tyr Ser Ser Ser Gly Asn Thr Tyr Tyr
```

-continued

```
                65                  70                  75                  80
Asn Pro Ser Leu Lys Ser Gln Val Thr Ile Ser Thr Asp Thr Ser Lys
                    85                  90                  95
Asn Gln Phe Ser Leu Lys Leu Asn Ser Met Thr Ala Ala Asp Thr Ala
                    100                 105                 110
Val Tyr Tyr Cys Val Arg Asp Arg Leu Phe Ser Val Gly Met Val
                    115                 120                 125
Tyr Asn Asn Trp Phe Asp Val Trp Gly Pro Gly Val Leu Val Thr Val
        130                 135                 140
Ser Ser Ala Ser Thr Lys Gly Pro Ser Val Phe Pro Leu Ala Pro Ser
145                 150                 155                 160
Ser Lys Ser Thr Ser Gly Gly Thr Ala Ala Leu Gly Cys Leu Val Lys
                    165                 170                 175
Asp Tyr Phe Pro Glu Pro Val Thr Val Ser Trp Asn Ser Gly Ala Leu
                    180                 185                 190
Thr Ser Gly Val His Thr Phe Pro Ala Val Leu Gln Ser Ser Gly Leu
                    195                 200                 205
Tyr Ser Leu Ser Ser Val Val Thr Val Pro Ser Ser Ser Leu Gly Thr
        210                 215                 220
Gln Thr Tyr Ile Cys Asn Val Asn His Lys Pro Ser Asn Thr Lys Val
225                 230                 235                 240
Asp Lys Lys Ala Glu Pro Lys Ser Cys Asp Lys Thr His Thr Cys Pro
                    245                 250                 255
Pro Cys Pro Ala Pro Glu Leu Leu Gly Gly Pro Ser Val Phe Leu Phe
                    260                 265                 270
Pro Pro Lys Pro Lys Asp Thr Leu Met Ile Ser Arg Thr Pro Glu Val
                    275                 280                 285
Thr Cys Val Val Val Asp Val Ser His Glu Asp Pro Glu Val Lys Phe
        290                 295                 300
Asn Trp Tyr Val Asp Gly Val Glu Val His Asn Ala Lys Thr Lys Pro
305                 310                 315                 320
Arg Glu Glu Gln Tyr Asn Ser Thr Tyr Arg Val Val Ser Val Leu Thr
                    325                 330                 335
Val Leu His Gln Asp Trp Leu Asn Gly Lys Glu Tyr Lys Cys Lys Val
                    340                 345                 350
Ser Asn Lys Ala Leu Pro Ala Pro Ile Glu Lys Thr Ile Ser Lys Ala
            355                 360                 365
Lys Gly Gln Pro Arg Glu Pro Gln Val Tyr Thr Leu Pro Pro Ser Arg
        370                 375                 380
Asp Glu Leu Thr Lys Asn Gln Val Ser Leu Thr Cys Leu Val Lys Gly
385                 390                 395                 400
Phe Tyr Pro Ser Asp Ile Ala Val Glu Trp Glu Ser Asn Gly Gln Pro
                    405                 410                 415
Glu Asn Asn Tyr Lys Thr Thr Pro Pro Val Leu Asp Ser Asp Gly Ser
                    420                 425                 430
Phe Phe Leu Tyr Ser Lys Leu Thr Val Asp Lys Ser Arg Trp Gln Gln
            435                 440                 445
Gly Asn Val Phe Ser Cys Ser Val Met His Glu Ala Leu His Asn His
        450                 455                 460
Tyr Thr Gln Lys Ser Leu Ser Leu Ser Pro Gly Lys
465                 470                 475
```